US006339151B1

(12) United States Patent
Shepard et al.

(10) Patent No.: US 6,339,151 B1
(45) Date of Patent: *Jan. 15, 2002

(54) ENZYME CATALYZED THERAPEUTIC AGENTS

(75) Inventors: H. Michael Shepard, Rancho Santa Fe; Michael P. Groziak, Palo Alto, both of CA (US)

(73) Assignee: NewBiotics, Inc., San Diego, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/235,961

(22) Filed: Jan. 22, 1999

Related U.S. Application Data
(60) Provisional application No. 60/108,634, filed on Nov. 16, 1998, provisional application No. 60/076,950, filed on Mar. 5, 1998, and provisional application No. 60/072,264, filed on Jan. 23, 1998.

(51) Int. Cl.$^7$ ................. C07H 19/073; A61K 31/70
(52) U.S. Cl. ............ 536/26.8; 536/28.54; 536/28.55; 536/27.11; 514/50; 514/51
(58) Field of Search ............ 536/26.8, 28.54, 536/28.55, 27.11; 514/50, 51

(56) References Cited

U.S. PATENT DOCUMENTS

| | | | |
|---|---|---|---|
| 4,247,544 A | 1/1981 | Bergstrom et al. | 514/50 |
| 4,267,171 A | 5/1981 | Bergstrom et al. | 514/49 |
| 4,542,210 A | 9/1985 | Sakata et al. | |
| 4,816,570 A | 3/1989 | Farquhar | |
| 4,948,882 A | 8/1990 | Ruth | 536/25.32 |
| 4,975,278 A | 12/1990 | Senter et al. | 424/178.1 |
| 5,070,082 A | 12/1991 | Murdock et al. | 514/105 |
| 5,077,282 A | 12/1991 | Murdock et al. | 514/80 |
| 5,077,283 A | 12/1991 | Murdock et al. | 514/94 |
| 5,085,983 A | 2/1992 | Scanlon | 435/6 |
| 5,116,827 A | 5/1992 | Murdock et al. | 514/82 |
| 5,212,291 A | 5/1993 | Murdock et al. | 536/6.4 |
| 5,233,031 A | 8/1993 | Borch et al. | 536/28.53 |
| 5,264,618 A | 11/1993 | Felgner et al. | 560/224 |
| 5,459,127 A | 10/1995 | Felgner et al. | 514/7 |
| 5,521,161 A | 5/1996 | Malley et al. | 514/45 |
| 5,616,564 A | 4/1997 | Rapaport et al. | 514/44 |
| 5,627,165 A | 5/1997 | Glazier | 514/75 |
| 5,645,988 A | 7/1997 | Vande Woude et al. | |
| 5,798,340 A | 8/1998 | Bischofberger et al. | |
| 5,981,507 A | 11/1999 | Josephson et al. | |

FOREIGN PATENT DOCUMENTS

| | | |
|---|---|---|
| WO | WO 91/17424 | 11/1991 |
| WO | WO 91/17474 | 11/1991 |
| WO | WO 94/03467 | 2/1994 |
| WO | 9508556 | 3/1995 |
| WO | 9610030 | 4/1996 |
| WO | WO 96/29336 | 9/1996 |
| WO | WO 96/40088 | 12/1996 |
| WO | 9640708 | 12/1996 |
| WO | 9920741 | 4/1999 |
| WO | WO 99/23104 | 5/1999 |

OTHER PUBLICATIONS

Firestone et al., "A Comparison of the Effects of Antitumor Agents Upon Normal Human Epidermal Keratinocytes and Human Squamous Cell Carcinoma," *Journal of Investigative Dermatology*, 94(5), 657–661 (May, 1990).

Dagle et al., "Targeted Degradation of mRNA in Xenopus oocytes and Embryos Directed by modified Oligonucleotides: Studies of An2 and Cyclin in Embryogenesis," *Nucleic Acids Research*, 18(16), 4751–4757 (Aug. 25, 1990).

Hakimelahi et al., "Design, Synthesis, and Structure–Activity Relationship of Novel Dinucleotide Analogs as Agents Against Herpes and Human Immunodeficiency Viruses," *Journal of Medicinal Chemistry*, 38(23), 4648–4659 (Nov. 10, 1995).

Naesens et al., "Anti–HIV Activity and Metabolism of Phosphoramidate Derivatives of D4T–MP with Variations in the Amino Acid Moiety," Poster Session 1, The Tenth International Conference on Antiviral Research, Hotel Nikko, Atlanta, GA, Apr. 6–11, 1997; published in *Antiviral Research*, 34(2), p. A54 (Abstract 40), (Apr., 1997).

Ayisi et al., "Comparison of the antiviral effects of 5–methoxymethyldeoxyuridine–5'–monophosphate with adenine arabinoside–5'–monophosphate" *Antiviral Res.* 3:161–174 (1983).

Evrard, A. et al., "An in vitro nucleoside analog screening method for cancer gene therapy" *Chem. Abstracts* 126:Abstract No. 26514 (1996).(Issue No. 3, p. 32, Jan. 20, 1997).

(List continued on next page.)

Primary Examiner—Kathleen Kahler Fonda
Assistant Examiner—L. E. Crane
(74) Attorney, Agent, or Firm—Antoinette F. Konski; McCutchen, Brown, Doyle & Enersen LLP

(57) ABSTRACT

This invention provides a method for identifying potential therapeutic agents by contacting a target cell with a candidate therapeutic agent which is a selective substrate for an endogenous, intracellular enzyme in the cell which is enhanced in its expression as a result of selection by biologic or chemotherapy. This invention also provides methods and examples of molecules for selectively killing a pathological cell by contacting the cell with a prodrug that is a selective substrate for an endogenous, intracellular enzyme. The prodrug is subsequently converted to a cellular toxin. Further provided by this invention is a method for treating a pathology characterized by pathological, hyperproliferative cells in a subject by administering to the subject a prodrug that is a selective substrate for an endogenous, overexpressed, intracellular enzyme, and converted by the enzyme to a cellular toxin in the hyperproliferative cell.

9 Claims, 8 Drawing Sheets

OTHER PUBLICATIONS

Firestone, W.F. et al., "A comparison of the effects of antitumor agents upon normal human epidermal keratinocytes and human squamous cell carcinoma" *Chem. Abstracts 113*:Abstract No. 254 (1990).(Jul. 2, 1990).

Goldberg et al., "Novel cell imaging techniques show induction of apoptosis and proliferation in mesothelial cells by asbestos" *Am. J. Respir. Cell Mol. Biol.* 17:265–271 (1997).

Pardo et al., "The incorporation of deoxyuridine monophosphate into DNA increases the sister–chromatid exchange yield" *Exp. Cell Res.* 168:507–517 (1987).

Larsson, P.–A. et al., "Thymidylate Synthase in Advanced Gastrointestinal and Breast Cancers" *Acta Oncologica* 35(4):469–472 (1996).

Bosslet, K. et al., "Elucidation of the Mechanism Enabling Tumor Selective Prodrug Monotherapy" *Cancer Res.* 58:1195–1201 (Mar. 15, 1998).

Collins, J.M. et al., "Suicide Prodrugs Activated by Thymidylate Synthase: Rationale for Treatment and Noninvasive Imaging of Tumors with Deoxyuridine Analogues" *Clin. Cancer Res.* 5:1976–1981 (Aug. 1999).

Katki, A.G. et al., "Prodrugs Activated by Thymidylate Synthase: Treatment of Tumors with Deoxyuridine Analogs" *Proc. Amer. Assoc. Cancer Res. 39*, Abstract No. 1275 (Mar. 1998).

Husak, R. et al., "Pseudotumour of the tongue caused by herpes simplex virus type 2 in an HIV–1 infected immunosuppressed patient" *British J. Dermatol.* 139:118–121 (1998).

Kodama, E. et al., "Evaluation of antiherpetic compounds using a gastric cancer cell line: Pronounced activity of BVDU against herpes simplex virus replication" *Microbiol. Immunol.* 40(5):359–363 (1996).

Oshiro, Y. et al. "Genotoxic properties of (E)–5–(2–bromovinyl)–2'–deoxyuridine (BVDU)" *Fund. Appl. Toxicol.* 18:491–498 (1992).

Park, N. H. et al., "Chemotherapeutic efficacy of E–5–(–2bromovinyl)–2'–deoxyuridine for orofacial infection with herpes simplex virus type 1 in mice" *J. Infectious Diseases* 145(6):909–913 (1982). (Jun., 1982).

Rogulski, K.R. et al., "Glioma cells transduced with an *Escherichia coli* CD/HSV–1 TK fusion gene exhibit enhanced metabolic suicide and radiosensitivity" *Hum. Gene Ther.* 8:73–85 (1997).(Jan. 1, 1997).

Staschke, K.A. et al., "The in vitro anti–hepatitis B virus activity of FIAU [1–(2'–deoxy–2'–fluoro–1–β–D–arabinofuranosyl–5–iodo) uracil] is selective, reversible, and determined, at least in part, by the host cell" *Antiviral Res.* 23:45–61 (1994).

Abraham et al., "Synthesis and biological activity of aromatic amino acid phosphoramidates of 5–fluoro–2'–deoxyuridine and 1–β–arabinofuranosylcytosine: Evidence of phosphoramidase activity" *J. Med. Chem.* 39:4569–4575 (1996). (Issue No. 23).

Akdas et al., "Glutathione S–transferase and multidrug–resistant phenotype in transitional cell carcinoma of the bladder" *Eur. Urol.* 29(4):483–486 (1996).

Almasan et al., "Genetic instability as a consequence of inappropriate entry into and progression through S–phase" *Can. Metastasis Rev.* 14:59–73 (1995).

Andersen et al., "Detection of c–erbb–2 related protein in sera from breast cancer patients"*Acta Oncol.* 34(4):499–504 (1995).

Anglada et al., "N,N'–cyclization of carbodiimides with 2–(bromomethyl)acrylic acid. A direct entry to the system 5–methylene–6H–pyrimidine–2,4–dione, A new class of thymine analogues" *J. Heterocycl. Chem.* 33:1259–1270 (1996). (Jul./Aug., 1996).

Antelman et al., "Inhibition of tumor cell proliferation in vitro and in vivo by exogenous $p110^{RB}$, the retinoblastoma tumor suppressor protein" *Oncogene* 10:697–704 (1995).

Asakura et al., "Cerium(IV) catalyzed iodination at C5 of uracil nucleosides" *Tetrahedron Lett.* 29(23):2855–2858 (1988).

Asakura et al., "Cerium(IV)–mediated halogenation at C–5 of uracil derivatives" *J. Org. Chem.* 55:4928–4933 (1990). (Issue No. 16).

Balzarini et al., "Incorporation of 5–substituted pyrimidine nucleoside analogues into DNA of a thymidylate synthetase–deficient murine FM3A carcinoma cell line" *Meth. Find. Exp. Clin. Pharmacol.* 7(1):19–28 (1985).

Balzarini, J. et al., "Thymidylate synthase is the principal target enzyme for the cytostatic activity of (E)–5–(2–bromovinyl)–2'–deoxyuridine against murine mammary carcinoma (FM3A) cells transformed with the herpes simplex virus type 1 or type 2 thymidine kinase gene" *Mol. Pharmacol.* 32:410–416 (1987).

Balzarini et al., "Differential mechanism of cytostatic effect of (E)–5–(2–bromovinyl)–2'–deoxyuridine ,9–(1, 3–dihydroxy–2–propoxymethyl)guanine, and other antiherpetic drugs on tumor cells transfected by the thymidine kinase gene of herpes simplex virus type 1 or type 2" *J. Biol. Chem.* 268(9):6332–6337 (1993). (Mar. 25, 1993).

Balzarini et al., "Anti–HIV and anti–HBV activity and resistance profile of 2',3'–dideoxy–3'–thiacytidine (3TC) and its arylphosphoramidate derivative CF 1109" *Biochem. Biophys. Res. Commun.* 225:363–369 (1996). (Issue No. 2).

Balzarini et al., "Conversion of 2,',3'–dideoxyadenosine (ddA) and 2',3'–didehydro–2',3'–dideoxyadenosine (d4A) to their corresponding aryloxyphosphoramidate derivatives markedly potentiates their activity against human immunodeficiency virus and hepatitis B virus" *FEBS Lett.* 410:324–328 (1997).

Banerjee et al., "Molecular mechanisms of resistance to antifolates, a review" *Acta Biochem. Pol.* 42(4):457–464 (1995).

Banerjee et al., "Role of E2F–1 in chemosensitivity" *Cancer Res.* 58:4292–4296 (1998). (Oct. 1, 1998).

Barbour et al., "A naturally occurring tyrosine to histidine replacement at residue 33 of human thymidylate synthase confers resistance to 5–fluoro–2'–deoxyuridine in mammalian and bacterial cells" *Mol. Pharmacol.* 42:242–248 (1992).

Barr, "Inhibition of thymidylate synthetase by 5–alkynyl–2'–deoxyuridylates" *J. Med. Chem.* 24(12):1385–1388 (1981).

Barr et al., "Thymidylate synthetase–catalyzed conversions of E–5–(2–bromovinyl)–2'–deoxyuridylate" *J. Biol. Chem.* 258(22):13627–13631 (1983). (Nov. 25, 1983).

Barr et al., "Reaction of 5–ethynyl–2'–deoxyuridylate with thiols and thymidylate synthetase" *Biochem.* 22:1696–1703 (1983). (Issue No. 7).

Barrett, "Trapping of the C5 methylene intermediate in thymidylate synthase" *J. Am. Chem. Soc.* 120:449–450 (1998). (Issue No. 2).

Benzaria et al., "Synthesis, in vitro antiviral evaluation, and stability studies of bis(S–acyl–2–thioethyl) ester derivatives of 9–[2–(phosphonomethoxy)ethyl]adenine (PMEA) as potential PMEA prodrugs with improved oral bioavailability" *J. Med. Chem.* 39:4958–4965 (1996). (Issue No. 25).

Bergstrom et al., "C–5–substituted pyrimidine nucleosides. 3. Reaction of allylic chlorides, alcohols, and acetates with pyrimidine nucleoside derived organopalladium intermediates" *J. Org. Chem.* 46(7):1432–1441 (1981).

Bergstrom et al., "Synthesis of (E)–5–(3,3, 3–trifluoro–1–propenyl)–2'–deoxyuridine and related analogues: Potent and unusually selective antiviral activity of (E)–5–(3,3,3–trifluoro–1–propenyl)–2'–deoxyuridine against herpes simplex virus type 1" *J. Med. Chem.* 27:279–284 (1984). (Issue No. 3).

Bertino et al., "Resistance mechanisms to methotrexate in tumors" *Stem Cells* 14:5–9 (1996).

Bigge et al., "Palladium–catalyzed coupling reactions of uracil nucleosides and nucleotides" *J. Amer. Chem. Soc.* 102:2033–2038 (1980). (Issue No. 6, Mar. 12, 1980).

Bosslet et al., "A novel one–step tumor–selective prodrug activation system" *Tumor Targeting* 1:45–50 (1995). (Issue No. 1).

Brison, "Gene amplification and tumor progression" *Biochem. Biophys. Acta* 1155:25–41 (1993).

Carl et al., "Protease–activated 'prodrugs' for cancer chemotherapy" *PNAS USA* 77(4):2224–2228 (1980). (Apr., 1980).

Carreras et al., "The catalytic mechanism and structure of thymidylate synthase" *Ann. Rev. Biochem.* 64:721–762 (1995).

Carter et al., "Humanization of an anti–p185$^{HER2}$ antibody for human cancer therapy" *PNAS USA* 89:4285–4289 (1992). (May, 1992).

Cava et al., "Thionation reactions of lawesson's reagents" *Tetrahedron* 41(22):5061–5087 (1985).

Chaudhuri et al., "Very high affinity DNA recognition by bicyclic and cross–linked oligonucleotides" *J. Am. Chem. Soc.* 117:10434–10442 (1995). (Issue No. 2).

Chakravarty et al., "Plasmin–activated prodrugs for cancer chemotherapy. 2. Synthesis and biological activity of peptidyl derivatives of doxorubicin" *J. Med. Chem.* 26(5):638–644 (1983).

Chen et al., "Sensitization of human breast cancer cells to cyclophosphamide and ifosfamide by transfer of a liver cytochrome P450 gene" *Cancer Res.* 56:1331–1340 (1996). (Mar. 15, 1996).

Cho et al., "(E)–5–(3–oxopropen–1–yl)–2'–deoxyuridine and (E)–5–(3–oxopropen–1–yl)–2',3'–dideoxyuridine; New antiviral agents: Synthesis and biological activity" *Tetrahedron Lett.* 35(8):1149–1152 (1994).

Clarke, "Animal models of breast cancer: Their diversity and role in biomedical research" *Breast Can. Res. Treat.* 39:1–6 (1996).

Colacino, "Mechanisms for the anti–hepatitis B virus activity and mitochondrial toxicity of fialuridine (FIAU)" *Antiviral Res.* 29:125–139 (1996).

Connors, "Prodrugs in cancer chemotherapy" *Xenobiotica* 16(10/11):975–988 (1986).

Connors, et al., "Prodrugs in cancer chemotherapy" *Stem Cells* 13:501–511 (1995).

Connors, "Is there a future for cancer chemotherapy?" *Annals Oncol.* 7:445–452 (1996).

Copur et al., "Thymidylate synthase gene amplification in human colon cancer cell lines resistant to 5–fluorouracil" *Biochem. Pharmacol.* 49(10):1419–1426 (1995).

Crisp, "Synthesis of 5–alkenyl–2'–deoxyuridines via organostannanes" *Synth. Commun.* 19(11 & 12):2117–2123 (1989).

Dale et al., "The synthesis and enzymatic polymerization of nucleotides containing mercury: Potential tools for nucleic acid sequencing and structural analysis" *PNAS USA* 70(8):2238–2242 (1973). (Aug., 1973).

Davisson et al., "Expression of human thymidylate synthase in *Escherichia coli*" *J. Biol. Chem.* 264(16):9145–9148 (1989). (Jun. 5, 1989).

Davisson et al. "Expression of human thymidylate synthase in *Escherichia coli*. (Additions and corrections)" *J. Biol. Chem.* 269(48):30740 (1994). Dec. 2, 1994).

De Clercq et al., "Nucleic acid related compounds. 40. Synthesis and biological activities of 5–alkynluracil nucleosides" *J. Med. Chem.* 26:661–666 (1983). (Issue No. 5).

Dicker et al., "Methotrexate resistance in an in vivo mouse tumor due to a non–active–site dihydrofolate reductase mutation" *PNAS USA* 90:11797–11801 (1993).(Dec. 1993).

Dirven et al., "The role of human glutathione S–transferase isoenzymes in the formation of glutathione conjugates of the alkylating cytostatic drug thiotepa" *Can. Res.* 55:1701–1706 (1995). (4/15/.

Dorr et al., "PALA" In: Cancer Chemotherapy Handbook: Appleton & Lange, Norwalk, Connecticut:768–773 (1994).

Dunn et al., "Solution of the conformation and alignment tensors for the binding of trimethoprim and its analogs to dihydrofolate reductase: 3D–quantitative structure–activity relationship study using molecular shape analysis, 3–way partial least–squares regression, and 3–way factor analysis" *J. Med. Chem.* 39:4825–4832 (1996). (Issue No. 24).

Dyer et al., in "Nucleic Acids Chemistry: Improved and new synthetic procedures, methods, and techniques" Townsend, L. B. & Tipson, R. S., eds. (Wiley–Interscience, New York, NY) vol. 4:79–83 (1991).

Eccles et al., "Significance of the c–erbB family of receptor tyrosine kinases in metastatic cancer and their potential as targets for immunotherapy" *Invasion Metastasis* 14(1–6):337–348 (1995).

Eisenbrand et al., "An approach towards more selective anticancer agents" *J. Synthetic Organic Chem.* 10:1246–1258 (1996). (Oct., 1996).

Evrard et al., "An in vitro nucleside analog screening method for cancer gene therapy" *Cell Biol. Toxicol.* 12:345–350 (1996).

Farquhar et al., "Synthesis and antitumor evaluation of bis[(pivaloyloxy)methyl]2'–deoxy–5–fluorouridine 5'–monophosphate (FdUMP): A strategy to introduce nucleotides into cells" *J. Med. Chem.* 37:3902–3909 (1994). (Issue No. 23).

Farquhar et al., "5'–[4–pivaloyloxy)–1,3, 2–dioxaphosphorinan–2–yl]–2'–deoxy–5–fluorouridine: A membrane–permeating prodrug of 5–fluoro–2'–deoxyuridylic acid (FdUMP)" *J. Med. Chem.* 38:488–495 (1994). (Issue No. 3).

Felip et al., "Overexpression of c–erbB–2 in epithelial ovarian cancer" *Cancer* 75(8):2147–2152 (1995). (Apr. 15, 1995).

Finch et al., "Radiation Injury" In: Harrison's Principles of Internal Medicine, 12th edition: McGraw–Hill, Inc., New York, NY:2204–2208 (1991).

Finer–Moore et al., "Refined structures of substrate–bound and phosphate–bound thymidylate synthase from *Lactobacillus casei*" *J. Mol. Biol.* 232:1101–1116 (1993).

Finer–Moore et al., "Crystal structure of thymidylate synthase from T4 phage: Component of a deoxynucleoside triphophate–synthesizing complex" *Biochem.* 33:15459–15468 (1994). (Iss. No. 51.

Firestone et al., "A comparison of the effects of antitumor agents upon normal human epidermal kerarinocytes and human squamous cell carcinoma" *J. Investigative Dermatol.* 94:657–661 (1990). (1/23.

Freed et al., "Evidence for acyloxymethyl esters of pyrimidine 5'-deoxyribonucleotides as extracellular sources of active 5'-deoxyribonucleotides in cultured cells" *Biochem. Pharmacol.* 38(19):3193–3198 (1989).

Fries et al., "Synthesis and biological evaluation of 5'-fluoro-2'-deoxyuridine phosphoramidate analogs" *J. Med. Chem.* 38(14):2672–2680 (1995).

Garrett et al., "Thymidylate synthetase. Catalysis of dehalogenation of 5–bromo–and 5–iodo–2'-deoxyuridylate" *Biochem.* 18(13):2798–2804 (1979).

Goldstein et al., "Genetic aspects of disease" In: Harrison's Principles of Internal Medicine, 12th edition: McGraw–Hill, Inc., New York, NY:21–76 (1991).

Goodwin et al., "Incorporation of alkylthiol chains at C–5 of deoxyuridine" *Tetrahedron Lett.* 34(35):5549–5552 (1993).

Gottesmanm et al., "Genetic analysis of the multidrug transporter" *Ann. Rev. Gen.* 29:607–649 (1995).

Graham et al., "DNA duplexes stabilized by modified monomer residues: Synthesis and stability" *J. Chem. Soc. Perkin Trans. 1*:1131–1138 (1998).

Gros et al., "Isolation and expression of a complementary DNA that confers mutidrug resistance" *Nature* 323:728–731 (1986). (Oct. 23, 1986).

Gros et al., "Mammalian mutidrug resistance gene: Complete cDNA sequence indicates strong homology to bacterial transport proteins" *Cell* 47:371–380 (1986). (Nov., 1986).

Gros et al., "Isolation and characterization of DNA sequences amplified in multidrug–resistant hamster cells" *PNAS USA* 83:337–341 (1986). (Jan., 1986).

Gudkov et al., "Cloning and characterization of DNA sequences amplified in multidrug–resistant djungarian hamster and mouse cells" *Somat. Cell Mol. Genet.* 13(6):609–619 (1987).

Hardy et al., "Atomic structure of thymidylate synthase: Target for rational drug design" *Science* 235:448–455 (1987). (Jan. 23, 1987).

Harris et al., "Adenovirus–mediated p53 gene transfer inhibits growth of human tumor cells expressing mutant p53 protein" *Can. Gene Ther.* 3(2):121–130 (1996).

Hashimoto et al., "Simple separation of tritiated water and [$^3$H] deoxyuridine from [5–$^3$H] deoxyuridine 5'-monophosphate in the thymidylate synthase assay" *Anal. Biochem.* 167:340–346 (1987).

Hengstschläger et al., "The role of p16 in the E2F–dependent thymidine kinase regulation" *Oncogene* 12:1635–1643 (1996).

Hobbs, "Palladium–catalyzed synthesis of alkynylamino nucleosides. A universal linker for nucleic acids" *J. Org. Chem.* 54:3420–3422 (1989). (Issue No. 14).

Horikoshi et al., "Quantitation of thymidylate synthase, dihydrofloate reductase, and DT–diaphorase gene expression in human tumors using the polymerase chain reaction" *Can. Res.* 52:108–116 (1992). (Jan. 1, 1992).

Horn et al., "Fialuridine is phosphorylated and inhibits DNA synthesis in isolated rat hepatic mitochondria" *Antiviral Res.* 34:71–74 (1997).

Hostetler et al., "Enhanced oral absorption and antiviral activity of 1–o–octadecyl–sn–glycero–3–phospho–acyclovir and related compounds in hepatitis B virus infection, in vitro" *Biochem. Pharmacol.* 53:1815–1822 (1997).

Houze, "Detection of thymidylate synthase gene expression levels in formalin–fixed paraffin embedded tissue by semi-quantitative, nonradioactive reverse transcriptase polymerase chain reaction" *Tumor Biol.* 18:53–68 (1997).

Hsaio et al., "Synthesis of 5'-thymidinyl bis(1–aziridinyl)phosphinates as antineoplastic agents" *J. Med. Chem.* 24:887–889 (1981).

Huang et al., "Active site general catalysts are not necessary for some proton transfer reactions of thymidylate synthase" *Biochem.* 36:1869–1873 (1997). (Issue No. 7).

Hudziak et al., "Amplified expression of the HER2/ERBB2 oncogene induces resistance to tumor necrosis factor $\alpha$ in NIH 3T3 cells" *PNAS USA* 85:5102–5106 (1988). (Jul., 1988).

Hudziak et al., "Selection for transformation and met protooncogene amplification in NIH 3T3 fibroblasts using tumor necrosis factor $\alpha$" *Cell Growth & Differentiation* 1:129–134 (1990).

Imai et al., "Studies on phosphorylation. IV. Selective phosphorylation of the primary hydroxyl group in nucleosides" *J. Org. Chem.* 34(6):1547–1550 (1969). (Jun., 1969).

Jackman et al., "Quinazoline–based thymidylate synthase inhibitors: Relationship between structural modifications and polyglutamation" *Anti–Cancer Drug Design* 10:573–589 (1995).

Johnston et al., "Production and characterization of monoclonal antibodies that localize human thymidylate synthase in the cytoplasm of human cells and tissue" *Can. Res.* 51:6668–6676 (1991). (12/15/.

Johnston, "The role of thymidylate synthase expression in prognosis and outcome of adjuvant chemotherapy in patients with rectal cancer" *J. Clin. Oncol.* 12(12):2640–2647 (1994).

Kamb et al., "Cyclin–dependent kinase inhibitors and human cancer" *Curr. Top. Microbiol. Immunol.* 227:139–148 (1998).

Kashani–Sabet et al., "Detection of drug resistance in human tumors by in vitro enzymatic amplification" *Cancer Res.* 48:5775–5778 (1988). (Oct. 15, 1988).

Klecker et al., "Toxicity, metabolism, DNA incorporation with lack of repair, and lactate production for 1–(2'-fluoro–2'-deoxy–$\beta$–D–arabinofuranosyl)–5–iodouracil in U–937 and MOLT–4 cells" *Mol. Pharmacol.* 46:1204–1209 (1994).

Knighton et al., "Structure and kinetic channelling in bifunctional dihydrofolate reductase–thymidylate synthase" *Nature Struct. Biol.* 1(3):186–194 (1994). (Mar. 3, 1994).

Kobayashi et al., "Effect of hammerhead ribozyme against human thymidylate synthase on the cytotoxicity of thymidylate synthase inhibitors" *Jpn. J. Can. Res.* 86:1014–1018 (1995). (Dec. 1995).

Kumar et al., "Synthesis and biological evaluation of some cyclic phosphoramidate nucleoside derivatives" *J. Med. Chem.* 33(9):2368–2735 (1990).

Kundu, "Synthesis and biological activities of [E]–5–(2–acylvinyl) uracils" *Eur. J. Med. Chem.* 28:473–479 (1993).

Kuroboshi et al., "A facile synthesis of difluoromethylene compounds by oxidative fluorodesulfurization of dithioacetals using tetrabutylammonium dihydrogentrifluoride and N–halo compounds" *SYNLETT*:909–910 (1991). (Dec., 1991).

Kuroboshi et al., "A facile synthesis of α,α–difluoroalkyl ethers and carbonyl fluoride acetals by oxidative desulfurization–fluorination" *SYNLETT*:251–252 (1994). (Apr., 1994).

Lam, "Application of combinatorial library methods in cancer research and drug discovery" *Anticancer Drug Design* 12:145–167 (1997).

Lasic, "Doxorubicin in sterically stabilized liposomes" *Nature* 380:561–562 (1996). (Apr. 11, 1996).

Lewis et al., "A serum–resistant cytofection for cellular delivery of antisense oligodeoxynucleotides and plasmid DNA" *PNAS USA.* 93:3176–3181 (1996). (Apr., 1996).

Li et al., "Lack of functional retinoblastoma protein mediates increased resistance to antimetabolites in human sarcoma cell lines" *PNAS USA* 92:10436–10440 (1995). (Oct., 1995).

Lin et al., "Rhenium–188 hydroxyethylidene diphosphonate: A new generator–produced radiotherapeutic drug of potential value for the treatment of bone metastases" *Eur. J. Nucl. Med.* 24(6):590–595 (1997). (Jun. 1997).

Livak et al., "Detection of single base differences using biotinylated nucleotides with very long linker arms" *Nucl. Acids Res.* 20(18):4831–4837 (1992).

Livingstone, L.R. et al., "Altered cell cycle arrest and gene amplification potential accompany loss of wild–type p53" *Cell* 70:923–935 (1992). (Sep. 18, 1992).

Lönn et al., "Higher frequency of gene amplification in breast cancer patients who received adjuvant chemotherapy" *Cancer* 77(1):107–112 (1996). (Jan. 1, 1996).

Lovejoy et al., "Animal models and the molecular pathology of cancer" *J. Pathol.* 181:130–135 (1997).

Masters et al., "The nucleotide sequence of the cDNA coding for the human dihydrofolic acid reductase" *Gene* 21:59–63 (1983).

McGuigan, "Aryl phosphate derivatives of AZT retain activity HIV1 in cell lines which are resistant to the action of AZT" *Antiviral Res.* 17:311–321 (1992).

McGuigan, "Intracellular delivery of bioactive AZT nucleotides by aryl phosphate derivatives of AZT" *J. Med. Chem.* 36:1048–1052 (1993). (Issue No. 8).

McGuigan et al., "Certain phosphoramidate derivatives of dideoxy uridine (ddU) are active against HIV and successfully by–pass thymidine kinase" *FEBS Let* 351:11–14 (1994).

McGuigan, "Aryl phosphoramidate derivatives of d4T have improved anti–HIV efficacy in tissue culture and may act by the generation of a novel intracellular metabolite" *J. Med. Chem.* 39:1748–1753 (1996). (Issue No. 8).

McGuigan et al., "Synthesis and evaluation of some masked phosphate esters of the anti–herpetic drug 882C (netivudine) as potential antiviral agents" *Antiviral Chem. Chemother.* 9:187–197 (1998).

McIntee, "Probing the mechanism of action and decomposition of amino acid phosphomonoester amidates of antiviral nucleoside prodrugs" *J. Med. Chem.* 40:3323–3331 (1997). (Issue No. 21).

McKay et al., "Broad spectrum aminoglycoside phosphotransferase type III from Enterococcus: Overexpression, purification, and substrate specificity" *Biochem* 33:6936–6944 (1994).(Iss. No. 22).

Meden et al., "Elevated serum levels of a c–erbB–2 oncogene product in ovarian cancer patients and in pregnancy" *J. Can. Res. Clin. Oncol.* 120:378–381 (1994).

Meier et al., "ADA–bypass by lipophilic cyclosal–ddAMP pro–nucleotides a second example of the efficiency of the cyclosal–concept" *Bioorg. Med. Chem. Lett.* 7(12):1577–1582 (1997).

Meier et al., "Cyclic saligenyl phosphotriesters of 2',3'–dideoxy–2',3'–didehydrothymidine (d4T)–a new pro–nucleotide approach" *Bioorg. Med. Chem. Lett.* 7(2):99 (1997).

Meier et al., "CycloSal–pro–nucleotides: The design and biological evaluation of a new class of lipophilic nucleotide prodrugs" *Int'l. Antiviral News* 5(10):183–185 (1997).

Melton et al., "Antibody–enzyme conjugates for cancer therapy" *J. Natl. Can. Inst.* 88(3/4):153–165 (1996). (Feb. 21, 1996).

Montfort et al., "Thymidylate synthase: Structure, inhibition, and strained conformations during catalysis" *Pharmacol. Ther.* 76(1–3):29–43 (1997).

Montgomery et al., "Phosphonate analogue of 2'–deoxy–5–fluorouridylic acid" *J. Med. Chem.* 22(1):109–111 (1979).

Morgan et al., "Tumor efficacy and bone marrow–sparing properties of TER286, a cytotoxin activated by glutathione S–transferase" *Cancer Res.* 58:2568–2575 (1998). (Jun. 15, 1998).

Murakami et al., "Accumulation of genetic alterations and their significance in each primary human cancer and cell line" *Mutat. Res.* 400(1–2):421–437 (1998).

Nakano et al., "Critical role of phenylalanine 34 of human dihydrofolate reductase in substrate and inhibitor binding and in catalysis" *Biochem.* 33:9945–9952 (1994). (Issue No. 33).

Nooter et al., "Molecular mechanisms of multidrug resistance in cancer chemotherapy" *Pathol. Res. Pract.* 192:768–780 (1996).

Osaki et al., "5–fluorouracil (5–FU) induced apoptosis in gastric cancer cell lines: Role of the p53 gene" *Apoptosis* 2:221–226 (1997). (Issue No. 2).

Perry et al. "Plastic adaptation toward mutations in proteins: Structural comparison of thymdiylate synthases" *Proteins* 8:315–333 (1990).

Pestalozzi et al., "Prognostic importance of thymidylate synthase expression in early breast cancer" *J. Clin. Oncol.* 15(5):1923–1931 (1997). (May, 1997).

Peters et al., "Thymidylate synthase and drug resistance" *Eur. J. Can.* 31A(7/8):1299–1305 (1995).

Phelps et al., "Synthesis and biological activity of 5–fluoro–2'–deoxyridine 5'–phosphorodiamidates" *J. Med. Chem.* 23:1229–1232 (1980). (Issue No. 11).

Pupa et al., "The extracellular domain of the c–erbB–2 oncoprotein is released from tumor cells by proteolytic cleavage" *Oncogene* 8:2917–2923 (1993).

Roberts, "An isotopic assay for thymidylate synthetase" *Biochem.* 5(11):3546–3548 (1996).(Nov., 1966).

Robins et al., "Nucleic acid related compounds. 31. Smooth and efficient palladium–copper catalyzed coupling of terminal alkynes with 5–iodouracil nucleosides" *Tetrahedron Lett.* 22:421–424 (1981).

Robins et al., "Nucleic acid related compounds. 38. Smooth and high–yield iodination and chlorination at C–5 of uracil bases and p–toluyl–protected nucleosides" *Can. J. Chem.* 60:554–557 (1982).

Robins et al., "Nucleic acid related compounds. 38. Smooth and high–yield iodination and chlorination at C–5 of uracil bases and p–toluyl–protected nucleosides" *Can. J. Chem.* 60:554–557 (1982).

Robins et al., "Nucleic acid compounds. 39. Efficient conversion of 5–iodo to 5–alkynyl and derived 5–substituted uracil bases and nucleosides" *J. Org. Chem.* 48:1854–1862 (1983). (Iss. No. 11).

Roninson et al., "Amplification of specific DNA sequences correlates with multi–drug resistance in chinese hamster cells" *Nature* 309:626–628 (1984). (Jun. 14, 1984).

Ruth et al., "C–5 sustituted pyrimidine nucleosides. 1. Synthesis of C–5 allyl, propyl, and propenyl uracil and cytosine nucleosides via organopalladium intermediates" *J. Org. Chem.* 43(14):2870–2876 (1978).

Santi, "Perspectives on the design and biochemical pharmacology of inhibitors of thymidylate synthetase" *J. Med. Chem.* 28(2):103–111 (1980). (Feb., 1980).

Sastry et al., "Membrane–permeable dideoxyuridine 5'–monophosphate analogue inhibits human immunodeficiency virus infection" *Mol. Pharmacol.* 41:441–445 (1992).

Sauter et al., "Heterogeneity of erbB–2 gene amplification in bladder cancer" *Cancer Res.* 53:2199–2203 (1993). (May 15, 1993).

Schiffer et al., "Crystal structure of human thymidylate synthase: A structural mechanism for guiding substrates into the active site" *Biochem.* 34:16279–16287 (1995). (Issue No. 50).

Schimke, "Gene amplification in cultured cells" *J. Biol. Chem.* 263(13):5989–5992 (1988).(May 5, 1988).

Segovia, "Leishmania gene amplification: A mechanism of drug resistance" *Annals Tropical Med. Parasitol.* 88(2):123–130 (1994).

Shepard et al., "Resistance of tumor cells to tumor necrosis factor" *J. Clin. Immunol.* 8(5):333–341 (1988).

Simon, "Cell biological mechanisms of multidrug resistance in tumors" *PNAS USA* 91:3497–3504 (1994). (Apr., 1994).

Singh et al., "Studies on the preparation and isomeric composition of $^{186}$Re– and $^{188}$Re–pentavalent rhenium dimercaptosuccinic acid complex" *Nucl. Med. Commun.* 14:197–203 (1993).

Slamon et al., "Human breast cancer: Correlation of relapse and survival with amplification of the HER–2/neu oncogene" *Science* 235:177–182 (1987). (Jan. 9, 1987).

Slamon et al., "Studies of the HER–2/neu proto–oncogene in human breast and ovarian cancer" *Science* 244:707–712 (1989), (May 12, 1989).

Smith et al., "Regulation and mechanisms of gene amplification" *Phil. Trans. Royal Soc. Lond. B* 347:49–56 (1995).

Snydman et al., "Analysis of trends in antimicrobial resistance patterns among clinical isolates of *Bacteroides fragilis* group species from 1990 to 1994" *Clin. Infectious Diseases* 23(Suppl. 1):S54–S65 (1996).

Stout et al., "Structure–based design of inhibitors specific for bacterial thymidylate synthase" *Biochem.* 38:1607–1617 (1999). (Issue No. 5).

Stühlinger et al., "Clinical therapy and HER–2 oncogene amplification in breast cancer: Chemo–vs radiotherapy" *J. Steroid Biochem. Molec. Biol.* 49(1):39–42 (1994).

Sugarman et al., "Recombinant human tumor necrosis factor–α: Effects on proliferation of normal and transformed cells in vitro" *Science* 230(4278):943–945 (1985). (Nov. 22, 1985).

Sukumar et al., "Specific patterns of oncogene activation in transplancentally induced tumors" *PNAS USA* 87:718–722 (1990). (Jan., 1990).

Takeishi et al., "Nucleotide sequence of a functional cDNA for human thymidylate synthase" *Nucl. Acid Res.* 13(6):2035–2043 (1985).

Tannock, "Treatment of cancer with radiation and drugs" *J. Clin. Oncol.* 14(12):3156–3174 (1996).(12/9.

Tennant et al., "Antiviral activity and toxicity of fialuridine in the woodchuck model of hepatitis B virus infection" *Hepatol.* 28:179–191 (1998). (Jul., 1998).

Tolstikov et al., "Synthesis and DNA duplex stabilities of oligonucleotides containing C–5–(3–methoxypropynyl)–2'–deoxyuridine residues" *Nucleosides Nucleotides* 16(3):215–225 (1997).

Troutner, "Chemical and physical properties of radionuclides" *Nucl. Med. Biol.* 14(3):171–176 (1987).

Ubeda et al., "The large subunit of the DNA replication complex C (DSEB/RF–C140) cleaved and inactivated by caspace–3 (CPP32/YAMA) during fas–induced apoptosis" *J. Biol. Chem.* 272(31):19562–19568 (1997). (Aug. 1, 1997).

Valette et al., "Decomposition pathways and in vitro HIV inhibitory effects of isoddA pronucleotides: Toward a rational approach for intracellular delivery of nucleoside 5'–monophosphates" *J. Med. Chem.* 39:1981 (1996). (Issue No. 10).

Van de Vijver et al., "Amplification of the neu (c–erbB–2) oncogene in human mammary tumors is relatively frequent and is often accompanied by amplification of the linked c–erbA oncogene" *Mol. Cell. Biol.* 7(5):2019–2023 (1987). (May, 1987).

Volm et al., "Relationship of inherent resistance to doxorubicin, proliferative activity and expression of P–glycoprotein 170, and glutathione S–transferase–π in human lung tumors" *Cancer* 70(4):764–769 (1992). (Apr. 15, 1992).

Wahba et al., "Direct spectrophotometric evidence for the oxidation of tetrahydrofolate during the enzymatic synthesis of thymidylate" *J. Biol. Chem.* 236(3):C11–C12 (1961). (Mar., 1961).

Wang et al., "Identification and characterization of Ich–3, a member of the interleukin–1β converting enzyme (ICE)/ Ced–3 family and an upstream regulator of ICE" *J. Biol. Chem.* 271(34):20580–20587 (1996). (Aug. 23, 1996).

Wataya et al., "Trans–5–(3,3, 3–trifluoro–1–propenyl)–2'–deoxyuridylate: A mechanism–based inhibitor of thymidylate synthetase" *J. Med. Chem.* 22(4):339–340 (1979). (Apr., 1979).

Wettergren et al., "Drug–specific rearrangements of chromosome 12 in hydroxyurea–resistant mouse SEWA cells: Support for chromosomal breakage model of gene amplification" *Somatic Cell Mol. Genet.* 20(4):267–285 (1994).

Yen et al., "Characterization of a hydroxyurea–resistant human KB cell line with supersensitivity to 6–thioguanine" *Cancer Res.* 54:3686–3691 (1994). (Jul. 15, 1994).

Yin et al., "Wild–type p53 restores cell cycle control and inhibits gene amplification in cells with mutant p53 alleles" *Cell* 70:937–948 (1992). (Sep. 18, 1992).

Zhou et al., "Target protease specificity of the viral serpin CrmA" *J. of Biol. Chem.* 272(12):7797–7800 (1997). (Mar. 21, 1997).

p36 T.S →

ENZYME CATALYZED THERAPEUTIC AGENTS

CROSS REFERENCE TO RELATED APPLICATIONS

This application claims priority under 35 U.S.C. § 119 (e) to U.S. Provisional Application Nos. 60/072,264; 60/076,950; and 60/108,634, filed Jan. 23, 1998; Mar. 05, 1998; and Nov. 16, 1998, respectively. The contents of these applications are hereby incorporated by reference into the present disclosure.

TECHNICAL FIELD

The present invention relates to the field of drug discovery and specifically, the design of prodrugs which are substrates for an intracellular enzyme critical to resistance to therapeutics in pathological cells and converted to a cell toxin by the intracellular enzyme.

BACKGROUND

Throughout and within this disclosure, various publications are referenced by first author and date, patent number or publication number. The full bibliographic citation for each reference can be found within the specification or at the end of this application, immediately preceding the claims. The disclosures of these publications are hereby incorporated by reference into this disclosure to more fully describe the state of the art to which this invention pertains.

Cancer cells are characterized by uncontrolled growth, de-differentiation and genetic instability. The instability expresses itself as aberrant chromosome number, chromosome deletions, rearrangements, loss or duplication beyond the normal diploid number. Wilson, J. D. et al. (1991). This genomic instability may be caused by several number. Wilson, J. D. et al. (1991). This genomic instability may be caused by several factors. One of the best characterized is the enhanced genomic plasticity which occurs upon loss of tumor suppression gene finction (e.g., Ahnasan, A. et al. (1995)). The genomic plasticity lends itself to adaptability of tumor cells to their changing environment, and may allow for the more frequent mutation, amplification of genes, and the formation of extrachromosomal elements (Smith, K. A. et al. (1995) and Wilson, J. D. et al. (1991)). These characteristics provide for mechanisms resulting in more aggressive malignancy because it allows the tumors to rapidly develop resistance to natural host defense mechanisms, biologic therapies (Wilson, J. D. et al. (1991) and Shepard, H. M. et al. (1988)), as well as to chemotherapeutics. (Almasan, A. et al. (1995) and Wilson, J. D. et al. (1991)).

Cancer is one of the most commonly fatal human diseases worldwide. Treatment with anticancer drugs is an option of steadily increasing importance, especially for systemic malignancies or for metastatic cancers which have passed the state of surgical curability. Unfortunately, the subset of human cancer types that are amenable to curative treatment today is still rather small (Haskell, C. M. eds. (1995), p. 32). Progress in the development of drugs that can cure human cancer is slow. The heterogeneity of malignant tumors with respect to their genetics, biology and biochemistry as well as primary or treatment-induced resistance to therapy mitigate against curative treatment. Moreover, many anticancer drugs display only a low degree of selectivity, causing often severe or even life threatening toxic side effects, thus preventing the application of doses high enough to kill all cancer cells. Searching for anti-neoplastic agents with improved selectivity to treatment-resistant pathological, malignant cells remains therefore a central task for drug development. In addition, widespread resistance to antibiotics is becoming an important, world-wide, health issue. (Segovia, M. (1994) and Snydman, D. R. et al. (1996)).

Classes of Chemotherapeutic Agents

The major classes of agents include the alkylating agents, antitumor antibiotics, plant alkaloids, antimetabolites, hormonal agonists and antagonists, and a variety of miscellaneous agents. See Haskell, C. M., ed., (1995) and Dorr, R. T. and Von Hoff, D. D., eds. (1994).

The classic alkylating agents are highly reactive compounds that have the ability to substitute alkyl groups for the hydrogen atoms of certain organic compounds. Alkylation of nucleic acids, primarily DNA, is the critical cytotoxic action for most of these compounds. The damage they cause interferes with DNA replication and RNA transcription. The classic alkylating agents include mechlorethamine, chlorambucil, melphalan, cyclophosphamide, ifosfamide, thiotepa and busulfan. A number of nonclassic alkylating agents also damage DNA and proteins, but through diverse and complex mechanisms, such as methylation or chloroethylation, that differ from the classic alkylators. The nonclassic alkylating agents include dacarbazine, carmustine, lomustine, cisplatin, carboplatin, procarbazine and altretamine.

Many clinically useful antitumor drugs are natural products of various strains of the soil fungus Streptomyces. They produce their tumoricidal effects by one or more mechanisms. All of the antibiotics are capable of binding DNA, usually by intercalation, with subsequent unwinding of the helix. This distortion impairs the ability of the DNA to serve as a template for DNA synthesis, RNA synthesis, or both. These drugs may also damage DNA by the formation of free radicals and the chelation of important metal ions. They may also act as inhibitors of topoisomerase II, an enzyme critical to cell division. Drugs of this class include doxorubicin (Adriamycin), daunorubicin, idarubicin, mitoxantrone, bleomycin, dactinomycin, mitomycin C, plicamycin and streptozocin.

Plants have provided some of the most useful antineoplastic agents. Three groups of agents from this class are the Vinca alkaloids (vincristine and vinblastine), the epipodophyllotoxins (etoposide and teniposide) and paclitaxel (Taxol). The Vinca alkaloids bind to microtubular proteins found in dividing cells and the nervous system. This binding alters the dynamics of tubulin addition and loss at the ends of mitotic spindles, resulting ultimately in mitotic arrest. Similar proteins make up an important part of nervous tissue; therefore, these agents are neurotoxic. The epipodophyllotoxins inhibit topoisomerase II and therefore have profound effects on cell function. Paclitaxel has complex effects on microtubules.

The antimetabolites are structural analogs of normal metabolites that are required for cell function and replication. They typically work by interacting with cellular enzymes. Among the many antimetabolites that have been developed and clinically tested are methotrexate, 5-fluorouracil (5-FU), floxuridine (FUDR), cytarabine, 6-mercaptopurine (6-MP), 6-thioguanine, deoxycoformycin, fludarabine, 2-chlorodeoxyadenosine, and hydroxyurea.

Endocrine manipulation is an effective therapy for several forms of neoplastic disease. A wide variety of hormones and hormone antagonists have been developed for potential use in oncology. Examples of available hormonal agents are diethylstilbestrol, tamoxifen, megestrol acetate, dexamethasone, prednisone, aminoglutethimide, leuprolide, goserelin, flutamide, and octreotide acetate.

Drawbacks of Current Chemotherapeutic Agents

Among the problems currently associated with the use of chemotherapeutic agents to treat cancers are the high doses of agent required; toxicity toward normal cells, i.e., lack of selectivity; immunosuppression; second malignancies; and drug resistance.

The majority of the agents that are now used in cancer chemotherapy act by an anti-proliferative mechanism. Toxicity results because many normal cell types (e.g., colon epithelium, hematopoietic cells) have a high proliferative rate. Because of host toxicity, treatment has to be discontinued at dose levels that are well below the dose that would be required to kill all viable tumor cells.

Another side effect associated with present day therapies is the toxic effect of the chemotherapeutic on the normal host tissues that are the most rapidly dividing, such as the bone marrow, gut mucosa and cells of the lymphoid system. The agents also exert a variety of other adverse effects, including neurotoxicity; negative effects on sexuality and gonadal function; and cardiac, pulmonary, pancreatic and hepatic toxicities; vascular and hypersensitivity reactions, and dermatological reactions.

TABLE 1

Normal and Tumor Breast Epithelial Cells Are Equally Sensitive to Doxorubicin Chemotherapy

| Cell or Tissue | Number of Samples | Average $IC_{50}$ |
|---|---|---|
| Normal Breast | 13 | 14.8 ± 8.7 ng/ml |
| Primary Carcinoma (UT) | 19 | 11.4 ± 6.8 ng/ml |
| Metastatic Carcinoma (UT) | 4 | 36 ± 26.3 ng/ml |
| Metastatic Carcinoma (Rx) | 10 | 19.8 ± 12.7 ng/ml |

From Smith et al. JNCl 74:341–347 (1985).

Hematologic toxicity is the most dangerous form of toxicity for many of the antineoplastic drugs used in clinical practice. Its most common form is neutropenia, with an attendant high risk of infection, although thrombocytopenia and bleeding may also occur and be life threatening. Chemotherapy may also induce qualitative defects in the function of both polymorphonuclear leukocytes and platelets. The hematopoietic growth factors have been developed to address these important side effects. Wilson, J. D. et al. (1991) and Dorr, R. T. and Von Hoff, D. D., eds. (1994).

Most of the commonly used antineoplastic agents are capable of suppressing both cellular and humoral immunity. Infections commonly lead to the death of patients with advanced cancer, and impaired immunity may contribute to such deaths. Chronic, delayed immunosuppression may also result from cancer chemotherapy.

The major forms of neurotoxicity are arachnoiditis; myelopathy or encephalomyelopathy; chronic encephalopathies and the somnolence syndrome; acute encephalopathies; peripheral neuropathies; and acute cerebellar syndromes or ataxia.

Many of the commonly employed antineoplastic agents are mutagenic as well as teratogenic. Some, including procarbazine and the alkylating agents, are clearly carcinogenic. This carcinogenic potential is primarily seen as delayed acute leukemia in patients treated with polyfunctional alkylating agents and inhibitors of topoisomerase II, such as etoposide and the anthracycline antibiotics. Chemotherapy has also been associated with cases of delayed non-Hodgkin's lymphoma and solid tumors. The present invention will minimize these effects since the prodrug will only be activated within tumor cells.

The clinical usefulness of a chemotherapeutic agent may be severely limited by the emergence of malignant cells resistant to that drug. A number of cellular mechanisms are probably involved in drug resistance, e.g., altered metabolism of the drugs, impermeability of the cell to the active compound or accelerated drug elimination from the cell, altered specificity of an inhibited enzyme, increased production of a target molecule, increased repair of cytotoxic lesions, or the bypassing of an inhibited reaction by alternative biochemical pathways. In some cases, resistance to one drug may confer resistance to other, biochemically distinct drugs. An alternative mechanism of resistance to cancer, chemotherapeutics occurs via the functional loss of tumor suppressor genes, especially p53, RB and p16. Loss of function of these gene products leads to derepressed expression of enzymes commonly targeted by anti-cancer drugs (e.g., 5FU/thymidylate synthase and methotrexate/dihydrofolate reductase). (Lee, V. et al. (1997), Exp. Cell Res. 234:270–6; Lenz, H. J. et al. (1998), Clinical Cancer Res. 4:1227–34 (1998), Fan, J. and Bertino, J. (1987), Oncogene 14:1191–200). Amplification of certain genes is involved in resistance to biologic and chemotherapy. Amplification of the gene encoding dihydrofolate reductase is related to resistance to methotrexate, while overexpression/amplification of the gene encoding thymidylate synthase is related to resistance to treatment with 5-fluoropyrimidines. Smith (1995). Table 2 summarizes some prominent enzymes in resistance to biologic and chemotherapy.

TABLE 2

Enzymes Overexpressed in Resistance to Cancer Chemotherapy

| Enzyme | Biologic or Chemotherapy | Referenced (Examples) |
|---|---|---|
| Thymidylate synthase | Uracil-based Folate-based Quinazoline-based | Lönn, U. et al. Cancer 77:107, 1996 Kobayashi, H. et al. Jpn. J. Cancer Res. 86:1014, 1995 Jackman, AL et al. Anticancer Drug Des. 10:573, 1995 |
| Dihydrofolate reductase | Folate-based | Banerjee, D. et al. Acta Biochem Pol. 42:457, 1995 Bertino, J. R. et al. Stem Cells 14:5, 1996 |
| Tyrosine kinases | TNF-alpha Multidrug resistance | Hudziak, R. M. et al. PNAS 85:5102, 1988 Stühlinger, M. et al. J. Steroid Biochem 49:39, 1994 |
| MDR-associated proteins (ABC P-gp proteins) | Multidrug resistance | Simon, S. M. and Schindler, M. PNAS 91:3497, 1994 Gottesman, M. M. et al. Annu. Rev. Genet. 29:607, 1995 |
| CAD* | PALLA** | Smith, K. A. et. al. Philos. Trans. R. Soc. Lon. B. Biol. Sci. 347:49, 1995 Dorr, R. T. and Von Hoff, D. D., eds. "Cancer Chemotherapy Handbook" 2nd ed. (Appleton and Lange 1994), pp. 768–773 |
| Topoisomerase I (Colon & Prostate Cancers) | Camptothecin | Husain et al. Cancer Res. 54:539, 1994 |
| Ribonucleotide reductase | Hydroxyurea | Wettergren, Y. et al. Mol. Genet. 20:267–85, 1994 Yen, Y. et al. Cancer Res. 54:3686–91, 1994 |

*CAD = carbamyl-P synthase, aspartate transcarbamylase, dihydroorotase
**PALA = N-(phosphonacetyl)-L-aspartate Use of Prodrugs as a Solution to Enhance Selectivity of a Chemotherapeutic Agent The poor selectivity of anticancer agents has been recognized for a long time and attempts to improve selectivity and allow greater doses to be administered have been numerous. One approach has been the development of prodrugs. Prodrugs are compounds that are toxicologically benign but which may be converted in vivo to therapeutically active products. In some cases, the activation occurs through the action of a non-endogenous enzyme delivered to the target cell by antibody ("ADEPT" or antibody-dependent enzyme prodrug therapy (U.S. Pat. No. 4,975,278)) or gene targeting ("GDEPT" or gene dependent enzyme-prodrug therapy (Melton, R. G. and Sherwood, R. F. (1996)). These technologies have severe limitations with respect to their ability to exit the blood and penetrate tumors. Connors, T. A. and Knox, R. J. (1995).

Accordingly, there is a need for more selective agents which can penetrate the tumor and inhibit the proliferation and/or kill cancer cells that have developed resistance to therapy. The present invention satisfies this need and provides related advantages as well.

SUMMARY OF THE INVENTION

This invention provides a method for identifying potential therapeutic agents by contacting a target or test cell with a candidate therapeutic agent or prodrug which is a selective substrate for a target enzyme in the cell. This new approach is named "ECTA", for Enzyme Catalyzed Therapeutic Agents. In one embodiment, the target enzyme is an endogenous, intracellular enzyme which is overexpressed and confers resistance to biologic and chemotherapeutic agents. In a separate embodinent, the activity of the enzyme has been greatly enhanced in a tumor cell as a result of loss of tumor suppressor finction (Smith, K. A. et al. (1995) and Li, W. et al. (1995)) and/or selection resulting from previous exposure to chemotherapy, (Melton, R. G. and Sherwood, R. F. (1996) and Lonn, U. et al. (1996)). In a separate embodiment, the target enzyme is an expression product of an infectious agent in the cell.

After the cell is contacted in vitro and/or in vivo with the candidate prodrug, the cell is assayed for efficacy of the agent by noting if the agent caused a reduction in cellular proliferation or if the agent kills the cell. In one aspect of this invention, the prodrug kills the cell or inhibits the cellular proliferation by the release of a toxic byproduct from the prodrug by the target enzyme. In a further aspect of this invention, one or more "target enzymes" can be used to activate the prodrug so that it releases the toxic byproduct.

Another aspect of this invention includes kits for use in assaying for new prodrugs having the characteristics described herein against target enzymes. The kits comprise the reagents and instructions necessary to complete the assay and analyze the results.

This invention also provides methods and examples of molecules for selectively killing a pathological cell by contacting the cell with a prodrug that is a selective substrate for a target enzyme, e.g., an endogenous, intracellular enzyme as defined above. The substrate is specifically converted to a cellular toxin by the intracellular target enzyme. In another aspect of this invention, the product of an initial reaction is subsequently fully activated by a common cellular enzyme such as an acylase, phosphatase or other "housekeeping" enzyme (Voet, et al. (1995)) or common cellular constituent (e.g., water) to release the toxic byproduct from the prodrug.

Further provided by this invention is a method for treating a pathology characterized by pathological, hyperproliferative cells in a subject by administering to the subject a prodrug that is a selective substrate for a target enzyme, and selectively converted by the enzyme to a cellular toxin in the hyperproliferative cell. The prodrugs of this invention may be used alone or in combination with other chemotherapeutics or alternative anti-cancer therapies such as radiation.

A further aspect of this invention is the preparation of a medicament for use in treating a pathology characterized by pathological, hyperproliferative cells in a subject by administering to the subject a prodrug that is a selective substrate for a target enzyme, and selectively converted by the enzyme to a cellular toxin in the hyperproliferative cell.

A still further aspect of this invention is a method for identifying the optimal therapeutic for a subject, by isolating cells overexpressing an endogenous, intracellular enzyme and contacting the cells with at least one of the prodrugs of this invention, and then identifying which of the one or more prodrugs inhibits the proliferation or kills the cells, thereby indentifying the optimal therapeutic for the subject.

Figure 1:
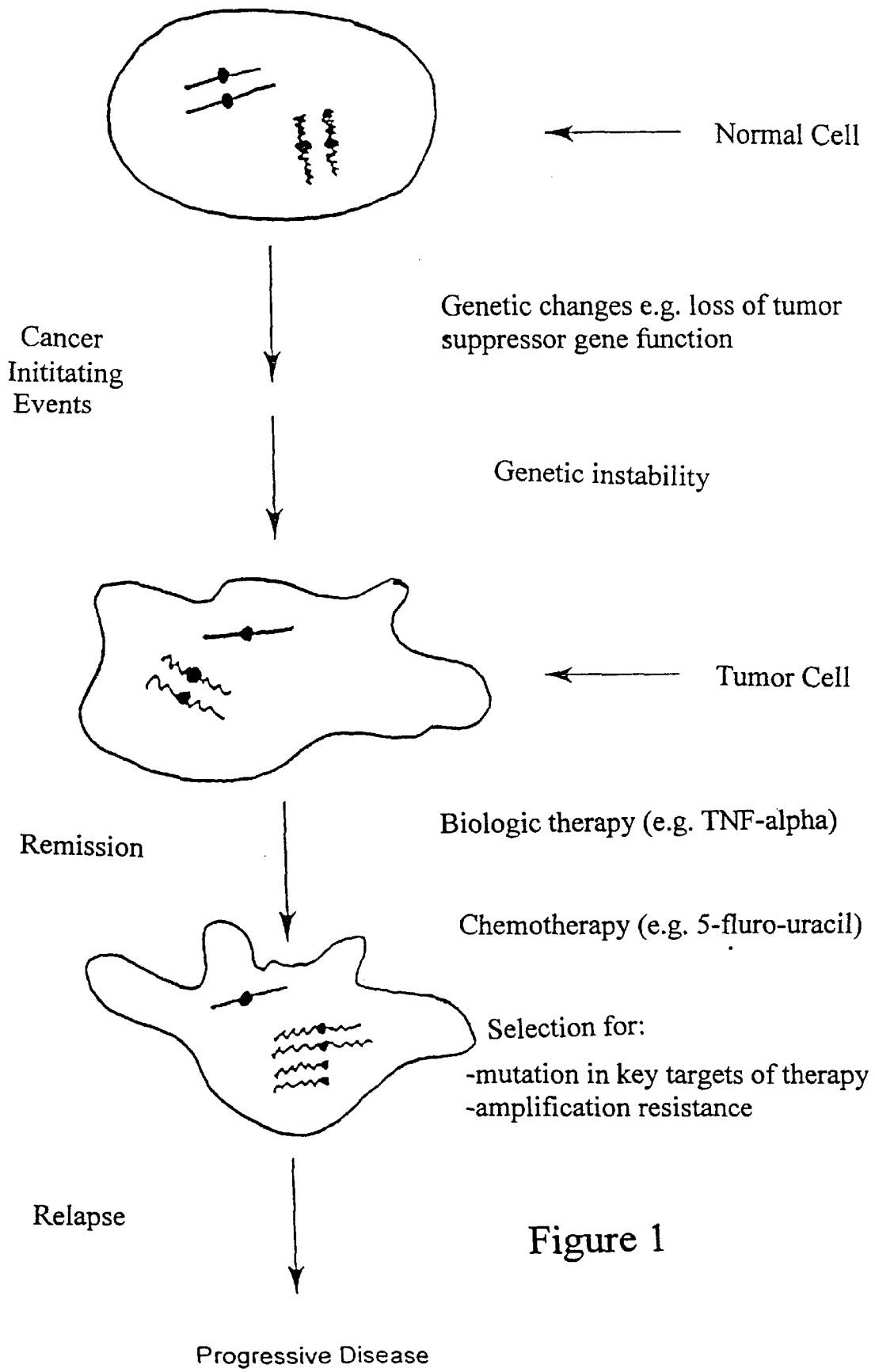
FIG. 1 shows the development of resistance to anti-cancer modalities in cells, and the consequences.
Figure 2:
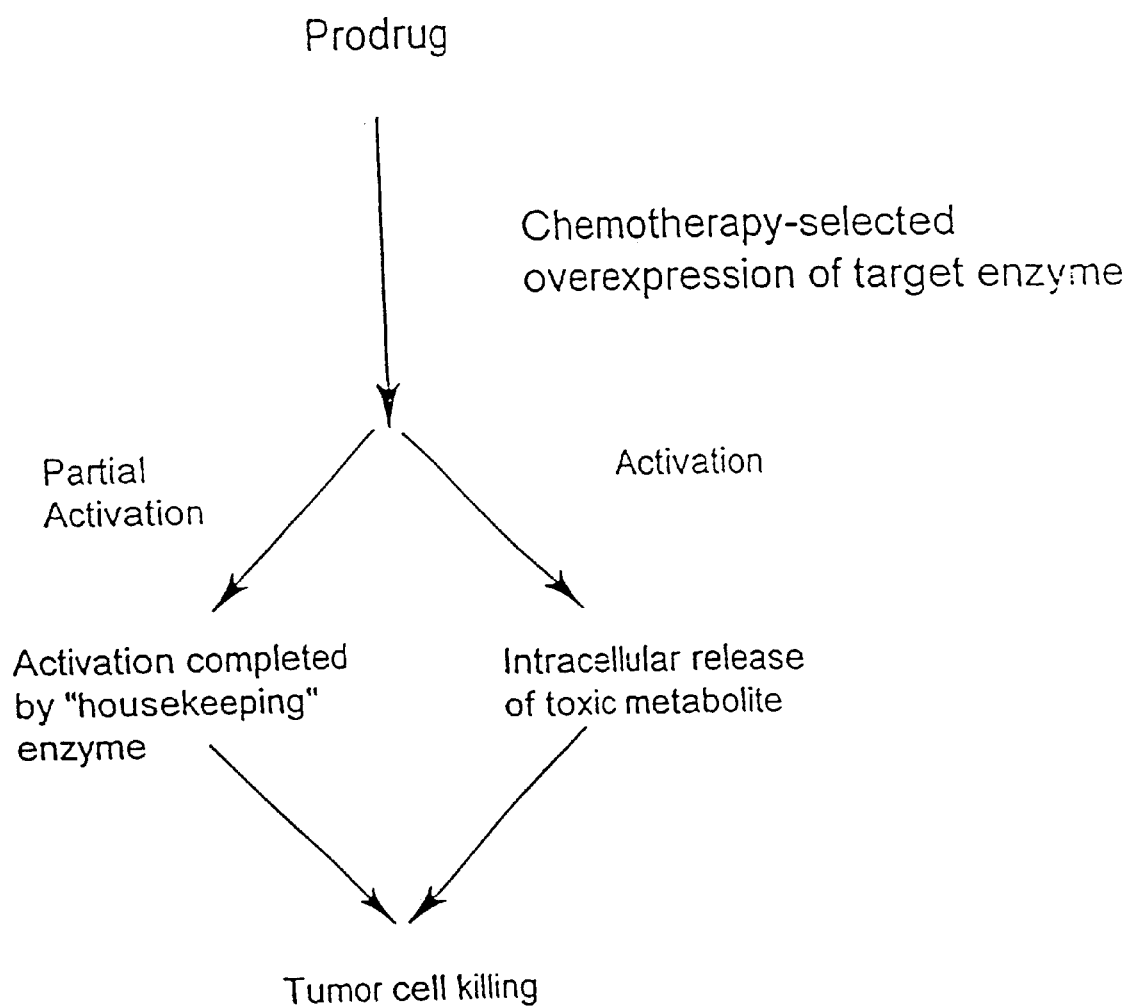
FIG. 2 schematically shows activation pathways of the prodrugs of this invention.

Box 1 represents a masked or absent phosphate group $R^7$. When masked, it is a phosphoramidate or similar derivative that facilitates cell entry and is processed intracellularly to a monophosphate which can bind to TS. See Fries, K. M. et al. (1995). When absent, $R^7$ is a hydrogen atom and the prodrug is a substrate for cellular thymidine kinase (TK), which generates the requisite monophosphate in vivo.

Box 2 is a 2'-deoxyribofuranose group or other similar sugar, thio-sugar, carbocyclic, or acyclic group which connects the monophosphate to the pyrimidine ring in a manner that supports functional binding of the prodrug to TS and, when $R^7$ is a hydrogen atom, to TK. This group need not utilize an oxygen atom for attachment to the $R^7$ group of box 1. Thus, phosphonate analogs of sugar phosphates are acceptable.

Box 3 represents a tether group, wherein n is an integer from 0 to 10, that is a mono- or polyunsaturated electron conduit acting to conduct electrons away from the pyrimidine ring and toward the leaving group $R^4$ when the prodrug is acted upon by TS. The tether group is comprised of 0 to 10 unsaturated moieties like acyclic vinyl, ethynyl, imine, or azo units or cyclic unsaturated, aromatic, or heteroaromatic ones that can be mixed and matched at will as long as their connectivity provides the requisite electron-conducting conduit.

Box 4 represents a spacer unit X, wherein m is an integer from 0 to 1, that connects the tether to the leaving group $R^4$. If Box 3, n equals 0, then Box 4, m equals 1. In the preferred form, X is a methylene (CH$_2$) unit, either bearing substituents or not. Additionally, though, X can be an oxygen, sulfur, nitrogen, or other atoms capable of forming at least two covalent bonds. When X is absent (Box 4, m equals 0), the departure of the leaving group R$^4$ during the processing of the prodrug by TS leaves behind a pyrimidine nucleotide-based alkylating entity. See Barr, et al. (1983). When X is present (Box 4, m equals 1), the departure of the leaving group R$^4$ occurs early during the processing of the prodrug by TS.

Box 5 represents a leaving group R$^4$ that is released by the action of TS on the prodrug. It is itself a toxic antimetabolite or alkylating agent or is an entity that readily produces a toxic antimetabolite or alkylating agent in vivo. For example, the leaving group R$^4$ can depart as an active metabolite of the anticancer agents Tepa or Thiotepa, a phosphoramide mustard, N-acetylsphingosine (C$_2$ ceramide, a tumor suppressor lipid) or hydroxyurea (an inhibitor of ribonucleotide reductase) upon release by TS. The leaving group R$_1$ can also be an α,α-dihalogenated ether, in which case it affords a carboxylic acid group when the α,α-dihalogenated alcohol released by TS undergoes hydrolysis. Thus, the leaving group R$^4$ can depart as a progenitor to fluoroacetate, fluorocitrate, malonic acid, methylmalonic avid, or 3-nitroproprionic acid, all potent inhibitors of oxidative phosphorylation.

Figure 7:
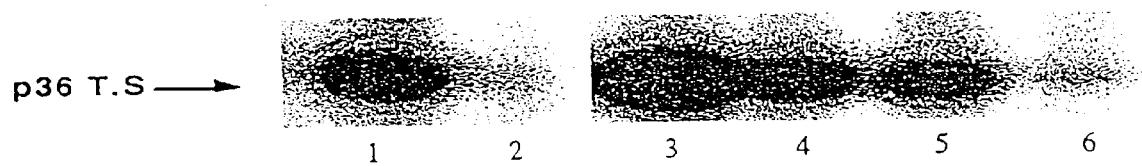

FIG. 7 shows TS Western blot of cell lines transfected by plasmid encoding neomycin resistance, with or without the HER-2 protooncogene. Lane (1) MCF7/HER2; (2) MCF7/neo; (3) MDA-MB-435/HER2; (4) MDA-NM-435/neo; (5) BT-20/HER2; (6) BT-20/neo.

Figure 8:
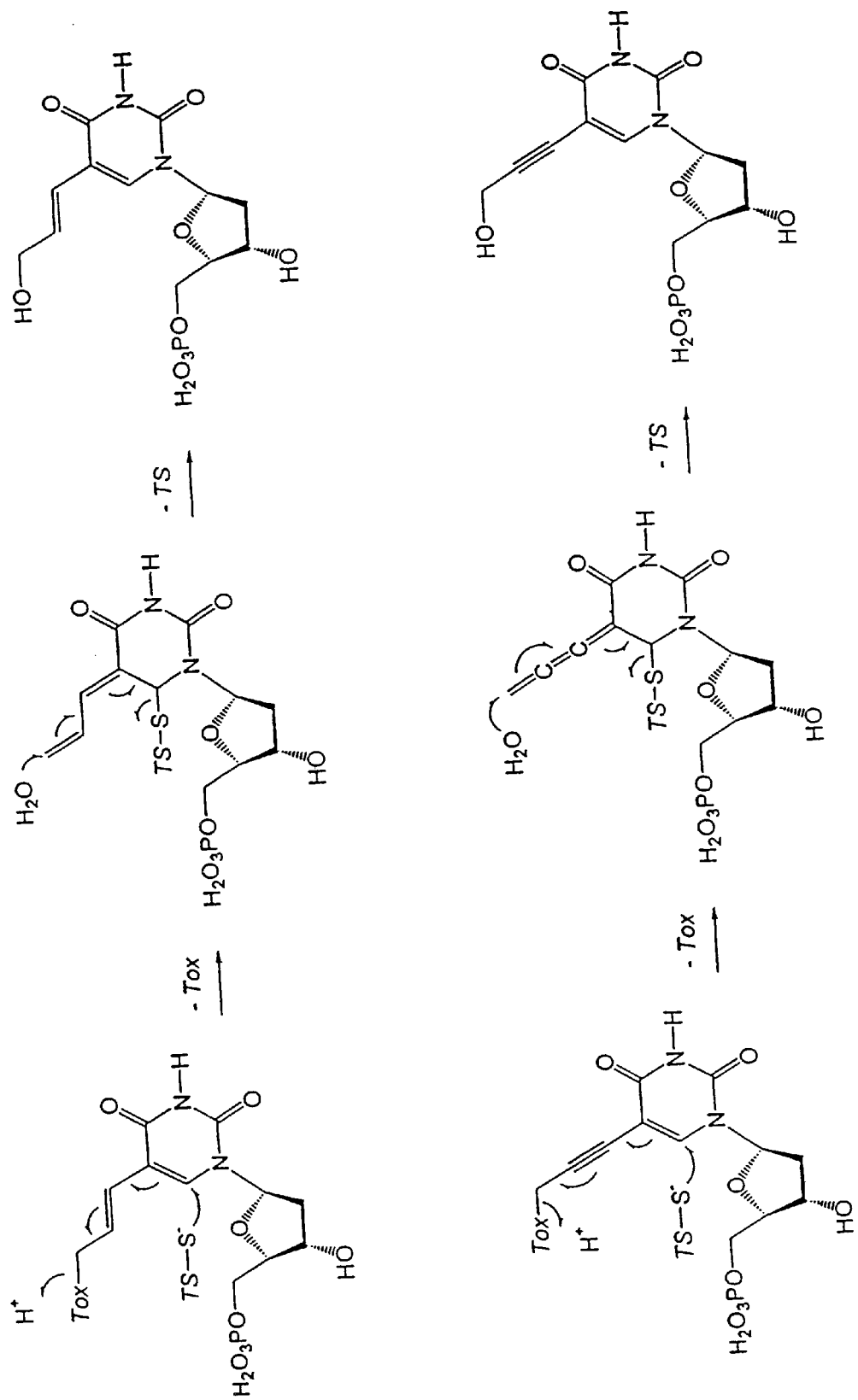

FIG. 8 shows reaction products of prodrug compounds with the enzyme thymidylate synthase.

DETAILED DESCRIPTION OF THE INVENTION

The invention is achieved by exploiting some of the key genomic and phenotypic changes intimately linked to resistance to biologic and chemotherapy of cancer cells. The invention provides a means for in vivo selectively inhibiting the growth and/or killing of cells which have undergone selection by exposure to cancer therapy (including biologic therapy such as tumor necrosis factor (TNF) or chemotherapy). (Refer to Table 2). As a result, certain enzymes which have been activated by mutation or gene amplification are resistant to initial or further therapy by the agent. Unlike prior art therapies directed to creating more potent inhibitors of endogenous, intracellular enzymes, this invention exploits the higher enzyme activity associated with therapy-resistant diseased cells and tissues versus normal cells and tissues and does not rely on inhibiting the enzyme. In one aspect, the tumor cells successfully treated by the prodrugs of this invention are characterized by enhanced target enzyme activity and therefore have a much higher potential to convert the prodrug to its toxic form than do normal cells which do not overexpress the target enzyme. The term "target enzyme" is used herein to define enzymes having one or more of the above noted characteristics.

The practice of the present invention will employ, unless otherwise indicated, conventional techniques of molecular biology, microbiology, cell biology and recombinant DNA, which are within the skill of the art. See, e.g., Sambrook, Fritsch and Maniatis, MOLECULAR CLONING: A LABORATORY MANUAL, 2$^{nd}$ edition (1989); CURRENT PROTOCOLS IN MOLECULAR BIOLOGY (F. M. Ausubel et al. eds., (1987)); the series METHODS IN ENZYMOLOGY (Academic Press, Inc.): PCR 2: A PRACTICAL APPROACH (M. J. MacPherson, B. D. Hames and G. R. Taylor eds. (1995)) and ANIMAL CELL CULTURE (R. I. Freshney, ed. (1987)).

As used in the specification and claims, the singular form "a", "an" and "the" include plural references unless the context clearly dictates otherwise. For example, the term "a cell" includes a plurality of cells, including mixtures thereof An "effective amount" is an amount sufficient to effect beneficial or desired results. An effective amount can be administered in one or more administrations, applications or dosages.

As used herein, the terms "host cells, "target cells" and "hyperproliferative cells" encompass cells characterized by the activation by genetic mutation or the endogenous overexpression of an intracellular enzyme. In some embodiments, the overexpression of the enzyme is related to loss of tumor suppressor gene product function drug resistance or the genetic instability associated with a pathological phenotype. A number of cellular mechanisms are involved in drug resistance, e.g., altered metabolism of the drug, impermeabilty of the cell with regard to the active compound or accelerated drug elimination from the cell, altered specificity of an inhibited enzyme, increased production of a target molecule, increased repair of cytotoxic lesions, or the bypassing of an inhibited reaction by alternative biochemical pathways. Enzymes activated or overexpressed and related to drug resistance include, but are not limited to thymidylate synthase (TS) (Lönn, U. et al. (1996); Kobayashi, H. et al. (1995); Jackman, A. L. et al. (1995)), dihydrofolate reductase (Banerjee, D. et al. (1995) and Bertino, J. R. et al. (1996)), tyrosine kinases (TNF-α, Hudziak, R. M. et al. (1988)) and multidrug resistance (St ühlinger, M. et al. (1994)); Akdas, A. et al. (1996); and (Tannock, I. F. (1996)); and ATP-dependent multidrug resistance associated proteins (Simon, S. M. and Schindler, M. (1994)) and, in some diseases including colon and prostate cancer, topoisomerase I (Husain et al. (1994)). Alternatively, resistance to one drug may confer resistance to other, biochemically distinct drugs. While this application is specifically directed to cancer, a similar approach can be applied to enzymes encoded by human and animal pathogens, and in which the inhibitors have failed due to development of resistance.

Amplification of certain genes is involved in resistance to chemotherapy. Amplification of dihydrofolate reductase (DHFR) is related to resistance to methotrexate while amplification of the gene encoding thymidylate synthase is related to resistance to tumor treatment with 5-fluoropyrimidines. Amplification of genes associated with drug resistance can be detected and monitored by a modified polymerase chain reaction (PCR) as described in Kashini-Sabet, et al. (1988), U.S. Pat. No. 5,085,983, or the method described herein. Acquired drug resistance can be monitored by the detection of cytogenetic abnormalities, such as homogeneous chromosome staining regions and double minute chromosomes both of which are associated with gene amplification. Alternative assays include direct or indirect enzyme activity assays and both of which are associated with gene amplification (e.g., Carreras & Santi (1995)); other methodologies (e.g. polymerase chain reaction, Houze, T. A. et al. (1997) or immunohistochemistry (Johnson, P. G. et al. (1997)).

Alternatively, the target cell is characterized as having inactivated tumor suppressor function, e.g. loss or inactivation of retinoblastoma (RB) or p53, known to enhance expression of TS (Li, W. et al. (1995)) or DHFR (Bertino, et al. (1996) and Li, W. et al. (1995)).

The prodrugs of this invention are useful to treat or ameliorate any disease wherein the disease-associated enzyme is associated with drug resistance to a chemotherapeutic whether due to loss of tumor suppressor functionality, in vivo selection by chemotherapy or a combination. This includes embodiments, where the enzyme is overexpressed, over-accumulated or activated in pathological cells versus normal cells, for example, the TS enzyme. Particularly excluded is the enzyme glutathione-S-transferase which has been shown to be occasionally elevated in some human tumors. Morgan, A. S. et al. (1998). The prodrugs of the subject invention are distinguishable on the basis that the target enzymes of this invention are commonly overexpressed, overaccumulated or activated in pathological cells versus normal cells. The most important principle which distinguishes the current invention from other approaches are:

(1) This invention describes the synthesis of substrates for enzymes like thymidylate synthase. The overexpressed enzyme will generate toxin, preferentially in diseased cells. Previous approaches have relied on an inhibitor. The inhibitors lead to amplified expression of the enzyme, and subsequent resistance to treatment (see, e.g., Lonn, U. et al. (1996).

(2) The current approach is also distinguishable from other "substrate-prodrug" approaches, e.g., the glutathione-S-transferase enzymes (see, e.g., Morgan, A. S. et al. (1998). The enzymes of the GST family are expressed at increased levels in response to toxic insult to the cell. The GST family of enzymes have overlapping substrate specificities, which makes it difficult to design a substrate reactive with only a single species of enzyme with elevated expression in a cancer cell (Morgan, A. S. et al. (1998)). Because each of the enzymes of the current invention (e.g., thymidylate synthase, dihydrofolate reductase and thymidine kinase) is unique with respect to its structure and substrate specificity, it is facile to design unique substrates. Several examples of substrates for thymidylate synthase are provided in the specifications of this application.

(3) In some cases the gene encoding the target enzyme (e.g., thymidylate synthase) may have undergone mutation to give resistance to inhibitors, (Barbour, K. W. et al. (1992) and Dicken, A. P. et al. (1993)) but will still be capable of carrying out reaction with non-inhibitor substrate prodrugs.

(4) A further advantage of this approach is that loss of tumor suppressor function is critical to development of malignancy. The majority of tumor cells have lost one of the p53, RB or p16 tumor suppressor fimctions. Such a loss results in increased expression of resistance enzymes (e.g, Thymidylate synthase), independent of previous exposure to chemotherapy. The prodrugs described herein will be useful in treating early stages of malignancy, as well as disease previously treated with chemotherapy. Substrates for enzymes like GST require previous exposure of the tumor to chemotherapy in order to achieve sufficient overexpression to offer even the possibility of a modest therapeutic index.

Drug Assay

This invention provides a method for identifying agents which have therapeutic potential for the treatment of hyperproliferative or neoplastic disorders, e.g., cancer. The method also identifies agents that inhibit the growth of cells or cell cycling of hyperproliferative cells, such as cancer cells. Other cells that are included are bacterial, yeast and parasitic cells which cause disease as a result of inappropriate proliferation in the patient The agent is considered a potential therapeutic agent if cell proliferation, replication or cell cycling is reduced relative to the cells in a control sample. Most preferably, the cells are killed by the agent. The cells can be procaryotic (bacterial such as *E. coli*) or eucaryotic. The cells can be mammalian or non-mammalian cells, e.g., mouse cells, rat cells, human cells, fingi (e.g., yeast) or parasites (e.g., Pneumocystis or Leishmania) which cause disease.

As used herein, a "hyperproliferative cell" is intended to include cells that are de-differentiated, immortalized, neoplastic, malignant, metastatic or transformed. Examples of such cells include, but are not limited to a sarcoma cell, a leukemia cell, a carcinoma cell, or an adenocarcinoma cell. More specifically, the cell can be a breast cancer cell, a hepatoma cell, a dectectable cancer cell, pancreatic carcinoma cell, an oesophageal carcinoma cell, a bladder cancer cell, an ovarian cancer cell, a skin cancer cell, a liver carcinoma cell, or a gastric cancer cell. In an alternative embodiment, the target cell can be resistant to a drug or compound used to prevent or kill a cell infected with an infectious agent which is resistant to coventional antibiotics. Infectious agents include bacteria, yeast and parasites, such as trypanosomes.

Specific examples of target enzymes that are the subject matter of this invention are listed in Table 2 (above) or Table 3 (below). These enzymes are involved in resistance to chemotherapy, are endogeneously activated, overexpressed or over-accumulated in a cell characterized by resistance to cancer therapy and associated with a pathological or disease include, but are not limited to enzymes such as a member of the tyrosine kinase superfamily or an ATP-dependent MDR-associated protein, CAD, thymidylate synthase, dihydrofolate reductase, and ribonucleotide reductase. Table 3 provides a list of enzymes which may be targeted by this approach in infectious disease.

TABLE 3

Enzymes Overexpressed in Infectious Disease, and which Contribute to Drug Resistance

| Enzyme | Provides increased Resistance to: |
| --- | --- |
| Beta-lactamases | Penicillin and other beta-lactam containing antibiotics |
| Aminoglycosidase, or aminoglycoside midifying enzymes | Aminoglycoside antibiotics (e.g., streptomycin, gentamycin) |
| Chloramphenicol transacetylase | Chloramphenicol |
| Dihydrofolate reductase | Trimethoprim |

Reference: Mechanisms of Microbial Disease, 2nd Ed., M. Schaechter, G. Medloff, B. I. Eisenstein, Editor TS Satterfield. Publ. Williams and Wilkins, pp. 973 (1993).

The potentially therapeutic agent identified by the method of this invention is a prodrug that is a substrate for the enzyme and is converted intracellularly to an intracellular toxin. As used herein, a "prodrug" is a precursor or derivative form of a pharmaceutically active agent or substance that is less cytotoxic to target or hyperproliferative cells as compared to the drug metabolite and is capable of being enzymatically activated or converted into the more active form (see Connors, T. A. (1986) and Connors, T. A. (1996)). The toxicity of the agent is directed to cells that are producing the converting enzyme in an amount effective to produce a therapeutic concentration of the cellular toxin in the diseased cell.

Figure 3:
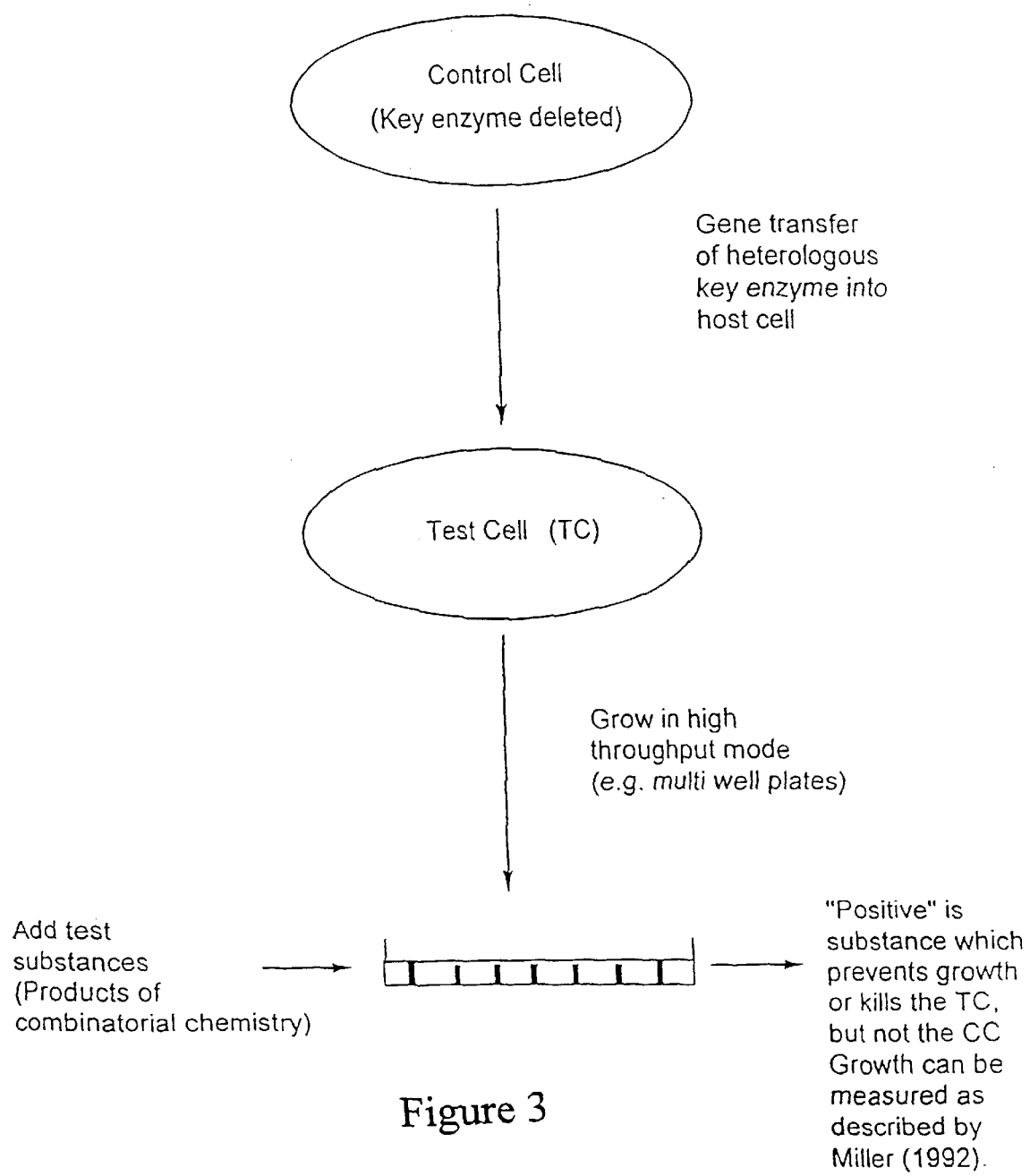
FIG. 3 schematically shows the High Throughput Screen for prodrugs activated by intracellular enzymes important in drug resistance.

This invention also provides a quick and simple screening assay that will enable initial identification of compounds with at least some of the desired characteristics. For purposes of this current invention, the general scheme of one embodiment is shown in FIG. 3. This drawing describes how the assay is arranged and the materials necessary for its process. As shown in FIG. 3, the assay requires two cell types, the first being a control cell in which the target enzyme is not expressed, or is expressed at a low level. The second cell type is the test cell, in which the target enzyme is expressed at a detectable level, e.g., a high level For example, a procaryotic E. coli which does not endogenously express the target enzyme TS is a suitable host cell or target cell. The cell can have a control counterpart (lacking the target enzyme), or in a separate embodiment, a counterpart genetically modified to differentially express the target enzyme, or enzymes (containing the appropriate species of target enzyme). More than one species of enzyme can be used to separately transduce separate host cells, so that the effect of the candidate drug on a target enzyme can be simultaneously compared to its effect on another enzyme or a corresponding enzyme from another species.

In another embodiment, a third target cell is used as a control because it receives an effective amount of a compound, such as, for example, the compounds shown below, which have been shown to be potent prodrugs. This embodiment is particularly useful to screen for new agents that are activated by thymidylate syntase.

In another embodiment, transformed cell lines, such as ras-transformed NIH 3T3 cells (ATCC, 10801 University Blvd., Manassas, Va. 20110-2209, U.S.A.) are engineered to express variable and increasing quantities of the target enzyme of interest from cloned cDNA coding for the enzyme. Transfection is either transient or permanent using procedures well known in the art and described in Chen, L. et al. (1996), Hudziak, R. M. et al. (1988), or Carter, P. et al. (1992), and in the experimental section below. Suitable vectors for insertion of the cDNA are commercially available from Stratagene, La Jolla, Calif. and other vendors. The level of expression of enzyme in each transfected cell line can be monitored by immunoblot and enzyme assay in cell lysates, using monoclonal or polyclonal antibody previously raised against the enzyme for immuno-detection. See, e.g., as described by Chen, L. et al. (1996). The amount of expression can be regulated by the number of copies of the expression cassette introduced into the cell or by varying promoter usage. Enzymatic assays to detect the amount of expressed enzyme also can be performed as reviewed by Carreras, C. W. and Santi, D. V. (1995), or the method described in the experimental section below. Tumor cell lines can be selected to express enhanced levels of thymidylate synthase (e.g., colon tumor cells, as described by Copur et al. (1995).

As noted above, cells containing the desired genetic deficiencies may be obtained from Cold Spring Harbor, the Agricultural Research Service Culture Collection, or the American Type Culture Collection. The appropriate strins can also be prepared by inserting into the cell a gene coding for the target enzyme using standard techniques as described in Miller (1992), Sambrook, et al. (1989), and Spector et al. (1998). Growth assays can be performed by standard methods as described by Miller (1992), Sugarman et al. (1985) and Spector et al. (1998).

It should be understood by those skilled in the art that the screen shown in FIG. 3 can be applied broadly for the discovery of antibiotics. For example, thymidylate synthase from yeast could be substituted for that of E. coli in FIG. 4. This would allow the discovery of specific antifungal antibiotics targeting yeast related pathogens. In addition, other enzymes can be subjected to this treatment. For example, prodrugs which target specifically the dihydrofolate reductase activity of infectious agents, like Pneumocystis carnii, could be selected. These agents will be selected for specificity for the target enzyme, and can be shown not to activate the enzyme of the natural host by employing the screening assay described in FIG. 3. The control cellular constructs would contain the corresponding normal human enzyme, in order to show lack of toxicity when only the normal human enzyme is present.

Figure 4:
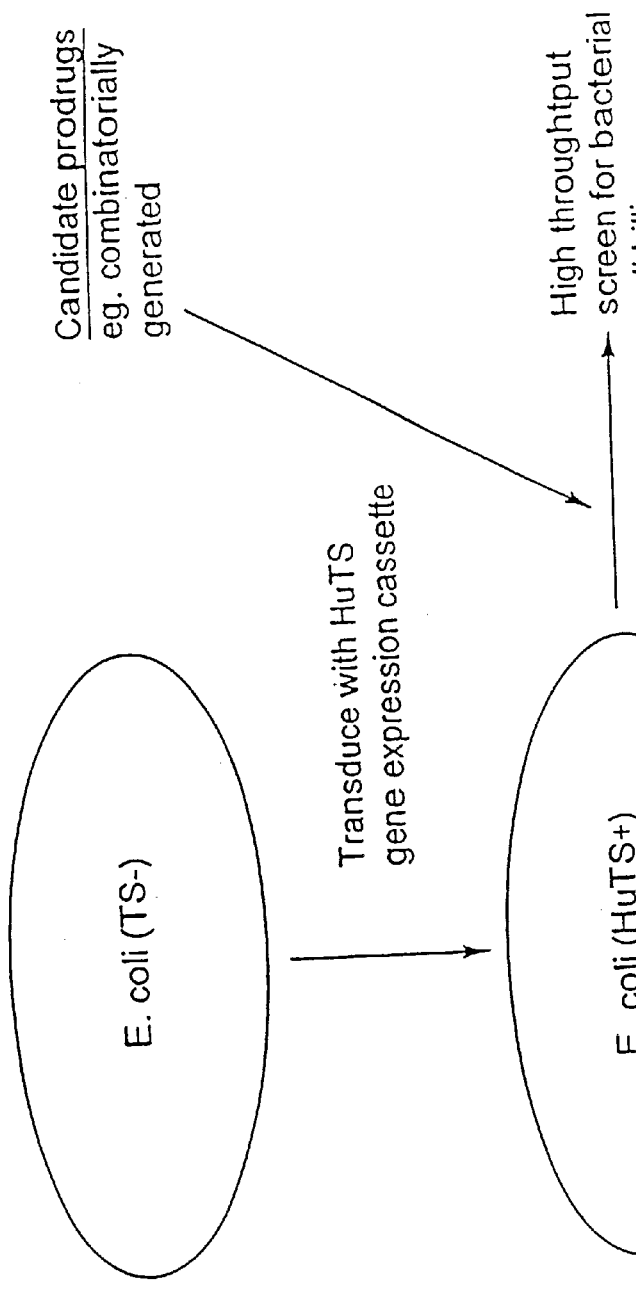
FIG. 4 schematically shows how to find a lead human thymidylate synthase (TS) prodrug using TS-negative *E. coli* as the cell target.

For example and as shown in FIG. 4, a foreign gene, e.g., a human gene encoding TS, can be inserted into the host cell such that human TS is expressed. This genetically engineered cell is shown as the "test cell" in FIG. 3. The "control cell" does not express the target enzyme. In some embodiments it may be necessary to supplement the culture media with the protein product of the target enzyme.

In a separate embodiment, the wild type host cell is deficient or does not express more than one enzyme of interesl As shown in FIG. 4, the host cell does not endogenously produce thymidine kinase ($TK^-$) or thymidylate synthase ($TS^-$). Genes coding for the human counterpart of these enzymes are introduced into the host cell to obtain the desired level of expression. The level of expression of enzyme in each transfected cell line can be monitored by methods described herein, e.g., by immunoblot and enzyme assay in cell lysates, using monoclonal or polyclonal antibody previously raised against the enzyme for immunodetection. See, e.g., as described by Chen, L. et al. (1996). Enzymatic assays also can be performed as reviewed by Carreras, C. W. and Santi, D. N. (1995) using detectable labeled substituents, e.g. tritium labeled substituents. A possible advantage of the "two enzyme" system is that the requirement for activation by two enzymes preferentially overexpressed in tumor cells will provide increased safety for normal cells.

The test cell is grown in small multi-well plates and is used to detect the biologic activity of test prodrugs. For the purposes of this invention, the successful candidate drug will block the growth or kill the test cell type, but leave the control cell type unharmed.

The candidate prodrug can be directly added to the cell culture media or previously conjugated to a ligand specific to a cell surface receptor and then added to the media. Methods of conjugation for cell specific delivery are well known in the art, see e.g., U.S. Pat. Nos. 5,459,127; 5,264, 618; and published patent specification WO 91/17424 (published Nov. 14, 1991). The leaving group of the candidate prodrug can be detectably labeled, e.g., with tritium. The target cell or the culture media is then assayed for the amount of label released from the candidate prodrug. Alternatively, cellular uptake may be enhanced by packaging the prodrug into liposomes using the method described in Lasic, D. D. (1996) or combined with cytofectins as described in Lewis, J. G. et al. (1996).

In a separate embodiment, cultured human tumor cells overexpressing the enzyme of interest i.e., target enzyme, are identified as described above. The cells are contacted with the potential therapeutic agent under conditions which favor the incorporation of the agent into the intracellular compartment of the cell. The cells are then assayed for inhibition of cellular proliferation or cell killing.

It should be understood, although not always explicitly stated, each embodiment can be further modified by providing a separate target cell to act as a control by receiving an effective amount of a compound, such as, for example, the compounds shown below, which have been shown to be potent prodrugs.

Figure 5:
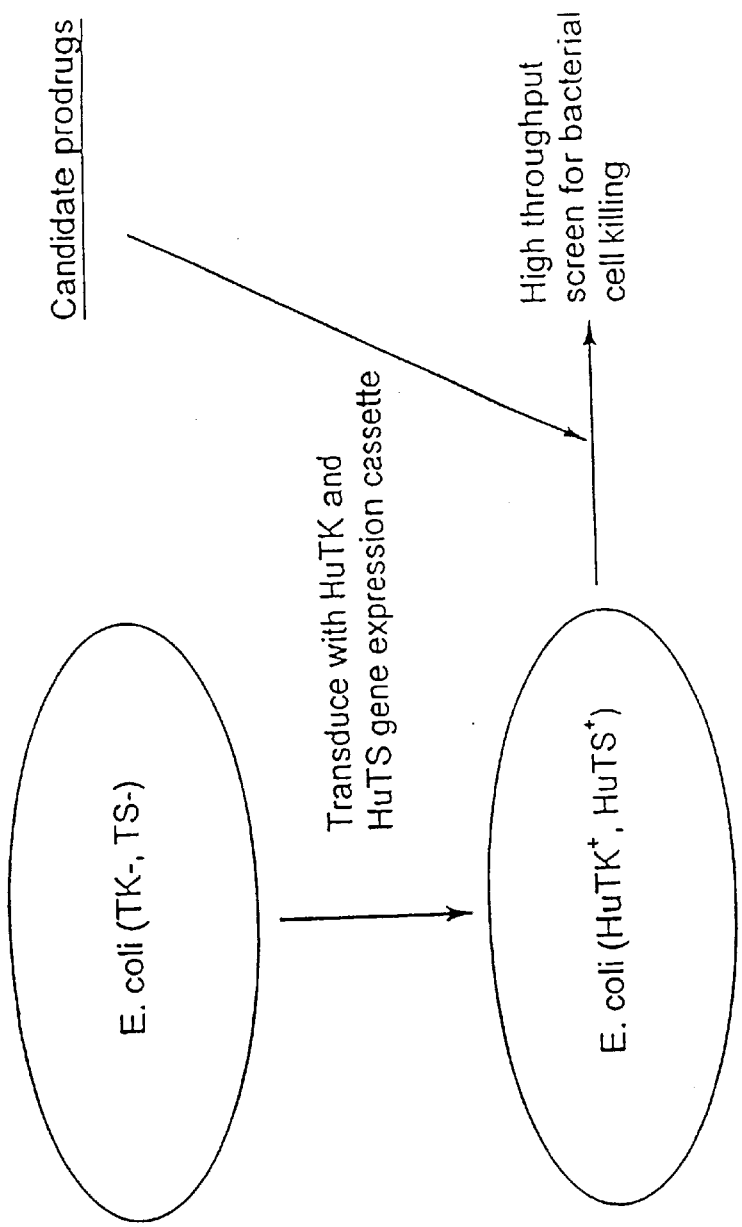
FIG. 5 shows an example of how to use this screen to simultaneously optimize the prodrug for reactivity to two target enzymes.

A high throughput screen to identify biologically active compounds is outlined in FIGS. 3, 4 and 5. The basis of the test is the ease of genetic manipulation and growth of *E. coli*, and similar single cell organisms (e.g. yeast), see Miller (1992) and Spector et al. (1998). The key step is removing the endogenous enzyme activity corresponding to an enzyme target for prodrug design. This can be done by any of the methods described by Miller (1992), Sambrook, et al. (1989) or Spector et al. (1998). These methods include chemical and biologic (e.g. viral or transponson insertional) mutagenesis, followed by an appropriate selection procedure. The TS negative (TS⁻) cell then becomes a negative control for the identification of prodrugs that, when acted upon by thymidylate synthase, become cell toxins. A similar approach can be made with other cell types, e.g. other bacteria, yeast, or other selectable single cell organisms. In the assay, both control and recombinant organisms are compared for sensitivity to the test compounds. As will be understood by those skilled in the art, prodrugs which distinguish between species of enzyme can also be derived from this procedure. For example, otherwise identical cells expressing human and yeast enzymes can be used to detect antibiotic prodrugs which are preferentially toxic only to the cells expressing the yeast enzyme. In this way, novel and specific antibiotics can be discovered.

Example cell lines are ras-transformed NIH 3T3 cells (obtained from the ATCC) and are engineered to express increasing quantities of human thymidylate synthase (Hu TS) from the cloned cDNA. Transfection is done in a transient or permanent basis (see Chen, L. et al. (1996), Hudziak, R. M. et al. (1988), and Carter, P. et al. (1992). NIH-000 (ras-transformed parent cell line); NIH-001 (low expressor of HuTS); NIH-002 (intermediate expressor of Hu TS); NIH-003 (high expresser of HuTS). The level of expression of TS in each cell line is monitored by immunoblot and enzyme assay in cell lysates, using antibody directed versus HuTS protein for immunodetection (e.g., as described in Chen, L. et al. (1996)). Enzymatic assays are performed as reviewed by Carreras and Santi (1995).

Human colorectal and breast tumor cell lines are screened for expression of HuTS enzyme. Cell lines expressing low, moderate and high levels of HuTS will be exposed to drug candidates as described above for the NIH 3T3 cell lines. Growth inhibition and cytotoxicity are monitored as described above. Similar tests can be carried out for each of the enzymes listed in Table 1.

An alternative embodiment for a prodrug taking advantage of TS overexpression in tumor cells is a deoxyuridine phosphoramidate, or other modifications (cited herein) conjugated with a therapeutic radionuclide. An example of a therapeutic radionuclide is rhenium 188. The isotope can be synthesized essentially as described by Callahan, et al. (1989). Alternatively, it can be obtained commercially, for example from Mallicrodt Medical BV, The Netherlands. The therapeutic radionuclide can be conjugated with deoxyuridine, or deoxyuridine 5'-phosphoramidate, or other derivative, by standard methods (for example, as described by Lin, W-Y., et al. (1997)). The radionuclide-containing deoxyuridine phosphoramidate will be preferentially taken up into the DNA of tumor cells overexpressing thymidylate synthase, and cause their death via concentrated emission of beta and gamma radiation. Alternative radionuclides include rhenium-186, and others (Troutner, D. A. (1987)).

In Vivo Administration

The in vitro assays are confirmed in animal models bearing human tumors or infected with an antibiotic resistant microorganism to determine in vivo efficacy.

Another aspect of this invention is a method for treating a pathology characterized by hyperproliferative cells in a subject comprising administering to the subject a therapeutic amount of a prodrug that is converted to a toxin in a hyperproliferative cell by an endogenous intracellular enzyme as defined herein. In a preferred embodiment, the compound is selected from the compounds defined in the section "Prodrugs," Infira When the prodrug is administered to a subject such as a mouse, a rat or a human patient, the agent can be added to a pharmaceutically acceptable carrier and systemically or topically administered to the subject.

To determine patients that can be beneficially treated, a tumor sample is removed from the patient and the cells are assayed for the level of expression of the enzyme of interest. If the expression is above that expressed in normal cells so that a toxic amount of the prodrug would cause administered without undesirable side effects, then the tumor or cells are determined to be benefically treated and thus, the patient is suitable for the therapy of this invention. For example, if the target enzyme is expressed at least about 2 times and preferably about 3 times higher than normal cells, the patient is a suitable subject for the therapy method of this invention. Therapeutic amounts can be empirically determined and will vary with the pathology being treated, the subject being treated and the toxicity of the converted prodrug or cellular toxin.

When delivered to an animal, the method is useful to further confirm efficacy of the prodrug. As an example of an animal model, groups of nude mice (Balb/c NCR nu/nu female, Simonsen, Gilroy, Calif.) are each subcutaneously inoculated with about $10^5$ to about $10^9$ hyperproliferative, cancer or target cells as defined herein. When the tumor is established, the prodrug is administered, for example, by subcutaneous injection around the tumor. Tumor measurements to determine reduction of tumor size are made in two dimensions using venier calipers twice a week. Other animal models may also be employed as appropriate. Lovejoy et al. (1997) and Clarke, R. (1996).

Administration in vivo can be effected in one dose, continuously or intermittently throughout the course of treatment. Methods of determining the most effective means and dosage of administration are well known to those of skill in the art and will vary with the composition used for therapy, the purpose of the therapy, the target cell being treated, and the subject being treated. Single or multiple administrations can be carried out with the The agents and compositions of the present invention can be used in the manufacture of medicaments and for the treatment of humans and other animals by administration in accordance with conventional procedures, such as an active ingredient in pharmaceutical compositions.

The pharmaceutical compositions can be administered orally, intranasally, parenterally or by inhalation therapy, and may take the form of tablets, lozenges, granules, capsules, pills, ampoules, suppositories or aerosol form. They may also take the form of suspensions, solutions and emulsions of the active ingredient in aqueous or nonaqueous diluents, syrups, granulates or powders. In addition to a compound of the present invention, the pharmaceutical compositions can also contain other pharmaceutically active compounds or a plurality of compounds of the invention.

More particularly, a compound of the formula of the present invention also referred to herein as the active ingredient, may be administered for therapy by any suitable route including oral, rectal, nasal, topical (including transdermal, aerosol, buccal and sublingual), vaginal, parental (including subcutaneous, intramuscular, intravenous and intradermal) and pulmonary. It will also be appreciated that the preferred route will vary with the condition and age of the recipient, and the disease being treated.

In general, a suitable dose for each of the above-named compounds, is in the range of about 1 to about 100 mg per kilogram body weight of the recipient per day, preferably in the range of about 1 to about 50 mg per kilogram body weight per day and most preferably in the range of about 1 to about 25 mg per kilogram body weight per day. Unless otherwise indicated, all weights of active ingredient are calculated as the parent compound of the formula of the present invention for salts or esters thereof, the weights would be increased proportionately. The desired dose is preferably presented as two, three, four, five, six or more sub-doses administered at appropriate intervals throughout the day. These sub-doses may be administered in unit dosage forms, for example, containing about 1 to about 100 mg, preferably about 1 to above about 25 mg, and most preferably about 5 to above about 25 mg of active ingredient per unit dosage form. It will be appreciated that appropriate dosages of the compounds and compositions of the invention may depend on the type and severity and stage of the disease and can vary from patient to patient. Determining the optimal dosage will generally involve the balancing of the level of Determining the optimal dosage will generally involve the balancing of the level of therapeutic benefit against any risk or deleterious side effects of the treatments of the present invention.

Ideally, the prodrug should be administered to achieve peak concentrations of the active compound at sites of disease. This may be achieved, for example, by the intravenous injection of the prodrug, optionally in saline, or orally administered, for example, as a tablet, capsule or syrup containing the active ingredient. Desirable blood levels of the prodrug may be maintained by a continuous infusion to provide a therapeutic amount of the active ingredient within disease tissue. The use of operative combinations is contemplated to provide therapeutic combinations requiring a lower total dosage of each component antiviral agent than may be required when each individual therapeutic compound or drug is used alone, thereby reducing adverse effects.

While it is possible for the prodrug ingredient to be administered alone, it is preferable to present it as a pharmaceutical formulation comprising at least one active ingredient, as defined above, together with one or more pharmaceutically acceptable carriers therefor and optionally other therapeutic agents. Each carrier must be "acceptable" in the sense of being compatible with the other ingredients of the formulation and not injurious to the patient.

Formulations include those suitable for oral, recta, nasal, topical (including transdermal, buccal and sublingual), vaginal, parenteral (including subcutaneous, intramuscular, intravenous and intradermal) and pulmonary administration. The formulations may conveniently be presented in unit dosage form and may be prepared by any methods well known in the art of pharmacy. Such methods include the step of bringing into association the active ingredient with the carrier which constitutes one or more accessory ingredients. In general, the formulations are prepared by uniformly and intimately bringing into association the active ingredient with liquid carriers or finely divided solid carriers or both, and then if necessary shaping the product.

Formulations of the present invention suitable for oral administration may be presented as discrete units such as capsules, cachets or tablets, each containing a predetermined amount of the active ingredient; as a powder or granules; as a solution or suspension in an aqueous or non-aqueous liquid; or as an oil-in-water liquid emulsion or a water-in-oil liquid emulsion. The active ingredient may also be presented a bolus, electuary or paste.

A tablet may be made by compression or molding, optionally with one or more accessory ingredients. Compressed tablets may be prepared by compressing in a suitable machine the active ingredient in a free-flowing form such as a powder or granules, optionally mixed with a binder (e.g., povidone, gelatin, hydroxypropylmethyl cellulose), lubricant, inert diluent, preservative, disintegrant (e.g., sodium starch glycolate, cross-linked povidone, cross-linked sodium carboxymethyl cellulose) surface-active or dispersing agent. Molded tablets may be made by molding in a suitable machine a mixture of the powdered compound moistened with an inert liquid diluent. The tablets may optionally be coated or scored and may be formulated so as to provide slow or controlled release of the active ingredient therein using, for example, hydroxypropyhnethyl cellulose in varying proportions to provide the desired release profile. Tablets may optionally be provided with an enteric coating, to provide release in parts of the gut other than the stomach.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Pharmaceutical compositions for topical administration according to the present invention may be formulated as an ointment, cream, suspension, lotion, powder, solution, past, gel, spray, aerosol or oil. Alternatively, a formulation may comprise a patch or a dressing such as a bandage or adhesive plaster impregnated with active ingredients and optionally one or more excipients or diluents.

For diseases of the eye or other external tissues, e.g., mouth and skin, the formulations are preferably applied as a topical ointment or cream containing the active ingredient in an amount of, for example, about 0.075 to about 20% w/w, preferably about 0.2 to about 25% w/w and most preferably about 0.5 to about 10% w/w. When formulated in an ointment, the prodrug may be employed with either a paraffinic or a water-miscible ointment base. Alternatively, the prodrug ingredients may be formulated in a cream with an oil-in-water cream base.

If desired, the aqueous phase of the cream base may include, for example, at least about 30% w/w of a polyhydric alcohol, i.e., an alcohol having two or more hydroxyl groups such as propylene glycol, butane-1,3-diol, mannitol, sorbitol, glycerol and polyethylene glycol and mixtures thereof. The topical formulations may desirably include a compound which enhances absorption or penetration of the prodrug ingredient through the skin or other affected areas. Examples of such dermal penetration enhancers include dimethylsulfoxide and related analogues.

The oily phase of the emulsions of this invention may be constituted from known ingredients in an known manner. While this phase may comprise merely an emulsifier (otherwise known as an emulgent), it desirably comprises a mixture of at lease one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and/or fat make up the so-called emulsifying ointment base which forms the oily dispersed phase of the cream formulations.

Emulgents and emulsion stabilizers suitable for use in the formulation of the present invention include Tween 60, Span 80, cetostearyl alcohol, myristyl alcohol, glyceryl monostearate and sodium lauryl sulphate.

The choice of suitable oils or fats for the formulation is based on achieving the desired cosmetic properties, since the solubility of the active compound in most oils likely to be used in pharmaceutical emulsion formulations is very low. Thus the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

Formulations suitable for topical administration to the eye also include eye drops wherein the active ingredient is dissolved or suspended in a suitable carrier, especially an aqueous solvent for the prodrug ingredient. The prodrug ingredient is preferably present in such formulation in a concentration of about 0.5 to about 20%, advantageously about 0.5 to about 10% particularly about 1.5% w/w.

Formulations for ectal administration may be presented as a suppository with a suitable base comprising, for example, cocoa butter or a salicylate.

Formulations suitable for vaginal administration may be presented as suppositories, tampons, creams, gels, pastes, foams or spray formulations containing in addition to the prodrug ingredient, such carriers as are known in the art to be appropriate.

Formulations suitable for nasal administration, wherein the carrier is a solid, include a coarse powder having a particle size, for example, in the range of about 20 to about 500 microns which is administered in the manner in which snuff is taken, i.e., by rapid inhalation through the nasal passage from a container of the powder held close up to the nose. Suitable formulations wherein the carrier is a liquid for administration as, for example, nasal spray, nasal drops, or by aerosol administration by nebulizer, include aqueous or oily solutions of the prodrug ingredient.

Formulations suitable for parenteral administration include aqueous and non-aqueous isotonic sterile injection solutions which may contain anti-oxidants, buffers, bacteriostats and solutes which render the formulation isotonic with the blood of the intended recipient; and aqueous and non-aqueous sterile suspensions which may include suspending agents and thickening agents, and liposomes or other microparticulate systems which are designed to target the compound to blood components or one or more organs. The formulations may be presented in unit-dose or multi-dose sealed containers, for example, ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described.

Preferred unit dosage formulations are those containing a daily dose or unit, daily subdose, as herein above-recited, or an appropriate fraction thereof, of a prodrug ingredient.

It should be understood that in addition to the ingredients particularly mentioned above, the formulations of this invention may include other agents conventional in the art having regard to the type of formulation in question, for example, those suitable of oral administration may include such further agents as sweeteners, thickeners and flavoring agents.

Prodrugs and compositions of the formula of the present invention may also be presented for the use in the form of veterinary formulations, which may be prepared, for example, by methods that are conventional in the art.

Provided below is a brief summary of cells and target enzymes that are useful to activate the prodrugs of this invention.

Tyrosine Kinases

The tyrosine kinase superfamily comprises the EGF receptor (EGFR), the macrophage colony-stimulating factor (CSF-1) receptor (v-fns), and the insulin receptor, which shows 30 to 40% identity with the product of the ros oncogene. More specifically, the members of this superfamily include v-src, c-src, EGFR, HER2, CSF-1 receptor, c-fns, v-ros, insulin receptor, and c-mos. See FIG. 8.5 of Burck, K. B. et al., eds. (1988). Overexpression of members of the type 1 receptor tyrosine kinase superfamily has been documented in many types of cancer (Eccles, S. A. et al. (1994–95)). Overexpression of tyrosine kinases is linked to exposure to the a-cancer biologic agent TNF-α (Hudziak, R. M. et al. (1988) and Hudziak, R. M. et al. (1990)) and to chemotherapy (Stühlinger et al. (1994)).

The transforming gene of the Rous sarcoma virus, v-src, encodes an enzyme that phosphorylates tyrosine residues on proteins. The c-src proto-oncogene is found on chromosome 20. Tissues and cell lines derived from tumors of neuroectodermal origin having a neural phenotype express high levels of c-src accompanied by high specific kinase activity.

Several groups of investigators have reported overexpression of c-erbB-2/neu ("HER2") oncogene in cancer cells. Brison (1993) noted that erbB proto-oncogene is amplified in human tumors with resultant overexpression in most cases. Amplification of the c-erbB-2/neu oncogene has been reported in human mammary tumors (Slamon, et al. (1987), van de Vijver et al. (1987), Pupa et al. (1993), and Andersen et al. (1995)) and in bladder tumors (Sauter et al. (1993)), and in every case amplification was accompanied by overexpression. c-erbB-2/neu overexpression also has been reported in ovarian cancer tissue samples (Slamon, et al. (1989), Meden et al. (1994), and Felip et al. (1995)), and tumors derived from the peripheral nervous system. Sukumar and Barbacid, (1990).

To perform the drug screening assay, tumor cell lines will be assayed for expression of the oncogene or will be engineered to express varying levels of tyrosine kinase. Selected cell lines are cultured and candidate drugs are added in varying concentrations. The cells are assayed for cell killing or inhibition of cellular proliferation, as described in Hudziak, R. M. et al. (1988) and Hudziak, R. M. et al. (1990).

Dihydrofolate Reductase

Methotrexate is a potent inhibitor of dihydrofolate reductase, an enzyme necessary for intracellular folate metabolism. Dihydrofolate reductase functions to regenerate tetrahydrofolate from dihydrofolate, a product of the thymidylate synthase reaction (Voet, et al. eds. (1995), p. 813). It is well established that an important mechanism of resistance of cells to methotrexate is an increase in DHFR activity due to amplification of the DHFR gene. Banerjee, D. et al. (1995), Schinmke, R. T. et al. (1988). Lönn, U. et al. (1996) reported that amplification of the DHFR gene occurred in breast cancer patients who previously received adjuvant chemotherapy (cyclophosphamide, methotrexate, 5-fluorouracil [CMF]) after surgery. Lack of the retinoblastoma (Rb) may also lead to enhanced MTX resistance as a consequence of an increase in DHFR MRNA expression activity without gene amplification. Li, W. W. et al. (1995). Cell lines with mutated p53 have been shown to undergo gene amplification, and the resistant cells are selected by chemotherapy. Banerjee, D. et al. (1995), Yin, Y. et al. (1992) and Livingston, L.R. et al. (1992). For the purposes of performing the assay of this invention, Schimke, R. T. et al. (1988) describes several mouse, hamster and human cell lines. Alternatively, the PCR method of Lönn U. et al. (1996) is used to assay DHFR gene amplification and identify cells that are useful in the method of identifying therapeutic agents as described herein. The nucleotide sequence of the cDNA coding for the human dihydrofolate reductase is provided in Masters, J. N. and Attardi, G. (1983) and cells can be engineered to express varying levels of the enzyme as noted herein. Dicken, A. P. et al. (1993) describes a mutant DHFR gene selected by chemotherapy. Purification of DHFR and assays related to enzyme function are described in Nakano, T. et al. (1994). Alternatively, cDNA encoding DHFR is transfected into NIH 3T3 cells. Candidate drugs are added in varying concentrations and cell killing and inhibition of proliferation are assayed.

Antimetabolites dependent on dihydrofolate reductase activity can be synthesized by the attachment of, for example, an alkylating group to either the N5 or the C6 position of dihydrofolate. Reduction of the N5-C6 bond by DHFR will result in the release of the alkylating agent. In addition to the alkylating groups, any moiety whose release by DHFR results in the production of a toxin or an antimetabolite will be useful in the practice of the invention. These compounds can be further modified by the addition of a phosphatese or phosphoramidate moiety.

Mulfidrug Resistant Tumors

Multidrug resistance (MDR) is a generic term for the variety of strategies tumor cells use to evade the cytotoxic effects of anticancer drugs. MDR is characterized by a decreased sensitivity of tumor cells not only to the drug employed for chemotherapy but also to a broad spectrum of drugs with neither obvious structural homology nor common targets. This pleiotropic resistance is one of the major obstacles to the successful treatment of tumors. MDR may result from structural or functional changes at the plasma membrane or within the cytoplasm, cellular compartments, or nucleus. Molecular mechanisms of MDR are discussed in terms of modifications in detoxification and DNA repair pathways, changes in cellular sites of drug sequestration, decreases in drug-target affinity, synthesis of specific drug inhibitors within cells, altered or inappropriate targeting of proteins, and accelerated removal or secretion of drugs.

One of the mechanisms implicated in MDR results from amplification and over-expression of a gene known as the ATP-dependent multidrug resistant associated protein (MRP) in drug selected cell lines. For a review of the mechanisms of MDR, see Gottesman, M. M. et al. (1995) and Noder et al. (1996).

To establish MDR cell lines, drug selections are conducted in either a single step or in multiple steps as described in Gottesman, M. M. et al. (1995) and Simon, S. M. and Schindler, M. (1994), and references cited therein. The isolation of DNA sequences coding for MDR from various mammalian species is described in Gros, P. et al. (1986), Gudkov, A. V. et al. (1987), and Roninson, I. B. et al. (1984), and reviewed in Gottesman, M. M. et al. (1995), and cells can be engineered to express varying levels of this enzyme as described above. The prodrug targeting MDR will be based upon the ATPase activity of this transporter.

RiTonucleotide Reductase

The enzyme ribonucleotide reductase reduces ribonucleoside diphosphates to the corresponding deoxyribonucleoside diphosphates. The enzyme is a tetramer made up of two a-subunits and two β-subunits. Hydroxyurea specifically blocks this reaction by interacting with the tyrosyl free radical (Tyr-122) of the $\beta_2$-substrate complex. Voet et al. (1995). The goal in targeting this reaction is to allow the accumulation of the free radical product $O_2^-$, which is highly cytotoxic.

Application of Technology to Other Diseases

While the primary focus of this application is directed to cancer, it should be recognized that the technology is broadly applicable to other diseases, especially antibiotic resistant bacterial infections. The β-lactam antibiotics encounter resistance in bacteria as the result of overexpression of β-lactamases. Hamilton-Miller, J. M. T. and Smith, J. T. eds. (1979) p. 443. Other enzymes, such as the aminoglycoside phosphotransferese Type III, are induced and selected for following treatment with arminoglycoside antibiotics, such as kanamycin. McKay, G. A. et al. (1994). For the purpose of this application, prodrug substrates derived from known substrates will be prepared that will not block enzyme activity, but will instead take advantage of the high enzyme activity to generate intracellular toxins to the infectious agents.

Thymidylate Synthase

The overexpression of thyrnidylate synthase is associated with colon cancer, breast cancer, gastric cancer, head and neck cancer, liver cancer and pancreatic cancer. These diseases are currently treated by antimetabolite drugs (uracil-based, folate-based, or quinazoline-based, (see Table 1)). In each of these cases it is likely that tumor suppressor loss and/or 5-fluorouracil therapy can lead to amplified activity of TS, or select for drug resistant forms of the enzyme, and thereby lead to drug-resistance of the disease relapse. Lönn, U. et al. (1996) reported that amplification of the TS gene occurred in breast cancer patients who previously received adjuvant chemotherapy (cyclophosphamide, methotrexate, 5-fluorouracil [CMF]) after surgery. This enhanced TS expression is in addition to the basic increase of TS which results from loss of tumor suppressor function. The principal reaction normally performed by TS is the synthesis of deoxythymidine monophosphate (dTMP) and dihydrofolate (DHF) from deoxyuridine monophosphate (dUMP) and N(5),N(10)-methylene-tetrahydrofolate (ThF). In one embodiment, a derivative of uracil or THF is provided to cells expressing TS. For purposes of this invention, "uracil" (base only) and "uridine" (base and sugar) are used interchangeably and synonomously. Table 4 (below) summarized the many cancer types impacted by elevated TS expression.

TABLE 4

Thymidylate Synthase Overexpression Impacts Survival of Cancer Patients
Median Survival Time (Months)

| Cancer | TS (Low) | TS (High) | References |
| --- | --- | --- | --- |
| Breast | 84 | 54 | Pestalozzi et al., 1997 |
| NSCLC | 46 | 10 | Volm and Mattern, 1992 |
| Colon | 13.6 | 8.2 | Leichman et al., 1997 |
| Rectal | >60 | 24 | Johnston et al., 1994 |
| Head and Neck | >72 | 24 | Johnston et al., 1997 |
| Stomach | 43 | 6 | Lenz et al., 1995 |
| | Average > 53.1 | Average 21 | |

Fold difference between averages > 2.5

The derivative or "prodrug" is converted by the enzyme into highly cytotoxic metabolites. The low level of TS expressed in normal cells will not produce a toxic amount of the converted toxin. High levels of TS expressed in disease tissues generate more toxin and thereby lead to an inhibition of cell proliferation and/or cell death. For example, current therapy utilizes 5-fluorodeoxyuridylate to inhibit TS activity. During the reaction with substrate, the fluorine atom irreversibly becomes attached to the TS enzyme and inhibits it. In one embodiment, the proposed new therapeutic allows TS to complete the reaction but generates a modified product that, when incorporated into DNA, causes a toxic effect. The enzyme product may also block other critical cellular functions (e.g. protein synthesis or energy metabolism). Conversion of the prodrug also can release a metabolite, such as $CN^-$ which is toxic to the cell. Derivatives of uracil/dUMP and N(5)(10)-THF can be synthesized, all of which have the potential of generating toxic product after metabolic transformation by TS.

Primary sequences show that TS is one of the most highly conserved enzymes. Perry, K. et al. (1990). Crystal structures of TS from several procaryotic species, Lactobacillus casei (Hardy, L. W. et al. (1987); Finer-Moore, J. et al. (1993)) and Escherichia coli (Perry, K. et al. (1990)); an eukaryote Leishmania major (Knighton, E. R. et al. (1994)); and T4 phage (Finer-Moore, J. S. et al., (1994)) have been determined and indicate that tertiary structure also is very well conserved. The sequence alignment of the species of TS whose three dimensional structures have been determined and is shown in Schiffer, C. A. et al. (1995). From these amino acid sequences, the DNA sequences can be deduced or isolated using methods well known to those of skill in the art. Sambrook, et al. (1989). Alternatively, some 29 TS sequences from different organisms have been cloned and deposited into the DNA databases as described in Carreras, C. W. and Santi, D. V. (1995). The sequence of human thymidylate synthase gene, its cloning, expression and purification is provided in Takeishi, K. et al. (1985), Davisson, V. J. et al. (1989) and Davisson, V. J. et al. (1994). Genes encoding the TS protein and containing the necessary regulatory sequences, are constructed using methods well known to those of skill in the art. The gene encoding TS is introduced to target cells by electroporation, transformation or transfection procedures. Sambrook, et al. (1989). Alternatively, the gene is inserted into an appropriate expression vector by methods well known in the art, e.g., as described in Carreras, C. W. and Santi, D. V. (1995), Miller (1992) and Spector et al. (1998). The expression vector inserts the TS gene into the cells. The cells are then grown under conditions which favor the expression and production of TS protein.

Human gastric cancer cell lines, MKN-74, MKN45, MKN-28 and KATO-III can be used in the assay described above to identify potential therapeutic agents which are selective substrates for TS. MKN-74 and MKN-45 are established from well and poorly differentiated adenocarcinomas, respectively. These cell lines and culture conditions are described in Osaki, M. et al. (1997) and references cited therein. Alternatively, tumor cell lines such as those described by Copur, S. et al. (1995), which have been selected by 5-FU to overexpress thymidylate synthase may be used.

Quantitation of TS can be performed using enzymatic biochemical assays that are well known to those with skill in the art. To quantify the level of TS protein and TS gene expression from human tumor tissue samples, the methods as reported by Johnston, P. G. et al. (1991) and Horikoshi, T. et al. (1992) provide sensitive assays. Alternatively, the PCR method of Lönn, U. et al. (1996) is used to assay TS gene amplification and identify cells that are useful in the method of identifying therapeutic agents as described herein.

As is apparent to one skilled in the art, control cell culture systems without drug and separately with a reference drug such as the compounds exemplified below, also are assayed. A lead compound is one which preferentially kills target cells with about 2-fold and preferably about 3-fold or greater activity than normal cells. This invention also provides the agents identified by the methods described herein.

In another aspect, this invention provides a method for inhibiting the proliferation of a hyperproliferative cell, by first conducting the above assay. A prodrug identified by this assay is contacted with the cell and converted to a toxic metabolite in the cell by an endogenous intracellular enzyme as described above. Growth or cytotoxicity of bacteria, yeast and other cell types can be monitored as described by Miller et al. (1992), Sugarman et al. (1985) and Spector et al. (1998).

TS Prodrugs

In a preferred embodiment, the present invention involves two classes of compounds activated by TS, each a derivative of 5-substituted deoxyuridine monophosphate or a protected 5-substituted uracil or deoxyuridine monophosphate. Protected 5-substituted deoxyuridine monophosphate derivatives are those in which the phosphate moiety has been blocked through the attachment of suitable chemical protecting groups. Protection of 5-substituted deoxyuridine monophosphate derivatives can improve solubility, facilitate cellular penetration, facilitate passage across the blood-brain barrier, and prevent action of cellular or extracellular phosphatases, which might otherwise result in loss of the phosphate group. In another embodiment, 5-substituted uracil or uridine derivatives are administered to cells containing nucleoside kinase activity, wherein the 5-substituted uracil/uridine derivative is converted to a 5-substituted uridine monophosphate derivative. Uridine derivatives may also be modified to increase their solubility, cell penetration, and/or ability to cross the blood-brain barrier.

Action of thymidylate synthase upon 5-substituted uridine monophosphate derivatives can release the substituent attached to the 5-position ("leaving group") of the pyrimidine ring. The released substituent is then capable, either inherently or following reaction with another cellular component, of acting as a toxin or an inhibitor of cellular proliferation.

General Synthesis of Compounds of Class I

The L and D isomers of the compounds of Class I have the structure:

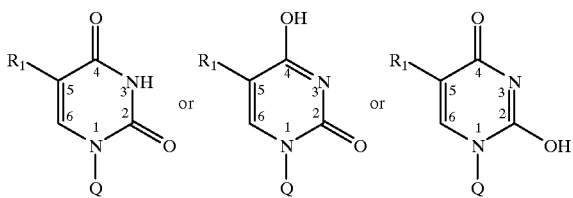

In the above formulae, $R_1$ (at the 5-position) is or contains a leaving group which is a chemical entity that has a molecular dimension and electrophilicity compatible with extraction from the pyrimidine ring by thymidylate synthase, and which upon release from the pyrimidine ring by thdylate synthase, has the ability to inhibit the proliferation of the cell or kill the cell.

In the above formulae, Q is a phosphate or phosphoramidate derivative containing a chemical entity selected from the group consisting of sugar groups, thio-sugar groups, carbocyclic groups, and derivatives thereof Examples of sugar groups include, but are not limted to, monosaccharide cyclic sugar groups such as those derived from oxetanes (4-membered ring sugars), furanoses (5-membered ring sugars), and pyranoses (6-membered ring sugars). Examples of furanoses include threo-furanosyl (from threose, a four-carbon sugar); erythro-furanosyl (from erythrose, a four-carbon sugar); ribo-furanosyl (from ribose, a five-carbon sugar); ara-furanosyl (also often referred to as arabino-furanosyl; from arabinose, a five-carbon sugar); xylo-furanosyl (from xylose, a five-carbon sugar); and lyxo-furanosyl (from lyxose, a five-carbon sugar). Examples of sugar group derivatives include "deoxy", "keto", and "dehydro" derivatives as well as substituted derivatives. Examples of thio sugar groups include the sulfur analogs of the above sugar groups, in which the ring oxygen has been replaced with a sulfur atom. Examples of carbocyclic groups include $C_4$ carbocyclic groups, $C_5$ carbocyclic groups, and $C_6$ carbocyclic groups which may further have one or more subsituents, such as —OH groups.

In one embodiment, Q is a β-D-ribofuranosyl group of the formula:

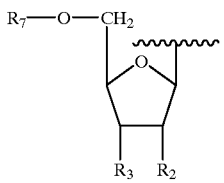

wherein $R_7$ is selected from the group consisting of phosphoryl, phosphoramidate and derivatives thereof, and wherein $R_2$ and $R_3$ are the same or different and are independently —H or —OH.

In some embodiments, $R_1$ is an alkenyl group, i.e., (—CH=CH)$_n$—$R_4$, wherein n is an integer from 0 to 10, and $R_4$ is a halogen such as is I⁻ or Br⁻, CN⁻ or mercury; wherein $R_2$ is H and $R_3$ is —OH; wherein $R_2$ is OH and $R_3$ is H; wherein $R_2$ and $R_3$ are H; or wherein $R_2$ and $R_3$ are OH.

In another aspect, $R_1$ is an alkenyl group, i.e., (—CH=CH)$_n$—$R_4$,, wherein n is an integer from 0 to 10, and $R_4$ is or contains a group selected from the group consisting of H, a halogen, alkyl, alkene, aLkyne, hydroxy, —O-alkyl, —O-aryl, O-heteroaryl, —S-alkyl, —S-aryl, a cyanide, cyanate and thiocyanate halovinyl group, a halomercuric group, —S-heteroaryl, —NH$_2$, —NH-alkyl, —N(alkyl)$_2$, —NHCHO, —NHOH, —NHO-alkyl, NH$_2$CONHO—, and NHNH$_2$. In these embodiments, further aspects include: wherein $R_2$ and $R_3$ are H; wherein $R_2$ is OH and $R_3$ is H; herein $R_2$ is H and $R_3$ is OH; or wherein $R_2$ and $R_3$ are OH.

A preferred embodiment for the substituent in the $R_1$ position is one that could undergo an allylic interchange as shown in FIG. 8.

In a still further aspect, the candidate therapeutic agent is a compound of the formula:

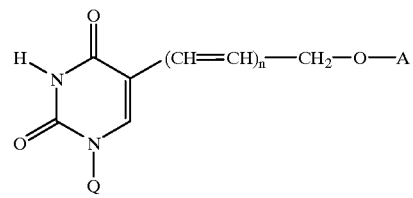

wherein n is an integer from 0 to 10; wherein A is a phosphoramide derivative, or a compound of the formula:

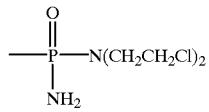

and wherein Q is selected from the group consisting of H, an unsubstituted or substituted sugar as defined above and a substituted or unsubstituted carbocyclic as defined above.

In a further embodiment, the compounds described above, are modified by Q having the structure:

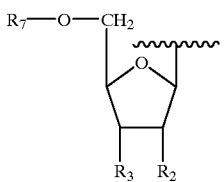

wherein $R_7$ is selected from the group consisting of H, phosphoryl, phosphoranidate and derivatives thereof, and wherein $R_2$ and $R_3$ are the same or different and are independently —H or —OH. In one embodiment, $R^7$ is not H. For these embodiments, $R_1$ also can have the structure —(CH=CH)$_n$—$R_4$, wherein n is an integer from 0 to 10, and $R_4$ is selected from the group consisting of H, a halogen, alkyl, alkene, alkyne, hydroxy, —O-alkyl, —O-aryl, O-heteroaryl, —S-alkyl, —S-aryl, —S-heteroaryl, —NH$_2$, —NH-alkyl, —N(alkyl)$_2$, —NHCHO, a cyanide, cyanate and thiocyanate halovinyl compound, a halomercuric compound, —NHOH, —NHO-alkyl, NHNH$_2$, and NH$_2$CONHO—.

Additionally, in a further aspect, the candidate therapeutic agent is a compound of the formula:

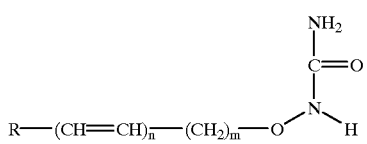

where R=2'-deoxy-5-uridyl, m is 0 or 1, and n is an integer from 0 to 10.

Where appropriate, the compounds can be in any of their enantiomeric, diasteriomeric, or stereoisomeric forms, including, for example, D- or L-forms, and can be in any stereochemical configuration, including, for example, α- or β-anomeric form.

Synthesis of the above noted 5-substituted pyrimidine nucleosides and 5-substituted pyrimidine nucleoside monophosphates can be accomplished by methods that are well-known in the art. For example, treatment of 5-chloromercuri-2'-deoxyuridine with haloalkyl compounds, haloacetates or haloalkenes in the presence of $Li_2PdCl_4$ results in the formation, through an organopalladium intermediate, of the 5-alkyl, 5-acetyl or 5-alkene derivative, respectively. Wataya, et al. (1979) and Bergstrom, et al. (1981). Another example of C5-modification of pyrimidine nucleosides and nucleotides is the formation of C5-trans-styryl derivatives by treatment of unprotected nucleotide with mercuric acetate followed by addition of styrene or ring-substituted styrenes in the presence of $Li_2PdCl_4$. Bigge, et al. (1980). Pyrimidine deoxyribonucleoside triphosphates were derivatized with mercury at the 5 position of the pyrinmidine ring by treatment with mercuric acetate in acetate buffer at 50° for 3 hours. Dale, et al. (1973). Such treatment would also be expected to be effective for modification of monophosphates; alternatively, a modified triphosphate could be converted enzymatically to a modified monophosphate, for example, by controlled treatment with alkaline phosphatase followed by purification of monophosphate. Other moieties, organic or nonorganic, with molecular properties similar to mercury but with preferred pharmacological properties could be substituted. For general methods for synthesis of substituted pyrimidines, for example, U.S. Pat. Nos. 4,247,544; 4,267,171; and 4,948,882; and Bergstrom et al. (1981). The above methods would also be applicable to the synthesis of derivatives of 5-substituted pyrimidine nucleosides and nucleotides containing sugars other than ribose or 2'-deoxyribose, for example 2'-3'-dideoxyribose, arabinose, furanose, lyxose, pentose, hexose, heptose, and pyranose. An example of a 5-position substituent is the halovinyl group, e.g. E-5-(2-bromovinyl)-2'-deoxyuridylate. Barr, P. J. et al. (1983). This compound is synthesized as follows as described in the experimental section.

Alternatively, 5-bromodeoxyuridine, 5-iododeoxyuridine, and their monophosphate derivatives are available commercially from Glen Research, Sterling, Va. (USA), Sigma-Aldrich Corporation, St. Louis, Mo. (USA), Moravek Biochemicals, Inc., Brea, Calif. (USA), ICN, Costa Mesa, Calif. (USA) and New England Nuclear, Boston, Mass. (USA). Commercially-available 5-bromodeoxyuridine and 5-iododeoxyuridine can be converted to their monophosphates either chemically or enzymatically, though the action of a kinase enzyme using commercial available reagents from Glen Research, Sterling, Va. (USA) and ICN, Costa Mesa, Calif. (USA). These halogen derivatives could be combined with other substituents to create novel and more potent antimetabolites.

General Synthesis of Compounds of Class II

In a further aspect, the prodrug contacted with the cell overexpressing thymidylate synthase is an L or D isomer of a compound of the formula:

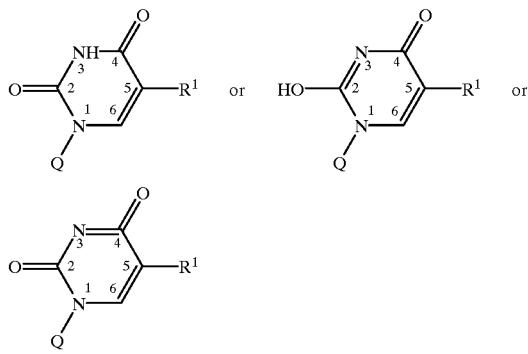

In the above formulae, $R^1$ is a moiety of the formula:

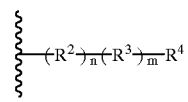

In the above formulae, $R^2$ is or contains a divalent electron conduit moiety. In one embodiment, $R^2$ is or contains a mono- or polyunsaturated electron conduit acting to conduct electrons away from the pyrimidine ring and toward the leaving group $R^1$. In one embodiment, $R^2$ is selected from the group consisting of: an unsaturated hydrocarbyl group; an aromatic hydrocarbyl group comprismg one or more unsaturated hydrocarbyl groups; and, a heteroaromatic group comprising one or more unsaturated hydrocarbyl groups.

In one embodiment, $R^2$ is an unsaturated hydrocarbyl group having a structure selected from the group consisting of:

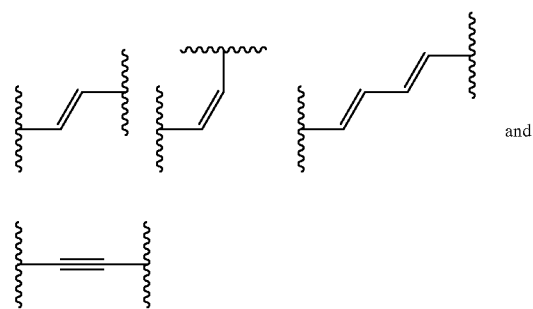

In one embodiment, $R^2$ and $R^3$, taken together form a structure selected from the group consisting of:

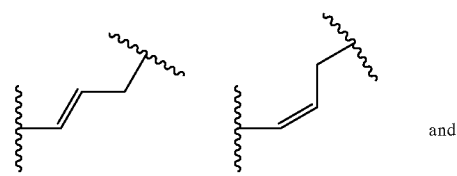

-continued

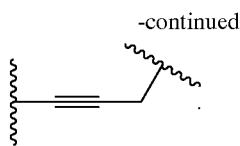

In one embodiment, R² is an aromatic hydrocarbyl group having a structure selected from the group consisting of:

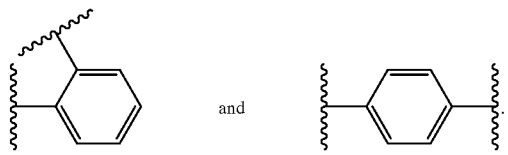

In one embodiment, R² is a heteroaromatic group having a structure selected from the group consisting of:

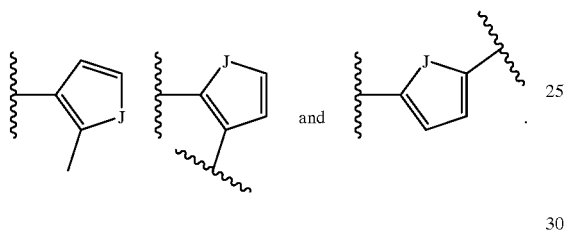

wherein J is a heteroatom, such as —O—, —S—, or —Se—, or a heteroatom group, such as —NH— or —NR$^{ALK}$-, where R$^{ALK}$ is a linear or branched alkyl having 1 to 10 carbon atoms or a cycloalkyl group having 3 to 10 carbon atoms.

In the above formulae, R³ is a divalent spacer moiety, also referred to as a spacer unit. In one embodiment, R³ is a divalent spacer moiety having a structure selected from the group consisting of:

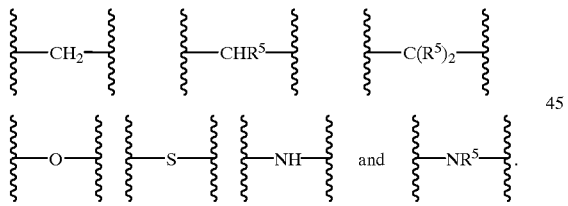

wherein R⁵ is the same or different and is independently a linear or branched alkyl group having from 1 to 10 carbon atoms, or a cycloalkyl group having from 3 to 10 carbon atoms.

In one embodiment, R³ is a divalent spacer moiety having a structure selected from the group consisting of:

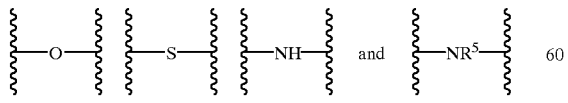

In the above formula, n is an integer from 0 to 10 and, m is 0 or 1. In one embodiment, n is an integer from 0 to 10 and, m is 1. In one embodiment, n is 0 and m is 0. In one embodiment, when R⁷ is —H, then n is not zero. In one embodiment, when R⁷ is —H, then m is not zero. In one embodiment, when R⁷ is —H, then n is not zero and m is not zero. In one embodiment, when R⁷ is —H, then R⁴ is not a halogen (i.e., —F, —Cl, —Br, —I). In one embodiment, when R⁷ is —H, and m is zero, then R⁴ is not a halogen (i.e., —F, —Cl, —Br, —I). In one embodiment, when R⁷ is —H, and m is zero and n is zero, then R⁴ is not a halogen (i.e., —F, —Cl, —Br, —I).

In the above formula, R⁴ is a toxophore moiety. As used herein, the term "toxophore" shall mean a moiety which is or contains a leaving group which is a chemical entity that has a molecular dimension and electrophilicity compatible with extraction from the pyrimidine ring by thymidylate synthase, and which upon release from the pyrimidine ring by thymidylate synthase, has the ability to inhibit the proliferation of the cell or kill the cell.

In one embodiment, the toxophore is or contains a leaving group that is activated or released by an intracellular enzyme overexpressed in the cell. In one embodiment, R⁴ is or contains a group having a structure selected from the group consisting of:

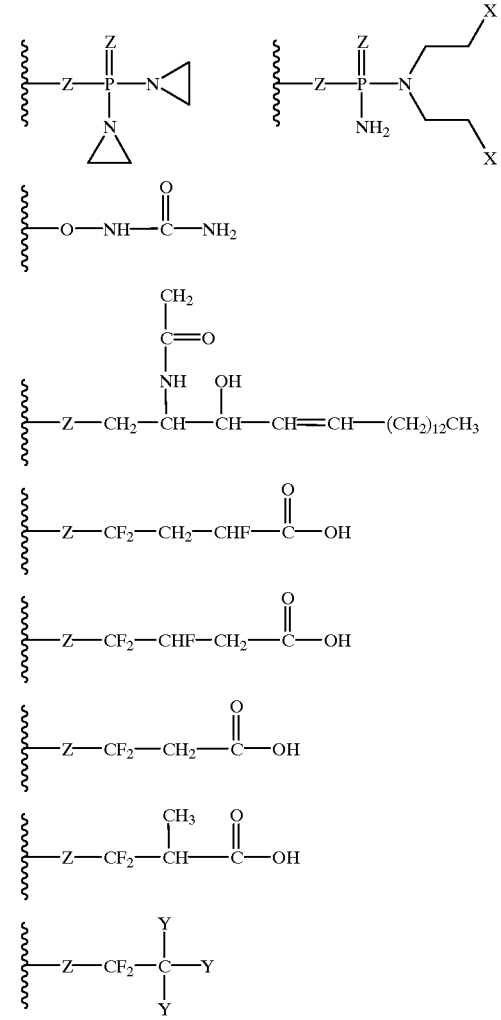

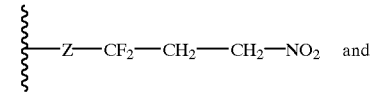

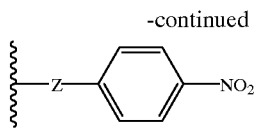

wherein X is —Cl, —Br, —I, or other potent leaving group (including, but not limited to, —CN, —OCN, and —SCN); Y is the same or different, and is independently —H or —F; and Z is the same or different and is independently —O— or —S—.

In one embodiment, $R^4$ is or contains a group having a structure selected from the group consisting of:

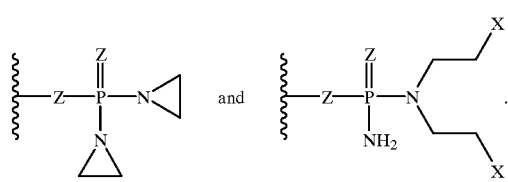

In one embodiment, $R^4$ is or contains a group having a structure selected from the group consisting of:

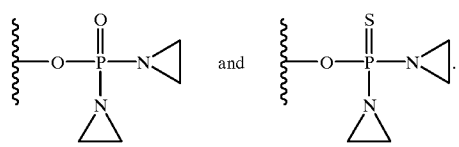

In one embodiment, $R^4$ is or contains a group having the structure:

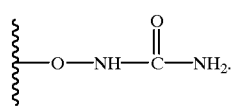

In one embodiment, $R^4$ is or contains a group having the structure:

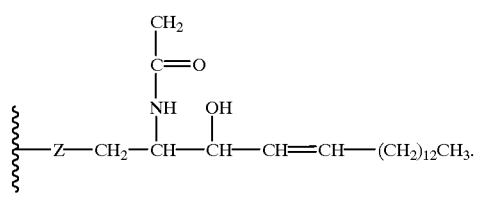

In one embodiment, $R^4$ is or contains a group having a structure selected from the group consisting of:

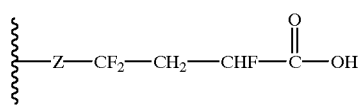

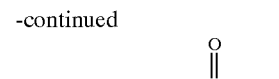

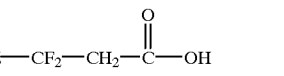

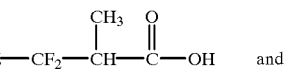

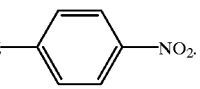

In one embodiment, $R^4$ is or contains a group having the structure:

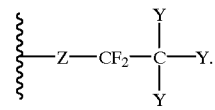

In one embodiment, $R^4$ is or contains a group having the structure:

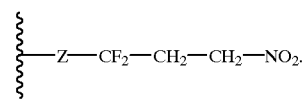

In one embodiment, $R^4$ is or contains a group having the structure:

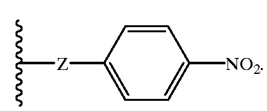

In one embodiment, $R^4$ is or contains a chemical entity selected from the group consisting of: —Br, —I, —O-alkyl, —-aryl, O-heteroaryl, —S-alkyl, —S-aryl, —S-heteroaryl, —CN, —OCN, —SCN, —NH$_2$, —NH-alkyl, —N(alkyl)$_2$, —NHCHO, —NHOH, —NHO-alkyl, NH$_2$CONHO—, NHNH$_2$, —N$_3$, and a derivative of cis-platin, such as:

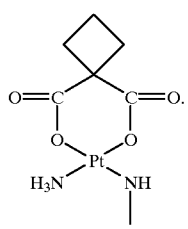

In the above formulae, Q is or contains a sugar moiety or a similar moiety which supports functional binding of the prodrug to the enzyme, e.g., TS or TK. In one embodiment, Q is selected from the group consisting of:

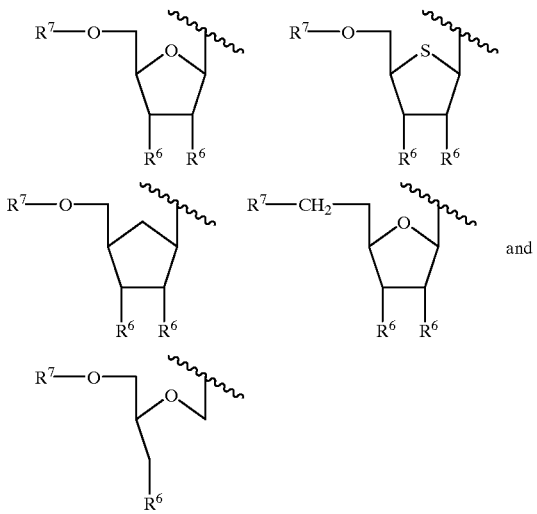

wherein $R^6$ is the same or different and is independently —H, —OH, —OC(=O)CH$_3$, or other protected hydroxyl group (including, but not limited to, benzoyl, —COC$_6$H$_5$, and toluoyl, —COC$_6$H$_4$CH$_3$); and, $R^7$ is hydrogen, a phosphate group, a phosphoramidate group, or other phosphorus containing group.

In one embodiment, Q is:

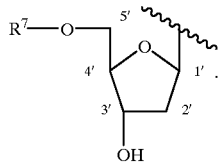

In one embodiment, Q is:

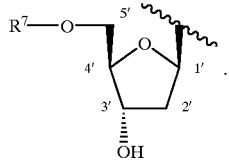

In one embodiment, $R^7$ is hydrogen. In one embodiment, $R^7$ is not hydrogen. In one embodiment, $R^7$ is a phosphate group or a phosphoramidate group. In one embodiment, $R^7$ is a phosphate group or a phosphoramidate group. In one embodiment, $R^7$ is a phosphoramidate group.

In one embodiment, $R^7$ is a phosphoramidate group derived from an amino acid, including, for example, the twenty naturally occuring amino acids. In one embodiment, $R^7$ is a phosphoramidate group derived from alanine. In one embodiment, $R^7$ is or contains a group having the structure:

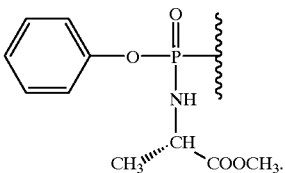

The above group, and methods for its preparation, are described in McGuigan et al. (1993), and McGuigan et al. (1996).

In one embodiment, $R^7$ is a phosphoramidate group derived from twptophan. In one embodiment, $R^7$ is or contains a group having the structure:

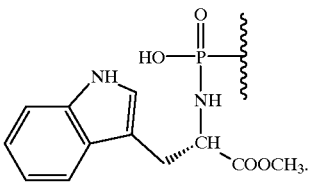

The above group, and methods for its preparation, are described in Abraham et al., (1996).

In one embodiment, $R^7$ is a phosphate group. In one embodiment, $R^7$ is or contains a group having a structure selected from the group consisting of:

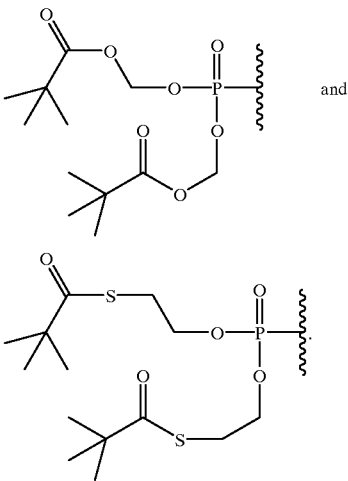

The first of the two above groups, and methods for its preparation, are described in Freed et al. (1989); Sastry et al., (992); Farquhar et al. (1994), and Farquhar et al. (1995). The second of the two above groups, and methods for its preparation, are described in Valette et al. (1996); and Benzaria et al. (1996).

In one embodiment, $R^7$ is or contains a group having a structure selected from the group consisting of (where R is an aromatic substituent):

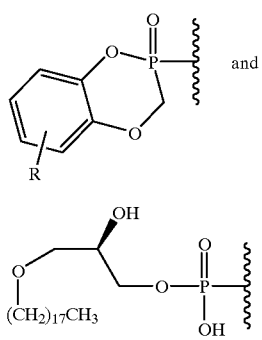

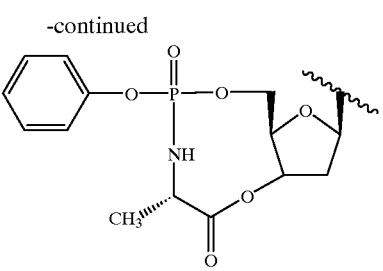

The first of the two above groups, and methods for its preparation, are described in Meier et al. (1997); Meier et al., (1997); and Meier et al., (1997). The second of the two above groups, and methods for its preparation, are described in Hostetler et al. (1997); and Hosteder et al., published International Patent Application No. WO 96/40088 (1996).

In one embodiment, the compound may be in any enantiomeric, diasteriomeric, or stereoisomeric form, including, D-form, L-form, α-anomeric form, and β-anomeric form.

In one embodiment, the compound may be in a salt form, or in a protected or prodrug form, or a combination thereof, for example, as a salt, an ether, or an ester.

In one embodiment, the $R^7$ forms a cyclic group within Q. One such embodiment, and a method for its preparation, is shown below (where DMTr is 4,4'-dimethoxytrityl, Boc is t-butyloxycarbonyl, DCC is 1,3-dicyclohexylcarbodiimide, and 4-DMAP is 4-dimethylaminopyridine):

In one embodiment, the prodrug is a compound of the formula:

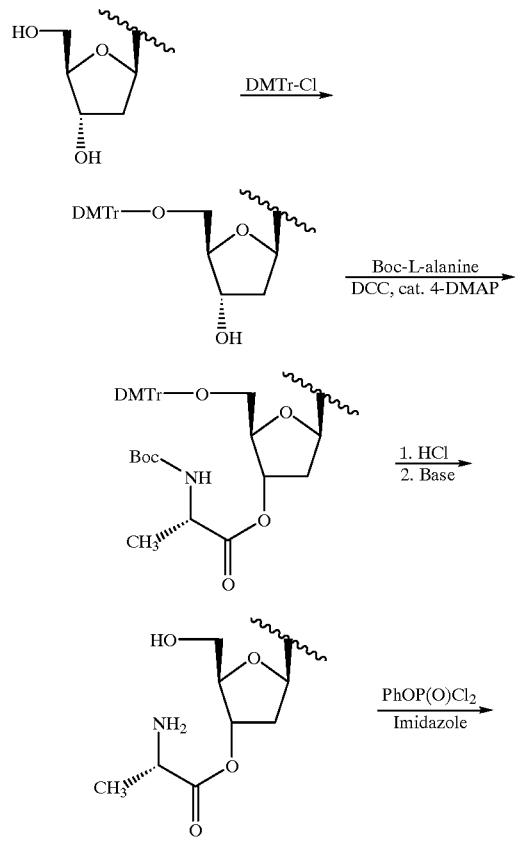

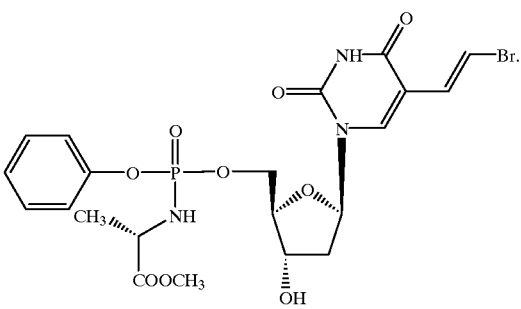

In one embodiment, the prodrug is a compound of the formula:

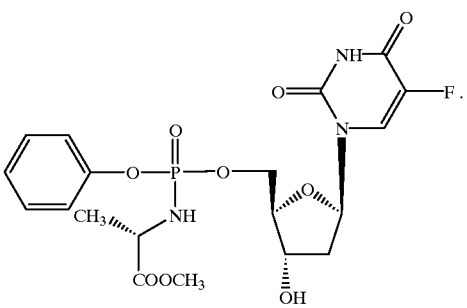

In one embodiment, the prodrug is a compound of the formula:

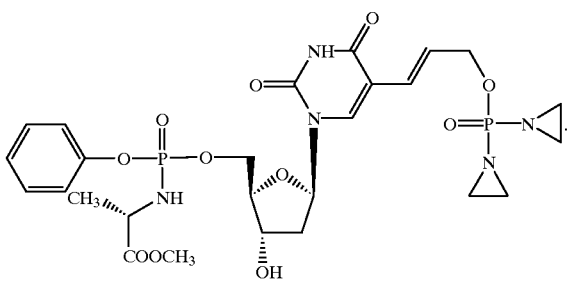

In one embodiment, the prodrug is a compound of the formula:

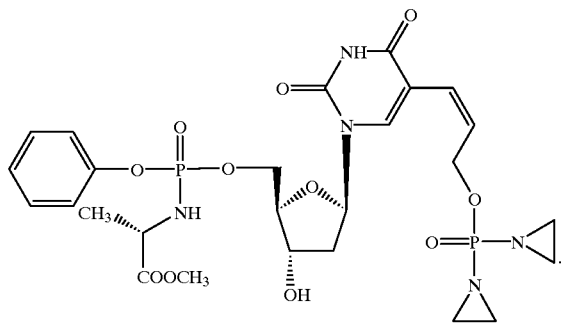

In one embodiment, the prodrug is a compound of the formula:

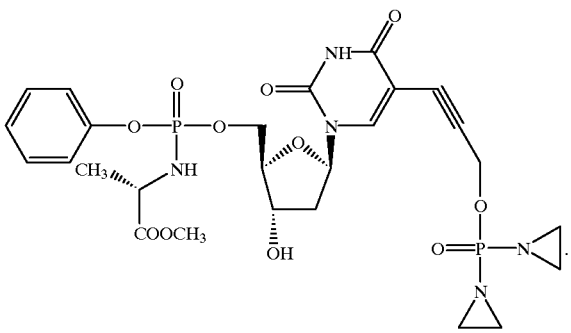

In a separate embodiment, the above structures are further modified to possess thiophosphodiaziridine instead of phosphodiaziridine groups, using the methods described below.

General Synthesis Strategy for Compounds of Class II

The structures at the 5-position of uracil are referred to as the tethers because they connect the proposed leaving group (toxophore) to the heterocycle. Upon activation of the heterocycle by reaction with Cys-195 in human TS, a negative charge is conducted from the 6-position of uracil into the tether. This mechanism has been described for the 5'-monophosphorylated versions of (E)5-(bromovinyl)-2'-deoxyuridine (BVDU) by Barr et al. (1983) and of (E)-5-(3,3,3-trifluoro-1-propenyl)-2'-deoxyuridine (TFPe-dUrd) by Wataya et al. (1979), Santi (1980), and Bergstrom et al. (1984).

The tether "spacer" between the toxin and dNMP must be unsaturated so that it can conduct the toxin-labilizing negative charge supplied by the TS-Cys-sulfhydryl attack. Of the many unsaturated organic functionalities available for this purpose, the vinyl, allyl, and propargyl units are simple, small, and readily accessible synthetically. The vinyl and allyl units have the advantage that they can be prepared in either of two non-interconvertible geometric isomeric forms. Thus, they can be used as "probes" of prodrug accommodation by the TS active site. On the other hand, the propargyl unit has the advantage of being cylindrically symmetrical, so that TS-catalyzed toxin release from this type of tether does not depend upon its orientation with respect to dUMP's uracil ring, as is the case with the vinyl and allyl molecules.

Two distinct approaches have been taken to design the nucleotide-based prodrugs of this invention. One is based on the structure of BVDU monophosphate and features a leaving group/toxin directly attached to the terminus of a (poly) vinyl substituent at C5 of dUMP. This is the vinyl tether approach. These compounds are defined in part as "Class I" compounds. The other is based on the structure of TFPe-dUMP and is similar to the first but has a methylene unit separating the leaving group/toxin and the unsaturated unit and thus contains an allyl or propargyl unit, described below as "Class II". This is the allyl tether approach.

Structures for 5'-phosphoramidate versions of each type are shown below:

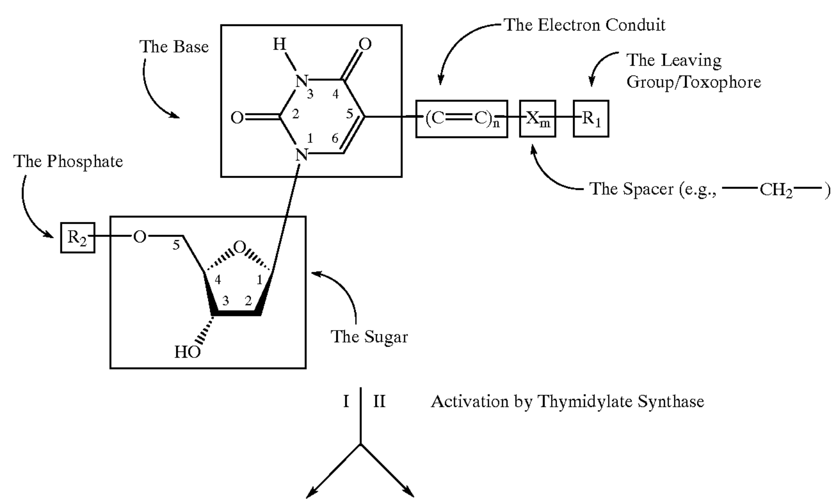

-continued

```
The activated nucleoside          Released toxophore attacks
   rearranges to give toxic          intracellular target
product (e.g., modified dNMP)
         /        \                    /        \
   Nucleic Acid  Other Intracellular Target   Mitochondria  Other Pleiotropic Cell Target
```

The mechanism of activation of a propargyl version of the allyl tether approach has a precedent in the interaction of both 5-ethynyl-2'-deoxyuridine 5'-monophosphate (EdUMP) and 5-(3-hydroxy-1-propynyl)-2'deoxyuridine 5'-monophosphate (HOPdUMP) with TS (Barr et al. 1981, Barr and Robins 1983). EdUMP is a potent inhibitor of TS (Ki=0.1 $\mu$M), and likely forms an allene-based species at the active site. HOPdUMP (Ki=3.0 $\mu$M) shows unusual inhibition kinetics, which might be due to formation of a cumulene-based species at the active site.

5-Alkylidenated 5,6-dihydrouracils similar in structure to the intermediate common to both the vinyl and allyl tether approach mechanisms have been synthesized recently (Anglada et al. 1996). These were shown to be highly electrophilic. Their ready reaction with ethanol to generate 5-(ethoxymethyl)uracils is a precedent for the water addition that regenerates catalytically competent TS in the mechanisms shown in FIG. 8. Even more recently, the existence of the long-elusive C5 methylene intermediate produced by TS was demonstrated by trapping studies (Barrett et al. (1998)).

The synthesis of C5 propargylic and allylic alcohol-equipped 2'-deoxyuridines is straightforward. Many of these and their close derivatives are reported in the literature, and some have even been studied in connection with TS. For example, 5-alkynyl-dUMPs including the 5-(3-methoxy-1-propynyl) and 5-(3-hydroxy4-propynyl) ones have been examined as TS inhibitors (Barr et al. (1981)) and some of these have been shown to become incorporated into the DNA of TS-deficient cancer cells (Balzarini et al. (1985)).

Both 5-mercuri- (Ruth et al. (1978)) and 5-iodouridines (Robins et al. (1981)) readily condense with alkenes and alkynes in the presence of a palladium catalyst to afford C5 tether-equipped uridines. The latter route is the more often employed (Robins et al. (1982)), Asakura and Robins (1988) and (1990)). High-yielding condensations of protected 5-iodo-2'-deoxyuridines with t-butyidimethylsilyl propargyl ether (Graham et al. (1998) De Clercq et al. (1983), methyl propargyl ether (Tolstikov et al. (1997)) and even propargyl alcohol itself(Chaudhuri et al. (1995) Goodwin et al. (1993)) have been achieved. The 3-hydroxy-l-propynyl substituent introduced by the latter reaction can also be accessed by DIBAL-H reduction of a methacrylate group (Cho et al. (1994)), itself arising from the same Heck reaction used in the synthesis of BVDU. These palladium-catalyzed reactions are so versatile that they can used to condense very long and elaborately-functionalized propargyl-based tethers to 5-iodo-2'-deoxyuridines (Livak et al. (1992) Hobbs (1989)). (Z)-Allyl-based tethers are generated by the partial hydrogenation of a propargylic precursor over Undiar catalyst (Robins and Barr (1983)) whereas the (E)-allyl-based ones are best prepared by Heck coupling of an (E)-tributylstannylated ethylene (Crisp (1989)).

Closely following the literature procedures, a t-butyldimethylsilyl propargyl ether-equipped 3', 5'-di-O-protected 2'-deoxyuridine (Graham et al. (1998), De Clercq et al. (1983)) is prepared and a portion of it converted to the corresponding (Z)-allyl ether (Robins and Barr (1983)) is reduced. Because the TBAF-mediated removal of a TBDMS group generates an oxyanion that ran be functionalized in situ, these TBDMS-protected propargyl- and (Z)-allytic-tethered nucleosides will serve as convenient precursors to some of the toxophore-equipped targets. For the (E)-allyl alcohol equipped nucleoside, the known O-tetrahydropyranyl ether derivative is prepared by the literature Heck coupling of an (E)-tributylstannylated ethylene (Crisp (1989)).

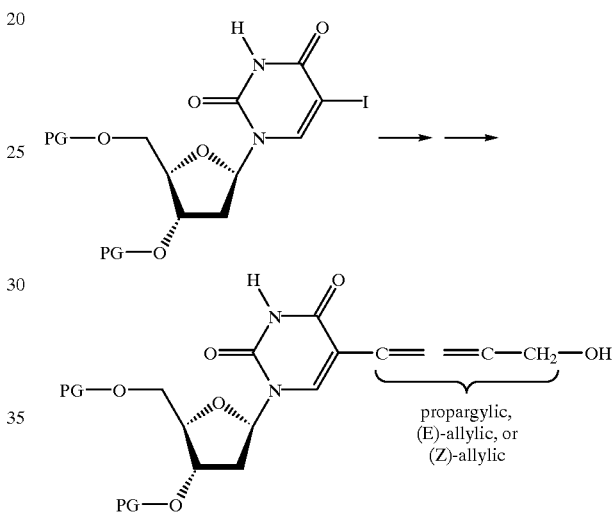

Using a two step literature protocol (Phelps et al. (1980) Hsiao and Bardos (1981)), the propargylic and (E) and (Z)-allylic alcohols are converted to their corresponding bis-aziridinyl phosphoramidates or thiophosphoramidates so that TS processing of the 5'-mononucleotide versions will release an active metabolite of the cytostatic drugs TEPA or ThioTEPA (Dirven et al. (1995)), respectively.

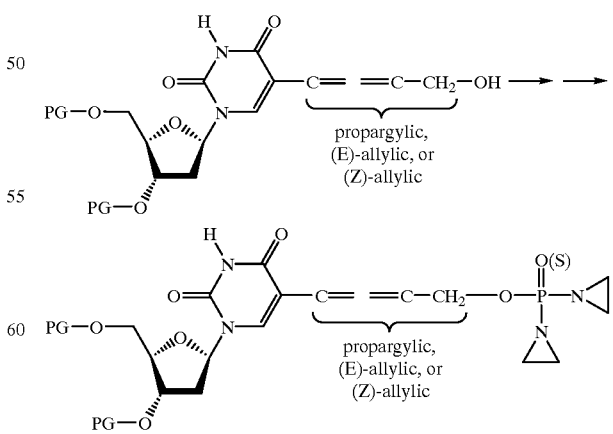

To avoid the potential hydrolytic lability of esters derived from the propargylic or allylic alcohols, the carboxylic acid moiety of toxophores like 3-nitroproprionic acid is "masked" by attaching them to the alcohol as α,α-difluoro ethers. To do this, a propargyl or allyl thioester tether is first prepared by treating the normal ester with Lawesson's reagent (Cava and Levinson (1985)), and then converting the thioester to the α,α-difluoro ether in an established fashion with tetrabutylammonium dihydrogentrifluoride (Kuroboshi and Hiyama (1991) and (1994)). The α,α-difluoro ether-based tether is then condensed with a protected 5-iodo-2'-deoxyuridine as usual. As an α,α-difluoro ether, the masked toxophore will be stable until TS releases it as a latent reactive acyl fluoride. The ensuing rapid hydrolysis will generate the carboxylic acid-based toxophore in situ.

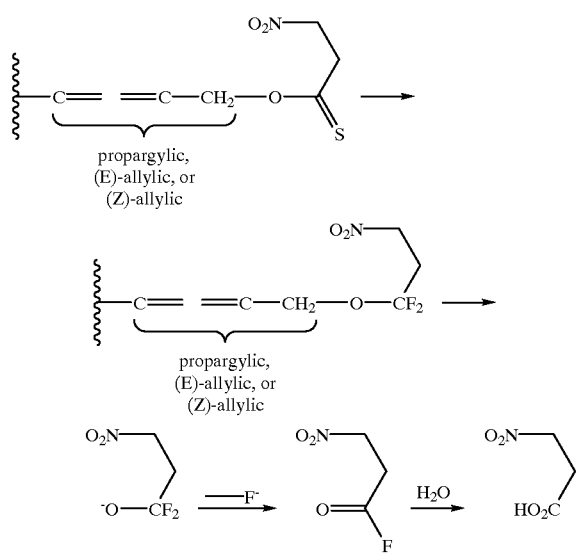

p-Nitrophenyl ether derivatives of the CS propargylic and (E) and (Z)-allylic alcohol-equipped 2'-deoxyuridines provide good reagents for in vitro TS enzyme assays, because the spectrophotometric, kinetic determination of released p-nitrophenol will identify those tethered dUMP platforms that bind to TS in a manner that permits facile catalytic release of a leaving group from the end of the tether. The needed p-nitrophenyl ethers will be obtained either directly from the alcohols by a base-catalyzed condensation with 4-fluoronitrobenzene or de novo by a Heck coupling of an appropriate p-nitrophenyl propargyl or allyl ether. The 5'-monophosphates needed for the TS assay are generated from the nucleosides either enzymatically or chemically according to a well-established regioselective 5'-monophosphorylation protocol (Imai et al. (1969)).

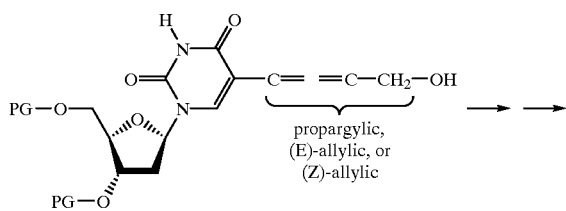

-continued

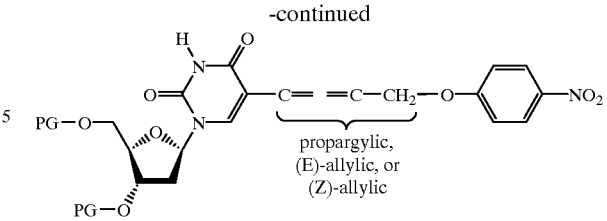

Many 5-substituted 2'-deoxyuridines are not substrates for human TK, but interestingly 5-(4-hydroxy-1-butynyl)-2'-deoxyuridine was found to be an exception (Barr et al. (1981)). Thus, it is expected that some of the toxophore equipped nucleosides will also possess propitious TK substrate activity, and so they will be examined for activity against tumor cell growth. Still, the preparation of the 5'-phosphoramidates is now a simple matter according to this newly developed regioselective procedure, and so these pro-prodrug versions are prepared and tested as well.

Cominatorial Synthesis

Figure 6:
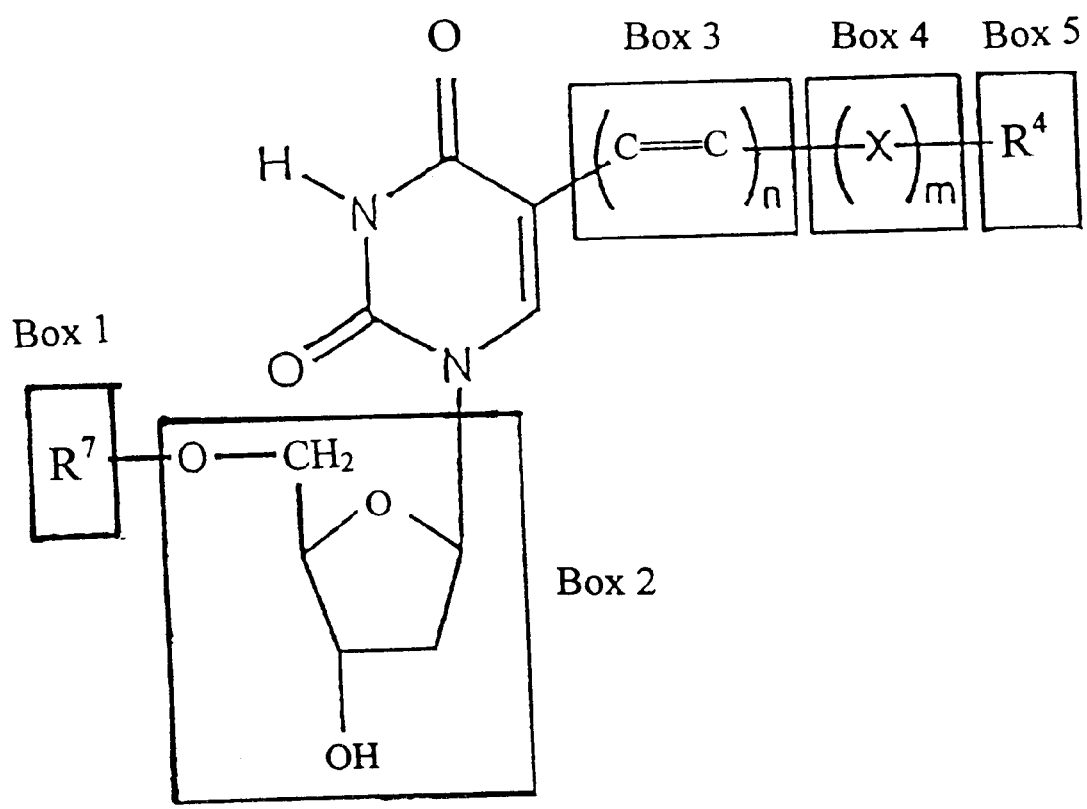
FIG. 6 shows one embodiment of a multi partitioned substrate for the generation of a thymidylate synthase (TS)-activatable prodrug.

A rapid way to achieve a lead compound is through the use of combinatorial chemistry methodologies. Because a great deal is known about the mechanism of action of the thymidylate synthase enzyme (Schiffer, et al. (1995)), the following issues are anticipated: cellular entry by the prodrug, phosphorylation of the prodrug by thymidine kinase, and conversion from prodrug (uridine derivative) to active drug by thymidylate synthase. With respect to cellular entry, modifications of a phosphorylated nucleotide may be employed (see, for example, U.S. Pat. Nos. 5,233,031 and 5,627,165). In addition, preferential phosphorylation of the prodrug in tumor cells is facilitated as a result of overexpression of thymidine kinase in most tumor cells as a result of tumor suppressor gene loss (Hengstschlager et al. (1996)). Similarly, preferential activation of the phosphorylated prodrug or phosphoramidate derivative will occur in tumor cells because of the overexpression of thymidylate synthase accompanying tumor suppressor loss (Li, W. et al. (1995)) and chemotherapy (Peters, G. J. et al. (1995)). Combinatorial chemistry targeting the 5-position of the uridine ring (from which the cell toxin may be generated), or the 5'-position of the pentose sugar (to facilitate binding to thymidylate synthase), will greatly expedite the discovery of lead compounds by optimizing the structure of the leaving group (cell toxin) from the uridine ring, as well as facilitating optimization of a phosphorylation competent group at the 5'-position of the pentose sugar. For purposes of the screen shown in FIGS. 3, 4 and 5, the chemical entity being tested will be generated by either a single site directed chemistry (FIG. 4), or simultaneously at two sites on the molecule (FIG. 5). Together with the screen shown in FIG. 3, a powerful system for discovery of prodrugs targeting thymidylate synthase has been developed. The combinatorial chemistry approach used will be similar to that described in Lam, K. S. (1997). In one embodiment, prodrugs that provide toxic leaving groups are shown in FIG. 6. The uridine substrates shown in FIG. 6 take advantage of phosphoramidase (present in all cells) and elevated thymidylate synthase (TS) in tumor cells. As is understood by those of skill in the art, this rationalized drug design can be broadly applied to the synthesis of other prodrugs as defined herein.

It should be understood by those skilled in the art that the screen shown in FIG. 3 can be applied broadly for the discovery of antibiotics. For example, thymidylate synthase from yeast could be substituted for that of E. coli in FIG. 4. This would allow the discovery of specific antifungal antibiotics targeting yeast related pathogens. In addition, other enzymes can be subjected to this treatment. For example, prodrugs which target specifically the dihydrofolate reductase activity of infectious agents, like *Pneumocystis carnii*, could be selected. These agents will be selected for specificity for the target enzyme, and can be shown not to activate the enzyme of the natural host by employing the screening assay described in FIG. 3. The control cellular constructs would contain the corresponding normal human enzyme, in order to show lack of toxicity when only the normal human enzyme is present.

The drugs or agents of the invention or as described herein can be made more permeable, for example across cell membranes and across the blood-brain barrier, by means of various chemical modifications. These would include attachment, to their phosphate moiety, of various functional groups which improve membrane permeability. Such functional groups include, but are not limited to, those described in U.S. Pat. Nos. 5,233,031 and 5,627,165; Fries, K. M., et al. (1995) and McGuigan, C., et al. (1984). Certain phosphoramidate derivatives of dideoxyuridine (ddU) are active against HIV and successfully bypass thymidine kinase. McGuigan, C., et al. (1984). Such chemical modifications can also serve to protect substituted pyrimidine monophosphate derivatives from the action of cellular and extracellular phosphatases. While the mercury or halogen derivatives may be effective, it is expected that modifications that release alkylating or antimetabolic compounds will be preferred. A preferred embodiment is shown in FIG. 6.

Derivatives of the Compounds of Class I and II

Salts, esters, and ethers of the above compounds disclosed herein are also within the scope of this invention. Salts of the prodrugs of the present invention may be derived from inorganic or organic acids and bases. Examples of acids include hydrochloric, hydrobromic, sulfuric, nitric, perchloric, fumaric, maleic, phosphoric, glycollic, lactic, salicyclic, succinic, toluene-p-sulfonic, tartaric, acetic, citric, methanesulfonic, ethanesulfonic, formic, benzoic, malonic, naphthalene-2-sulfonic and benzenesulfonic acids. Other acids, such as oxalic, while not in themselves pharmaceutically acceptable, can be employed in the preparation of salts useful as intermediates in obtaining the compounds of the invention and their pharmaceutically acceptable acid addition salts. Examples of bases include alkali metal (e.g., sodium) hydroxides, alkaline earth metal (e.g., magnesium) hydroxides, ammonia, and compounds of formula $NW_4^+$, wherein W is $C_{1-4}$ alkyl.

Examples of salts include: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, palmoate, pectinate, persulfate, phenylproprionate, picrate, pivalate, propionate, succinate, tartrate, thiocyanate, tosylate and undecanoate. Other examples of salts include anions of the compounds of the present invention compounded with a suitable cation such as $Na^+$, $NH_4^+$, and $NW_4^+$ (wherein W is a $C_{1-4}$ alkyl group).

For therapeutic use, salts of the compounds of the present invention will be pharmaceutically acceptable. However, salts of acids and bases which are non-pharmaceutically acceptable may also find use, for example, in the preparation or purification of a pharmaceutically acceptable compound.

Esters of the prodrugs or compounds identified by the method of this invention include carboxylic acid esters (i.e., —O—C(=O)R) obtained by esterification of the 2'-, 3'-and/or 5'-hydroxy groups, in which R is selected from (1) straight or branched chain alkyl (for example, n-propyl, t-butyl, or n-butyl), alkoxyalkyl (for example, methoxymethyl), aralkyl (for example, benzyl), aryloxyalkyl (for example, phenoxymethyl), aryl (for example, phenyl optionally substituted by, for example, halogen, $C_{1-4}$alkyl, or $C_{1-4}$alkoxy or amino); (2) sulfonate esters, such as alkylsulfonyl (for example, methanesulfonyl) or aralkylsulfonyl; (3) amino acid esters (for example, L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di-$(C_{6-24})$acyl glycerol. In such esters, unless otherwise specified, any alkyl moiety present advantageously-contains from 1 to 18 carbon atoms, particularly from 1 to 6 carbon atoms, more particularly from 1 to 4 carbon atoms. Any cycloalkyl moiety present in such esters advantageously contains from 3 to 6 carbon atoms. Any aryl moiety present in such esters advantageously comprises a phenyl group. Examples of lyxo-furanosyl prodrug derivatives of the present invention include, for example, those with chemically protected hydroxyl groups (e.g., with O-acetyl groups), such as 2'-O-acetyl-lyxo-furanosyl; 3'-O-acetyl-lyxo-furanosyl; 5'-O-acetyl-lyxo-furanosyl; 2',3'-di-O-acetyl-lyxo-furanosyl and 2',3',5'-tri-O-acetyl-lyxo-furanosyl.

Ethers of the compounds of the present invention include methyl, ethyl, propyl, butyl, isobutyl, and sec-butyl ethers.

In a further embodiment, the substrate may not be chemically related to pyrimidines or folates, but rather synthesized based upon known parameters of rational drug design. See Dunn, W. J. et al. (1996).

Chemical assays for products, for example, where a reaction product is an anti-metabolite of the bromovinyl-derivatives of dUMP, are described in the Examples provided below or by Barr, P. J. et al. (1983).

Diagnostic Application

Another aspect of the present invention pertains to the methods for screening for a therapeutic agent, comprising contacting a target cell with a prodrug compound this invention.

In the embodiment, the prodrug is a compound to the group of Class II, as described below, wherein $R^4$ is:

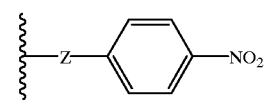

which target cell favor the incorporation of the compound into the target cell, for the diagnostic purpose of detecting intracellular levels of thymidylate synthase.

EXAMPLES

The following examples are specifically directed to the target enzyme TS. It is apparent to those skilled in the art that the following methods can be modified for the discovery of other prodrugs to target enzymes as defined herein, or used as a controlin the discovery of other prodrugs for TS and another intracellular enzymes.

Synthesis of Prodrugs

A phosphoramidate derivative of 5-fluoro-2'-deoxyuridine (5-FUdR), and (E)-5-(2-bromovinyl)-2'-deoxyuridine (BVDU) and a phosphoramidate derivative of BVDU were synthesized.

BVDU was prepared from 2'-deoxyuridine according to a literature procedure (Dyer, et al. (1991)). According to standard methods, it was first protected at the O5' position with a dimethoxytrityl (DMTr) group and then at the O3' position with a tertbutyldimethylsilyl (TBDMS) group, and then the 5'-O-DMTr group was removed by treatment with acid (see below).

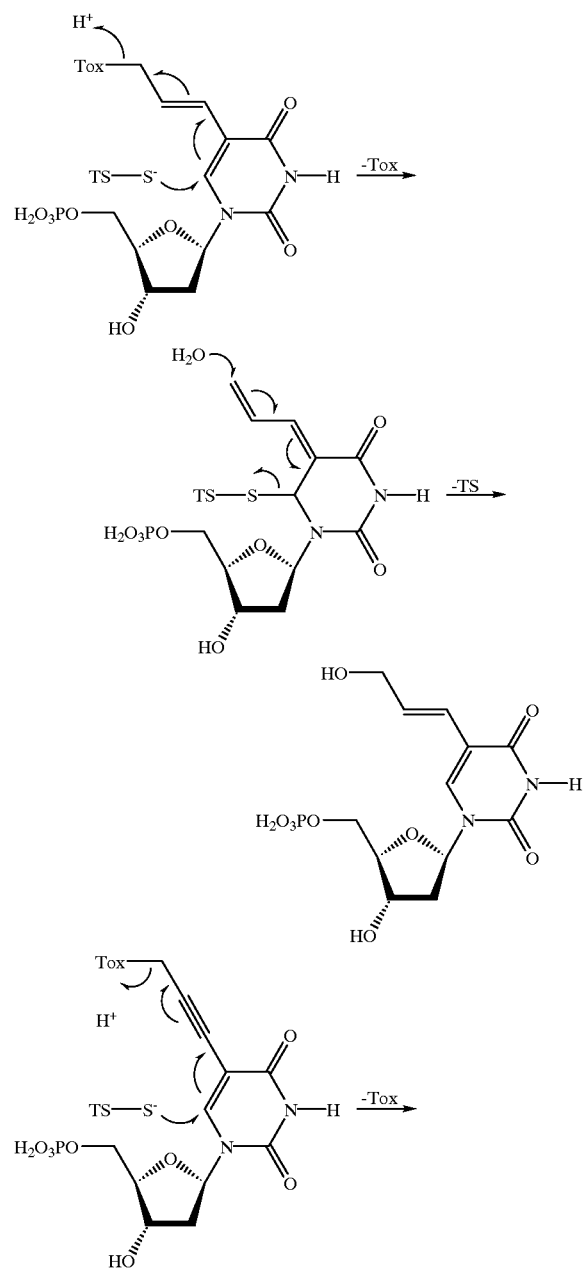

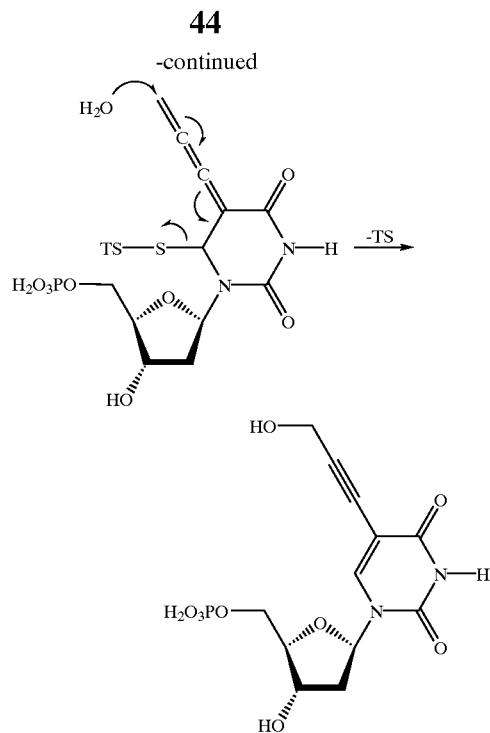

The 3'-O-TBDMS-protected nucleoside thus obtained reacted with phenyl L-methoxyalaninyl phosphorochloridate (PMPC) McGuigan, et al. (1992)) to give the 3'-O-TBDMS-protected BVDU-PA. However, unexpectedly, the phosphoramidate functionality was found to be labile to the very mild desilylation conditions of tetrabutylammonium fluoride (TBAF) on silica gel, by $^1$H nuclear magnetic resonance (NMR) spectroscopy. This observation of a sensitivity to mildly basic conditions provides one possible explanation why, save for one arabinonucleoside (McGuigan, et al. (1998)), all of the nucleoside 5'-phosphoramidate derivatives reported to date have lacked a 3'-hydroxy group functionality (see e.g., McGuigan, et al. (1996); McGuigan, et al. (1993); McGuigan, et al. (1994), Balzarini, et al. (1997), Balzarini, et al. (1996)). A novel synthetic method was developed to solve this problem.

To synthesize (E)-5-(Bromovinyl)-2'-deoxy-5'-uridyl phenyl L-alaninylphosphoramidate (BVDU-PA), a solution of BVDU (420 mg, 1.26 mmol) in 2 mL of anhydrous DMF under argon was treated with imidazole (103 mg, 1.51 mmol) and then dropwise with phenyl L-methoxyalaninyl phosphorochloridate (350 mg, 1.26 mmol (McGuigan, et al. (1992)). The reaction mixture was stirred at 23° C. under argon for 24 hours. By TLC on silica gel using 10% methanol in dichloromethane as eluent, the generation of BVDU-PA ($R_f$ 0.70) from BVDU ($R_f$ 0.53) had occurred, but only to a partial extent (ca. 15%), and so additional imidazole (52 mg, 0.75 mmol) and PMPC reagent (175 mg, 0.63 mmol) was added and the mixture stirred again at 23° C. under argon for 12 hours. By TLC, the progress of the reaction had increased somewhat (ca. 30% complete). The solution was reduced in volume to 0.75 mL by rotary evaporation and then was diluted with an equal volume of dichloromethane and was applied directly to a dry 4 mm silica gel Chromatotron plate. Radial chromatography using 250 mL of dichloromethane to elute residual DMF followed by 10% methanol in dichloromethane to elute product and starting material gave 144 mg (20%) of BVDU-PA and 294 mg of unreacted BVDU, for a 67% yield of BVDU-PA based on unrecovered starting material. If the $^1$H NMR spectrum of product revealed the presence of imidazole (δ7.65 and 7.01) or DMF (δ7.95, 2.89, and 2.73), an additional radial chromatographic purification was performed. In this way, BVDU-PA with a purity of at least 98% by TLC and $^1$H NMR was obtained as an oil or a foam-powder. $^1$H NMR ((CD$_3$)$_2$SO) δ11.4 (bs, exchanges with D$_2$O, 1, 3'OH), 8.28 (t, 1, H6), 7.35 (m, 2, Ph), 7.31 (d, 1, vinyl 1H), 7.20 (m, 3, Ph), 6.89 (d, 1, vinyl 2H), 6.19 (pseudo-t, 1, H1'), 6.08 (t, exchanges with D$_2$O, 1, alaninyl NH), 5.45 (bs, exchanges with D$_2$O, 1, 3'OH), 4.32 (m, 1, H4'), 4.22 (m, 2, 5'CH$_2$), 3.97 (m, 1, H3'), 3.86 (t, 1, alaninyl CH), 3.58 (s, 3, CO$_2$Me), 2.15 (m, 2, 2'CH$_2$), 1.23 (t, 3, alaninyl CH$_3$). $J_{vinyl\ CH-vinyl\ CH}$=13.5, $J_{H1'-H2'}$~6.8, $J_{H2'-H3'}$~5, $J_{H3'-H4'}$~0, alaCH-Ala-NH$_3$ NH~6 Hz. $^1$H/$^1$H COSY 2D NMR spectroscopy provided confirmation of spectral assignments.

In a similar fashion, 5-Fluoro-2'-deoxy-5'-uridyl phenyl L-alaninylphosphoramidate (5FUdR-PA), was obtained in a purity of at least 98%, by TLC and $^1$H NMR. $^1$H NMR ((CD$_3$)$_2$SO)δ11.9 (bs, exchanges with D$_2$O, 1, N3H), 7.88 (t, 1, H6), 7.36 (m, 2, Ph), 7.19 (m, 3, Ph), 6.15 (pseudo-t, 1, H1'), 6.07 (t, exchanges with D$_2$O, 1, alaninyl NH), 5.42 (bs, exchanges with D$_2$O, 1, 3'OH), 4.21 (m, 3, H4' and 5'CH2), 3.98 (m, 1, H3'), 3.84 (t, 1, alaninyl CH), 3.58 (s, 3, CO$_2$Me), 2.08 (m, 2, 2'CH$_2$), 1.22 (t, 3, alaninyl CH3). $J_{H6-5F}$=7.1, $J_{H1'-H2'}$~5.2, $J_{H2'-H3'}$~2, $J_{H3'-H4'}$~0, $J_{alaninyl\ CH-alaninyl\ NH}$~6 Hz. $^1$H/$^1$H COSY 2D NMR spectroscopy provided confirmation of spectral assignments. Low-resolution mass spectrum (DCI-NH3), m/z 505 (MNH$_4$+), 488 (MH+).

It was reasoned that the direct condensation of an unprotected 2'-deoxyribonucleoside with PMPC might very well proceed to give the desired phosphoramidate and in a 5'-O-regioselective manner if it were conducted in the absence of base but the presence of a scavenger for the HCl produced. Both BVDU and 5FUdR condensed with the McGuigan reagent in the presence of imidazole in anhydrous DMF solution to give the desired BVDU-PA and 5FUdR-PA, respectively (see below). The reaction conditions have not been optimized, and although the reactions do not proceed to completion, the readily separable product mixture in both cases consists largely of only desired product and starting material, by thin layer chromatography (TLC). The synthetic scheme is summarized below.

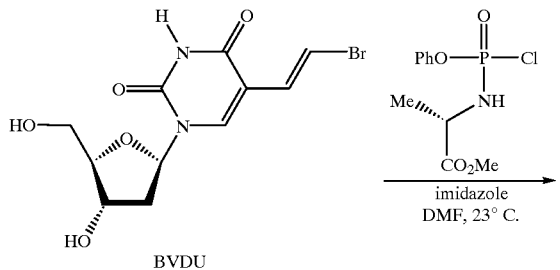

BVDU

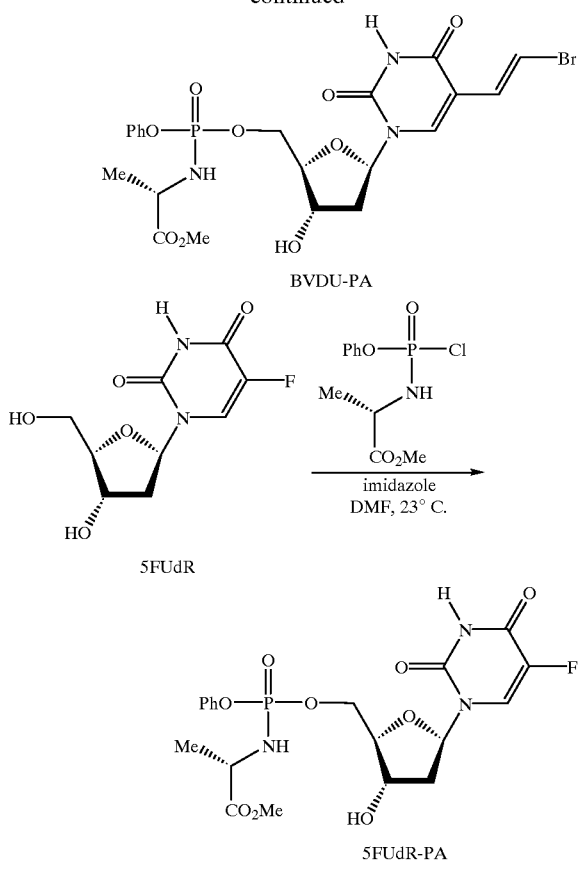

(E)-5-(Bromovinyl)-2'-deoxy-5'-uridyl phenyl L-alaninylphosphoramidate (BVDU-PA).

TLC monitoring (10% methanol in dichloromethane as eluent) revealed the production of BVDU-PA (R$_f$0.70) from BVDU (R$_f$0.53). In this way, BVDU-PA was obtained in a purity of at least 98%, by TLC and $^1$H NMR. $^1$H NMR ((CD$_3$)$_2$SO). A $^1$H/$^1$H COSY 2D NMR spectrum confirmed the spectral assignments. Low-resolution mass spectrum by direct chemical ionization (DCI) using NH$_3$, m/z 593/591 (M·NH$_4^+$), 576/574 (M·H+).

5-Fluoro-2'-deoxy-5'-uridyl phenyl L-alaninylphosphoramidate (5FUdR-PA). In a similar fashion, 5FUdR-PA was obtained in a purity of at least 98%, by TLC and $^1$H NMR. $^1$H NMR ((CD$_3$)$_2$SO). A $^1$H/$^1$H COSY 2D NMR.spectrum confirmed the spectral assignments. Low-resolution mass spectrm (DCI-NH$_3$), m/z 505 (M·NH$_4^+$), 488 (M·H+).

Thus, one aspect of the invention pertains to methods of preparing a 2'-deoxy, 3'-hydroxy, 5'-phosphoramidate of a furanosyl nucleoside, which methods involve reacting an unprotected furanosyl nucleoside which is 2'-deoxy, 3'-hydroxy, and 5'-hydroxy, with a phosphochloridate in the presence of an HCl scavenger. In one embodiment, the phosphochloridate comprises a phosphorus substituent which is derived from an amino acid, such as alanine. In one embodiment, the phosphochloridate is phenyl-L-methoxyalanine phosphorochloridate. Thus, in a firther embodiment, the present invention pertains to a method of forming a compound of the formula:

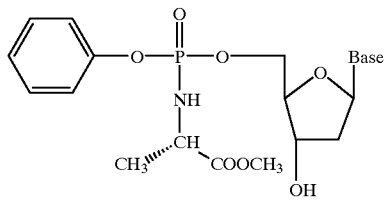

wherein "Base" denotes a nucleic acid base (such as uracil, thymine, cytosine, adenine, or guanine, but preferably uracil, or a derivative thereof); which method comprises the step of reacting a compound of the formula:

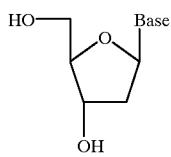

with a compound of the formula:

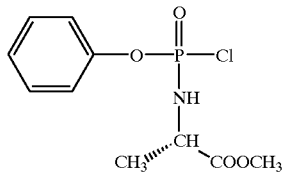

in the presence of an HCl scavenger.

In one embodiment, the furanosyl nucleoside is a uridine nucleoside. In another embodiment, the furanosyl nucleoside is a uridine ribofuranosyl nucleoside. In another embodiment, the furanosyl nucleoside is a uridine β-D-ribofuranosyl nucleoside. Thus, in one embodiment, the present invention pertains to a method of forming a compound of the formula:

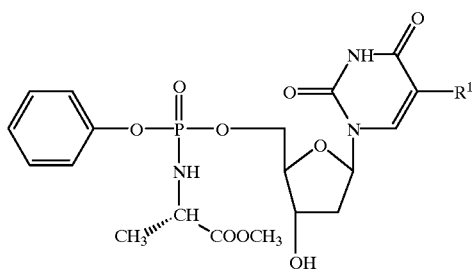

wherein $R^1$ is a substituent (including, for example, those described above for $R^1$); which method comprises the step of reacting a compound of the formula:

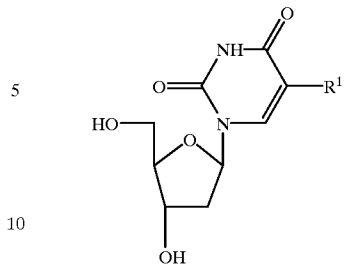

with a compound of the formula:

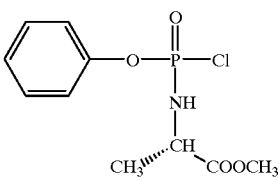

in the presence of an HCl scavenger.

In one embodiment, the reaction is performed in the absence of base, but in the presence of an HCl scavenger, such as imidazole. In an alternate embodiment, the reaction is carried out in a non-aqueous medium. In another embodiment, the reaction is carried out in a non-aqueous medium comprising anhydrous dimethylformamide (DMF).

Chemical and Cell-Based Assays

Two cell lines, H630R10 (Copur, et al. (1995)) and normal colon epithelial cells, CCD18co (ATCC) were used in these assays. The H630P (Copur et al. (1995)) cell line was selected for resistance to 10 μM 5-FU to give rise to H630R10. The characterization of these cell lines which expresses an elevated level of the TS enzyme. A normal colon epithelial cell type CCD18co (available from the ATCC) was used for comparison with H630R10 for sensitivity to test compounds. Cell lines expressing p185-HER2 or neomycin marker alone were prepared as described by Pegram et al. (1997) shows that H630R and H630R10 expresses 10 fold increased thymidylate synthase enzyme as compared with CCD18co as determined by Western blot analysis.

The ability of the test compounds to block proliferation of cells was determined by the crystal violet procedure (Sugarman et al. (1985) and Antelman et al. (1995)). Compounds were dissolved in dimethyl sulfoxide to a concentration of 1M. They were further diluted as necessary into DMEM cell culture medium, and subsequently into the first wells of the 96 Well microtiter plate. Each concentration was tested in triplicate on the target cell line. Compound concentrations from 1 μM to 3000 μM were tested. Cells were incubated with compound for 72 hours, the plates were washed, and the cells fixed with methanol and stained with crystal violet as described in Sugarman et al. (1995) and Antelman, et al. (1995).

Western Blot Analysis of TS Levels in Cell Lines

Western blot experiments were performed with the human normal colon epithelium cell type CCD18co (obtained from ATCC, Manassas, Va.), colon adenocarcinoma cell line H630R10 (obtained from Dr. S. Copur, Yale University), and HER2-transfected breast cancer cell lines (Pegram et al. (1997)). Cells were lysed in RIPA buffer (50 mM Tris-HCl, pH 7.5,150 mM NaCl, 0.5% Triton X-100, 0.1% SDS and 0.5% Deoxycholic acid, sodium salt and protease inhibitors). Protein concentrations were determined by using BCA-200 protein assay kit (obtained from Pierce, Rockford, Ill.). 10 µg of proteins from each cell line were resolved by 12% SDS-PAGE. The separated proteins were transferred onto PVDF membrane (obtained from Amersham, England), followed by immunoblot with human thymidylate synthase monoclonal primary antibody and anti-tubulin monoclonal antibody (manufactured by NeoMarkers, Fremont, Calif.). Horseradish peroxidase linked sheep anti-mouse Ig was used as secondary antibody (Amersham). The ECL plus kit (Amersham) was used for detection of immunoreactivity. The bands corresponding to thymidylate synthase were quantified and normalized to that of tubulin by image analysis (Molecular Dynamics Storm).

RT-PCR Analysis of TS mRNA in Cell Lines

Expression level of human thymidylate synthase transcripts in different cell lines were quantified by using RT-PCR. Oligonucleotide primers for amplification of the human thymidylate synthase and B-actin were designed as follows: Thymidylate synthase sense primer (SEQ ID NO: 1) 5'-GGGCAGATCCAACACATCC-3' (corresponding to bases 208–226 of thymidylate synthase cDNA sequence, Genbank Accession No. X02308), antisense primer (SEQ ID NO: 2) 5'-GGTCAACTCCCTGTCCTGAA-3' (corresponding to bases 564–583), β-actin sense primer (SEQ ID NO: 3) 5'-GCCAACACAGTGCTGTCTG-3' (corresponding to bases 2643–2661 of β-actin gene sequence, Genbank accession no. M10277) and antisense primer (SEQ ID NO: 4) 5'-CTCCTGCTTGCTGATCCAC-3' (corresponding to bases 2937–2955).

Total RNAs were isolated from CCD18co and H630R10 cells, using Rneasy mini kit (obtained from Qiagen, Valencia, Calif.). To monitor for possible DNA contamination, the primers for amplification of β-actin were designed to span the exon4/intron5/exon5 junction. Genomic DNA template leads to a 313 bp β-actin fragment, and cDNA template generates a 210 bp product.

Reverse transcription reactions were performed, using SuperScript preamplification system (Gibco/BRL, Gaithersburg, Md.). 3 µg total RNA was applied in a volume of 20 µl buffer to conduct reverse transcription reaction, followed manufacturer's protocol. PCR reactions were performed in a volume of 48 µl, containing 3 µl of cDNA mixture from reverse transcription reaction, 3 mM MgCl$_2$, 50 mM KCl, 20 mM Tris-Cl, pH 8.4, 0.2 mM of each dNTP, 0.4 µM of thymidylate synthase sense and antisense primers and 3 units of Taq DNA polymerase (obtained from Promega, Madison, Wis.). The reaction mixtures were incubated at 94° C. for 3 min, followed by 10 cycles of 1 min incubation at 94° C., 1 min incubation at 58° C., and then 1 min incubation at 72° C. After 10 cycles, human β-actin primers in 2 µl were added to achieve a final concentration of 0.2 µM, bringing the final reaction volume to 50 µl. PCR reaction was continued to a total of 28 cycles, followed by a 7 min incubation at 72° C.

5 µL of PCR products were resolved by electrophoresis in 2% agarose gel, followed by staining with SYBR Gold nucleic acid gel stain (obtained from Molecular Probes, Eugene, Oreg.). The DNA bands corresponding to thymidylate synthase were quantified and normalized to that of β-actin by Molecular Dynamics Storm.

Northern Blot Analysis

Northern blots were obtained from Invitrogen (Carlsbad, Calif.) and hybridized to a cloned TS cDNA probe. Hybridization signals were normalized vs. ribosomal protein S9 as a housekeeping transcript. A tumor was considered to overexpress TS mRNA if the normalized signal was enhanced at least 2-fold as compared to the normal tissue control.

Cloning, Expression and Purification of Human Thymidylate Synthase

An E coli plasmid expression vector for human thymidylate synthase (TS) was constructed using a modified human TS cDNA in pGCHTS. This clone, obtained from Dr. Dan Santi, contains the complete open reading frame for human TS.

For expression in E. coli the complete human TS ORF was subcloned into the T7 promoter expression vector pET28a (Novagen Inc.). The resulting plasmid vector encodes the synthesis of human TS as a recombinant fusion protein with a six histidine followed by a thrombin cleavage site. This fusion protein adds a total of 20 extra amino acids to the amino terminus of human TS. To produce recombinant protein, the human TS expression vector was introduced into the E. coli strain BL21(DE3), a strain with the T7 RNA polymerase gene inserted into the chromosome under the control of the lac operator.

The human TS-poly-His fusion protein was purified using a metal chelating affinity resin (Novagen Inc.). Protein purification was followed by electrophoresis on 10% SDS polyacrylamide gels. Protein concentrations were determined using the Pierce BCA protein assay. Approximately 10 mg of human TS fusion protein was recovered from a 500 ml culture of E. coli. When visualized with silver stain only the band corresponding to human TS was apparent. The identity of the human TS band was confirmed by performing a Western blot with the anti-TS monoclonal antibody TS106 (NeoMarkers).

Thymidylate Synthase Enzyme Activity Assay

TS activity was measured using the spectrophotometric assay of Wahba and Friedkin (1961). In this assay, TS activity is monitored by measuring the increase in absorbency at 340 nm that occurs when the co-factor 5,10 methylene tetrahydrofolte is oxidized to dihydrofolate as dUTP is converted to dTTP. Enzyme prepared by this method has a specific activity of 0.5–0.65 units/mg protein. One unit is defined as the production of one micromole of dTNP per minute. This value is similar to that reported by Pedersen-Lane et al. (1997).

Experimental Results

These results establish the feasibility of utilizing thymidylate synthase as a cytotoxin generator in tumor cells. In this assay, CCD18co cells (normal colon epithelium), and H630R10, a derivative of H630P which expresses severalfold more thymidylate synthase (Copur et al. (1995)) were employed. A western blot analysis of TS protein levels in each cell type was performed and normalized between samples by comparison with antibody directed vs. human tubulin (Table 5). A rank order of H630R10 (13x) and CCD18co (1x) was obtained.

Comparison of mRNA levels between cell lines as determined by RT-PCR was also performed. See Table 5. Similarly to the western blot analysis, the rank order was H630R10 (24x) and CCD18co (1x), when normalized vs. a β-actin RT-PCR standard.

TABLE 5

Analysis of TS Protein and mRNA Expression in CCD18co and H630R10 cells

| | TS Expression | |
|---|---|---|
| Cell Lines | Relative mRNA Level | Relative Protein Level |
| CCD18co | 1 | 1 |
| H630R10 | 24 | 13 |

HER2 Protooncogene Expression Increases TS Levels in Tumor Cells

TS expression levels in neomycin and HER2/neu-transfected human breast carcinoma cells were assessed using immunoblotting techniques. The results (see FIG. 7) demonstrate an increase in TS expression following transfection and overexpression of human HER2/neu cDNA. Similar results were obtained with HER-2/neu-transfected human ovarian carcinoma cells. The MCF7/HER2 and MCF7/neo cell lines are target cells for assays of this invention because induction of TS is most pronounced (about 20-fold) in these cell types.

The fluoropyrimidine, 5-FUdR, inhibits cell growth via mechanisms similar to 5-FU. This includes cytotoxic effects resulting from incorporation into nucleic acid, as well as inhibition of TS enzyme activity (Goodman and Gilman (1996)). It is therefore expected that cells expressing higher levels of TS will often be more resistant (have a higher $IC_{50}$) than cells which express lower amounts of the enzyme. Table 6 (Line 1) demonstrates that this is the result obtained. Furthermore, as expected from earlier work, BVDU has little activity in the assay (Table 6; line 2). This presumably results from the inability of BVDU to be monophosphorylated by human thymidine kinase, a requirement for binding to thymidylate synthase (Balzarini et al. (1987), Balzarini et al. (1993), Carreras and Santi (1995)). There is no significant difference in sensitivity of the two cell lines to BVDU. Activation of BVDU occurs with phosphoramidation of the 5'-hydroxyl of the ribose moiety. BVDU-PA (Table 6, line 3) has more than 10-fold greater activity on the higher expressing H630R10 cell line than on CCD18co cells.

TABLE 6

Higher Levels of TS Expression Predict Greater Sensitivity to BVDU-PA

| | $IC_{50}(\mu M)^1$ | |
|---|---|---|
| Compound | CCD18co | H630R10 |
| 1. 5-FUdR | 9.5M ± 0.42 | 169.8 ± 2.4 |
| 2. BVDU | 2540 ± 58.2 | 2876.2 ± 54.5 |
| 3. BVDU-PA | 2810.2 ± 75.1 | 216.7 ± 15.7 |

[1]Standard error less than 20%

These two cell lines were then compared with respect to sensitivity to 5FUdR, and the phosphoramidate derivative of BVDU (BVDU-PA). Because 5FUdR inhibits cell growth via the same mechanism as 5FU, it is expected that CCD18co will be more sensitive (have a lower IC-50) than H630R10, since the latter cell line has a higher intracellular level of thymidylate synthase. The data presented in Table 7 demonstrated that this is the result obtained, using the crystal violet assay, described above. This result also illustrates one of the key problems with current cancer chemotherapeutics, ie., that they are often more toxic to normal cells than to cancer cells. The data shown in Table 7 show that normal colon epithelial cells (CCD18co; IC-50=9.5 µM) are approximately 18-fold more sensitive to 5FUdR than are the H630-R10 colon tumor cells (IC-50=169.8). The prodrug substrate, BVDU-PA, however, reverses this relationship. BVDU-PA, which is converted by TS into cytotoxic moieities, is approximately 13-fold more potent on the high TS expression H630R10 cell ($IC_{50}$=216.7) than on the normal colon cell type ($IC_{50}$=2810.2).

TABLE 7

TS Prodrug BVDU-PA has Greater Activity on a Thymidylate Synthase Overexpressing Tumor Cell Line than on Normal Cells (1, 2).

| | $IC_{50}$ | |
|---|---|---|
| Compound | CCD18co (normal colon epithelium) | H630R10 (colon cancer cell line) |
| 5-FUdR (floxuridine) | 9.5 µM | 169.8 µM |
| BVDU-PA | 2810.2 µM | 216.7 µM |

1. Representative data from several assays.
2. Assay performed with triplicate wells at each concentration. Standard error is less than 20%.

This result was confirmed using the Alamar Blue Assay (commercially available from ACCUMED Int., West Lake, Ohio). The data in Table 8, below show that even 5-FU has non-selective properties that make it toxic to normal and tumor cells.

TABLE 8

Normal Cells Are At Least as Sensitive to 5-Fluorouracil as Tumor Cells

| Normal Cells | $IC_{50}$ | Tumor Cells | $IC_{50}$ |
|---|---|---|---|
| Colon Epithelium (CCD18co) | 0.2 | Breast (MCF7) | 0.61 |
| Skin Fibroblast (DET551) | 1.1 | Breast (MDA 468) | 0.40 |
| Lung Epithelium (W138) | 0.4 | Sarcoma (Saos 2) | 11.30 |
| $\overline{X}$ = 0.57 µM | | $\overline{X}$ = 4.10 µM | |

An additional assay of this invention requires candidate drugs to be screened in reaction mixtures containing human thymidylate synthase with and without N5N10-methylenetetrahydrofolate, and the candidate prodrug. The leaving group of the candidate prodrug (e.g., at the pyrimidine 5 position) is labeled, for example, with tritium using methods well known in the art. The control substrate is similarly labeled (e.g. 5-$^3$H) dUMP, under the same reaction conditions. The assays are done similarly to the description provided in Carreras, C. W. and Santi, D. V. (1995), and references cited therein. The human thymidine synthase can be purified from E. coli containing the expressed human thymidylate synthase. See Davisson, V. J. et al. (1989) and Davisson, V. J. et al. (1994). This approach provides a scaleable assay capable of screening large numbers of candidate compounds.

Determination of Intracellular Products of TS Prodrug Metabolism

It is important to determine the intracellular products of TS prodrug metabolism in order to substantiate proposed mechanism of activation and action and to define agents that are candidate thereapeutics. One acceptable view of intracellular metabolism of aryl phosphodiester amidates involves enzymatic conversion into a carboxylic acid, intramolecular rearrangement of the phosphomonoester amidate into to a 5'-monophosphoryl nucleoside (Valette et al. (1996)). However, this mechanism is unlikely to describe intracellular processing of all phosphoramidate-based pronucleotides. For example, a different mechanism was proposed for aryl phosphomonoester amidate processing, one involving the simple direct conversion of the phosphoramidate to the monophosphate species by a phosphoramidate hydrolates (McIntee et al. (1997) and Fries et al. (1995)). Regardless of the mechanism for unmasking the nucleoside monophosphate, this assay will detect products of TS conversion of the intracellular monophosphate to cytotoxic compounds within the cell.

The proposed reaction products of prodrug compounds with TS are shown in FIG. 8. To accomplish this task, cells are incubated with an amount of prodrug compounds that induces 50% growth inhibition of high TS expressing cell lines (in the 72H assay supra.). Both low and high TS expresser cells are used (eg., CCD18co vs. H630R10). Time course studies are performed in which treated cells are processed according to the method described by McIntee et al. (1997). Cells are lysed with 60% methanol in water at −20° C., and particulate residue removed by centrifugation. The supernatants are dried and stored at −20° C. The aliquots are evaluated initially by RP-HPLC and then by LC-MS to document the intracellular conversation of the phosphoramidate to the monophosphate and also the ensuring transformation of the monophosphate by thymidylate synthase.

Documentation of Substrate Activity Utilizing Purified Thymidylate Synthase

This assay determines the specific activities of future TS enzyme preparations, to assure the activity of such preparations over time, and to determine whether compounds screened for suitable activity do inactivate the TS enzyme under in vitro reaction conditions.

To determine what reaction products are produced when prodrug compounds are incubated together with purified recombinant TS enzyme, reaction conditions similar to those employed with the TS activity assay are used to generate reaction products in vitro. These reaction products will be then analyzed by GC-mass spectrometry to identify the actual molecules formed.

In Vivo Efficacy Studies

1. Cell Lines and Cell Culture

MCF7/NEO and MCF7/HER-2-transfected breast cell lines were obtained from Dr. Dennis Slamon (UCLA). MCF7/HER-2-transfected human breast carcinoma cells as well as other HER-2/neu-transfected cell lines demonstrate an increase in TS expression (Pegram et al. (1997)). Thus, in additional to CCD18co and H630R10, these lines are suitable for testing differential response to prodrug. The differential responses are first confirmed in vitro for MCF7/NEO and MCF7/HER-2 cells to 5-FUdR and BVDU-PA using the same in vitro experimental approach described above. The HT1080 tumor cell lines from Dr. Bertino (Banerjee et al. (1998)) are similarly characterized.

2. Xenograft Models for Testing of Prodrug Compounds

MCF7/HER-2 breast cells form xenografts in athymic mice with high efficiency and their growth properties have been thoroughly characterized (Pegram et al. (1997)). The growth properties of this xenograft model are so uniform that a computer model, which can predict the growth trajectory of these tumors following treatment with different drug combinations, has been developed by Dr. Angela Lopez and Dr. Elliot Landau in the Department of Biomathematics at the UCLA School of Medicine (Lopez, et al. pending submission). Because of uniformity and reproducibility of this model, it has become very useful in prectinical testing of novel experimental therapeutics. For example, this model formed the basis for the preliminary in vivo analysis of the drug Herceptin® which has recently been approved by the US Food and Drug Administration for the treatment of metastatic breast cancer (Pegram, et al. (1998)). The colon tumor cell lines (HT1080/NEO and HT1080/E2F1.1) have demonstrated tumorigenicity (Banerjee et al. (1998)).

Ras-transformed NIH 3T3 cell lines are transplanted subcutaneously into immunodeficient mice. Initial therapy may be direct intratumoral injection. The expected result is that increased level of expression of human TS or a target enzyme leads to enhanced antitumor activity by the drug candidates. Similar studies are performed with human tumors expressing increasing levels of human TS or a target enzyme, and demonstrating that efficacy in response to drug correlates with their level of human TS expression or target enzyme. Optionally, experiments are be performed as above except the drug will be administered intravenously into the animals to address issues related to efficacy, toxicity and pharmacobiology of the drug candidates. In a further embodiment, control animals will receive an effective amount of a compound identified above under the section entitled "Prodrugs," supra.

More specifically, the in vivo studies can be conducted by using two different xenograft models ( See Table 9).

TABLE 9

Tumorigenic Cell Lines Used For In Vivo Efficacy Testing

| Xenograft | Relative TS Expression | Cell of Origin | Source |
| --- | --- | --- | --- |
| MCF7/NEO | low (1 X) | human breast carcinoma | Dr. Slamon |
| MCF7/HER2 | high (20 X) | | |
| H630R10 | high (13 X) | human colon carcinoma | Copur et al. (1995) |
| HT1080/NEO | low (1 X) | human colon carcinoma | Dr. Bertino |
| HT1080/E2F1.1 | high (14 X) | | Banerjee et al. (1998). |

Test cells with defined expression of TS (indicated in Table 9) are injected subcutaneously at $5 \times 10^6$/site in the flank region of 4–6 week old (20–25 gram) CD-1 (nu/nu) athymic mice (Charles River Laboratories, Wilmington, Mass.) as described (Pegram, et al. (1997)). Eight mice (four animals per cage) are used for each treatment group (vehicle control solution or prodrug compounds). Two xenografts are established per mouse both reduce the number of animals needed for each experiment and improve the statistical power to detect differences in response between groups. Individual mice are identified by tagging the ears so that xenograft trajectories are calculated for individual mice in addition to the analysis of group means. All mice used in the MCF-7 breast xenograft model are female and, prior to cell injection, are primed with 17B-estradiol (Innovative Research of America, Toledo, Ohio) applied subcutaneously in a biodegradable carrier binder (1.7 mg estradiol/pellet) to promote tumor cell growth. Prospective tumor volumes, calculated as (width$^2$ X length)/2 are monitored twice weekly by serial micrometer measurements by a single blinded observer. Animals are assigned to each treatment group such that the mean starting tumor volumes will be the same in each group. Statistical tests are performed (single-factor ANOVA) to assure uniformity in starting tumor volumes between treatment groups. The prodrugs or isovolumetric vehicle control solution are administered by single I.P. injection in the first set of experiments. If efficacy is identified in the initial experiments, additional studies will be performed using a daily subcutaneous dosing schedule X 5 days with total prodrug dose equal to the $IC_{10}$ defined in the single I.P. dosing studies.

For these efficacy experiments prodrug dosing will commence when the means xenograft volumes in each group reach 5OMM$^3$. Mean tumor volumes of prodrug-treated relative to control-treated animals will be plotted using descriptive statistics with graphical analysis. Statistical tests (single factor ANOVA) will be applied to compare xenograft volume differences between treatment groups. Logtransformation will be applied for ANOVA computations, when indicated, to stabilize variance in xenograft volume data sets. Non-parametric statistical tests can be applied if necessary depending on xenograft volume data distribution. Differences in efficacy between xenograft with high TS expression will be compared to those with low TS expression using prodrug-treated/control-treated tumor volume ratios (T/C ratios) using statistics as described (Pegram, et al. (1997)). This methodology can accommodate differences in intrinsic growth rates between high TS-expressing xenografts and low TS-expressing xenografts.

In vivo studies also can be conducted as described by Harris, MP et al. (1996) and Antelman, D. et al. (1995).

3. Dose Finding Studies in Non-Tumor-Bearing Athymic Mice to Define the Maximum Tolerated Dose (MTD)

Groups of 6 CD-1 nu/nu athymic mice (Charles River Laboratories) (3 male, 3 female) are injected with a single dose of prodrug via the intraperitoneal (I.P.) route. Dosing will begin empirically with the initial dose defined by the amount of a prodrug to achieve a serum concentration equal to the $IC_{50}$ in vitro, assuming the volume of distribution of the prodrug to be restricted to the total body water (TBW) compartment of the mouse (0.6 X body mass in grams $TBW_{mouse}$). If no toxicity is observed at this level, then dose escalation proceeds in groups of 6 mice at half-log intervals. If toxicity is encountered at the empiric dose level, then repeat dose escalation experiments beginning at 10% of the toxic dose will proceed likewise. Mice are observed daily for mobility, grooming behavior, and ability to take food and water. Mouse weights will be assessed weekly. The MTD will be defined as the dose resulting in 10% or less loss in body weight during the observation period, or a dose=90% of the $LD_{10}$. If lethality is encountered at a particular dose level then repeat experiment (assuming no toxicity is observed at this level). The observation period is about 60 days. Dose escalation will proceed in prospective cohorts at 3 week intervals if no toxicity is encountered at a particular dose level.

While the invention has been described in detail and with reference to specific embodiments thereof, it will be apparent to one skilled in the art that various changes and modifications can be made therein without departing from the spirit and scope thereof.

REFERENCES

Literature

Abraham et al. (1996) *J Med Chem.*, Vol. 39, pp. 4569–4575
Agarwala, S. S. etal. (1988) *J.M. Hematol. Oncol. Clin. North Am.* 12(4):823–833
Akdas, A. et al. (1996) *Eur. Urol.* 29(4):483–486
Almasan, A. et al. (1995) *Cancer Metastases Rev.* 14:59–73
Andersen, et al. (1995) *Acta OncoL* 34(4):499–504
Anglada, J. M. (1996) *J. Heterocycl. Chem.* 33:1259–1270
Antelman, D. et al. (1995) *Oncogene* 10:697
Asakura, J. et al. (1988) *Tetrahedron Lett.* 29:2855–2858
Asakura, J. et al. (1990) *J Org Chem.* 55:4928–4933
Balzarini, J. et al. (1987) *Molecular Pharm.* 32:410–16
Balzarini, J. et al. (1985) *Methods Find Exp. Clin. Pharmacol.* 7:19–28
Balzarini, J. et al. (1993) *J BioL Chem.* 268:6332–6337
Balzarini, J. et al. (1996)*Biochem. Biophys. Res. Commun.* 225:363–369
Balzarini, J. et al. (1997) *FEBS Lett.* 410:324–328
Banerjee, D. et al. (1998) *Cancer Res.* 58:4292–4296
Banerjee, D. et al. (1995) *Acta Biochem. Pol.* 42(4):457–464
Barbour, K. W. et al. (1992) Mol. Pharmacol. 42:242–8
Barr, P. J. et al. (1983) *J BioL Chem.* 258(22):13627–13631
Barr, P. J. et al. (1983) *Biochemistry* 22:1696–1703
Barr, P. J. (1981) *J Med Chem.* 24:1385–1388
Barr, P.J. (1983) *J Biol. Chem.* 258:3627–3631
Barrett, J. E. (1998) *J Am. Chem. Soc.* 120:449–450
Bergstrom, D. E. et al. (1984) *J Med Chem.* 27:279–284
Benzaria et al. (1996) *J Med Chem.*, Vol. 39, p. 4958
Bergstrom, et al. (1981) *J Org. Chem* 46:1432–1441
Bertino, J. R. et al. (1996) *Stem Cells* 14:5–9
Bigge, et al (1980) *J Amer. Chem. Soc.* 102:2033–2038
Bohman, C. et al. (1994) *J BioL Chem.* 269:8036–8043
Brison (1993) *Biochem. Biophys. Acta* 1155(1):25–41
Budavari, eds., *Merck Index* (12$^{th}$ Ed., 1996)
Burck, K. B. et al. eds. "Oncogenes: An Introduction to the Concept of Cancer Genes" (Springer-Verlag, New York 1988)
Callahan, A. P., et al. (1989) *Commun Nuci Med* 20: 3–6
Canute, G. W. et al. (1996) *Neurosurgery* 39:976–983
Carreras, C. W. et al. (1995) *Annu Rev. Biochem* 64:721–762
Carter, P. et al. (1992) *Proc. NatL Acad Sci. USA* 89:4285–4289
Cava, M. P. et al. (1985) *Tetrahedron* 41:5061–5087
Chadhuri, N. C. et al. (1995) *J Am. Chem. Soc.* 117:10434–10442
Chakravarty P. K. et al. (1983) *J Med. Chem.* 16(5):638–644
Chen, C. H. et al. (1998) *J Biomed Sci.* 5(4):231–252
Chen, L. et al. (1996) *Cancer Research* 56:1331–1340
Cho, Y. M. et al. (1994) *Tetrahedron Lett.* 25:1149–1152
Christopherson, K. S. et al. (1992) *Proc. Nati. Acad Sci. (USA)* 89:6314–6318
Chu, E. et al. (1996a) *Cancer Treat. Res.* 87:175–195
Chu, E. et al. (1996b) *Adv. Enzyme Regul.* 36:143–163
Clarke, R. (1996) *Brest Cancer Res. Treat.* 39:1–6
Clark, J. W. (1997) *Semin. Oncol.* 24 (Suppl.):518–519
Connors, T. A. (1986) *Xenobiotica* 16(10/11):975–988
Connors, T. A. (1996) *Ann. Oncol.* 7:445
Connors, T. A. and Knox, R. J. (1995) *Stem Cells* 13:501–511
Copur, S. et al. (1995) *Biochem. Pharm.* 49(10):1419–26
Crisp, G. T. (1989) *Synth. Commun.* 19:2117–2123
Dale, et al. (1973) *Proc. Natl. Acad. Sci. USA* 70:2238–2242
Davisson, V. J. et al. (1989) *J Biol. Chem.* 264:9145–48
Davisson, V. J. et al. (1994) *J Biol. Chem.* 269:30740
DeClercq, E. et al. (1983) *J Med Chem.* 26:661–666
Dicken, A. P. et al. (1993) *Proc. Natl. Acad Sci. USA* 90:11797–801
Dirven, H. A. et al. (1995) *Cancer Res.* 55:1701–1706
Dorr, R. T. and Von Hoff, D. D., eds. "Cancer Chemotherapy Handbook" 2nd ed. (Appleton and Lange 1994), pp. 768–773, 1020

Dunn, W. J. et al. (1996) *J Med Chem.* 39:4825

Dyer, R. L. et al. (1991) "Nucleic Acids Chemistry: Improved and New Synthetic Procedures, Methods, and Techniques." Townsend, L. B. & Tipson, R. S., eds. (Wiley-Interscience, New York, N.Y.) Vol. 4:79–83

Eccles, S. A. et al. (1994–95) *Invasion Metast.* 14(1–6):337–348

El-Deiry, W. S. (1997) *Current Opinion in Oncology* 9:79–87

Fan and Bertino, J. R. (1997) *Oncogene* 14(10):1191–1200

Farquhar et al. (1994) *J Med Chem.* 37:3902–3909

Farquhar et al. (1994) *J Med Chem.* 38:488–495

Felip, et al. (1995) *Cancer* 75(8):2147–2152

Findlay, M. P. et al. (1997) *Br. J Cancer* 75:903–909

Finer-Moore, J. S. et al. (1994) *Biochemistry* 33:15459–15468

Finer-Moore, J. et al. (1993) *J Mol. Bio.* 232:1101–116

Freed et al. (1989) *Biochem. PharmacoL* 38:3193–3198

Fries, K. M., et al. (1995) *J Med. Chem* 38:2672–80

Garrett, C. et al. (1979) *Biochem* 18:2798–2804

Goodwin, J. T. et al. (1993) *Tetrahedron Lett.* 34:5549–5552

Gottesmanm, M. M. et al. (1995) *Annu. Rev. Genet.* 29:607–649

Graham, D. et al. (1 998) *J Chem. Soc. Perkin Trans.* 1:1131–1138

Gros, P. et al. (1986a) *Cell* 47:371–80

Gros, P. et al. (1986b) *Nature* 323:728–731

Gros, P. et al. (1986c) *Proc. Natl. Acad Sci. USA* 83:337–41

Gudkov, A. V. et al. (1987) *Somat. Cell Mol. Genet.* 13:609–19

Hamilton-Miller, J. M. T. and Smith, J. T., eds. *B-Lactamases* (Academic Press, 1979)

Hardy, L. W. et al. (1987) *Science* 235:448–455

Harris, M. P. et al. (1996) *Cancer Gene Therapy* 3:121

Hashimoto, Y. et al. (1987) *Anal. Biochem.* 167:340–346

Hashimoto, Y. et al. (1988) *Cancer Biochem. Biophys.* 10:1–10

Haskell, C. M. ed. *Cancer Treatment* 4th Ed., J. Dyson, Ed., (Philadelphia: W. B. Saunders Co. 1995)

Hengstschlager, M. et al. (1996) *Oncogene* 12:1635–43

Hermann, J. G. (1995) *Cancer Res.* 55(20):4525–4530

Hobbs, F. W. Jr. (1989) *J Org. Chem.* 54:3420–3422

Horikoshi, T. et al. (1992) *Cancer Res.* 52:108–116

Hostetler et al. (1997) *Biochem. Pharmacol.* 53:1815

Houze, T. A. (1997) *Tumour BioL* 18:53–68

Hsiao, L. Y. et al. (1981)*J Med Chem.* 24:887–889

Hudziak, R. M. et al. (1988) *Proc. Natl. Acad. Sci. USA* 85:5102–5106

Hudziak, R. M. et al. (1990) *Cell Growth & Differentiation* 1:129–134

Husain, I. et al. (1994) *Cancer Res.* 54:539–546

Hussain, S. P. et al. (1998) *Cancer Res.* 58(18):4023–4027

Imai, K. et al. (1969) *J Org Chem.* 24:1547–1550

Jackman, A. L. (1995) *Anti-Cancer Drug Design* 10:573–589

Jackman, A. L. et al. (1995) *Ann. Oncol.* 6(9):871–881

Johnson, P. G. et al. (1997)*J Clin. OncoL* 15:1923–1931

Johnston, P. G. (1991) *Cancer Res.* 51:6668–6676

Johnston, P. G. (1994) *J Clin. Oncol* 12:2640–2647

Johnston, P. G. (1995) *Cancer Res.* 55:1407–1412

Kamb, A. (1998) *Curr. Top Microbiol. Immunl.* 227:139–148

Kashani-Sabet, et al. (1988) *Cancer Res* 48:5775–5778

Knighton, E. R. et al. (1994) *Nature Struct Biol.* 1:186–194

Kobayashi, H. et al. (1995) *Japanese J Cancer Res.* 86:1014–1018

Komaki, K. (1995) *Breast Cancer Res. and Treat.* 35:157–162

Kormnann, M. (1997) *Cancer Letters* 118:29–35

Kuroboshi, M. et al. (1991) SYNLETT 909–910

Kuroboshi, M. et al. (1994) SYNLETT 251–252

Lasic, D. D. (1996) *Nature* 380:561–2

Lam, K. S. (1997) *Anticancer Drug Research* 12:145–67

Lasic, D. D. (1996) *Nature* 380:561–562

Lee, Y. (1997) *Exp. Cell Res.* 234:270–276

Leichman, C. G. (1997) *J Clin. Oncol.* 15:3223–3229

Lenz, H. J. (1995) *PCR Methods Appl.* 4:305–308

Lewis, J. G. (1996) *Proc. Natl. Acad Sci. USA* 93:3176–3181

Li, W. W. et al. (1995) *Proc. Natl. Acad Sci. USA* 92:10436–10440

Lin W-Y., et al. (1997) *Eur J Nucl. Med* 24: 590–595

Livak, K. J. et al. (1992) *Nucleic Acids Res.* 20:4831–4837

Livingstone, L. R. et al. (1992) *Cell* 70:923–936

Lönn, U. et al. (1996) *Cancer* 77(1):107–112

Lovejoy, et al. (1997) *J Pathol.* 181:130–5

Maelandsmo, G. M. (1996) *Br. J Cancer* 73:909–916

Masters, J. N. and Attardi, G. (1983) *Gene* 21:59–63

McGuigan, C. (1992) *Antiviral Res.* 17:311–321

McGuigan, C. (1998) *Antiviral Chem. Chemother.* 9:187–197

McGuigan, C. (1993) *J Med Chem.* 36:1048–1052

McGuigan, C. (1996) *J Med Chem.* 39:1748–1753

McGuigan, C. et al. (1994) *FEBS Let* 351:11–14

Mclntee, E. J. (1997) *J Med Chem.* 40:3323–3331

McKay, G. A. et al. (1994) *Biochem* 33:6936–6944

Meden, et al. (1994) *J Cancer Res. Clin. Oncol.* 120(6):378–81

Meier et al. (1997) *Bioorg Med Chem. Lett.* 7:1577

Meier et al. (1997) *Bioorg. Med Chem. Lett.* 7:99

Meier et al., (1997) *International Antiviral News.* 5:183

Melton, R. G. and Sherwood, R. E. (1996)*J Natl. Cancer Inst.* 88:153–65

Miller, J. H. "A short course in bacterial genetics: A laboratory manual and handbook for E. coli and related bacteria" (Cold Spring Harbor Press 1992)

Mitchell, M. S. (1996) *J Investig. Dermatol. Symp. Proc.* 1(2):215–218

Montfort, W. R. et al. (1997) *Phannacol. Ther.* 76(1–3):2943

Morgan, A. S. et al. (1998) *Cancer Res.* 58:2568–2575

Murakami et al. (1998) *Mutat. Res.* 400(1–2):421–437

Nakano, T. et al. (1994) *Biochemistry* 33:9945–52

Noder, et al. (1996) *Pathol. Res. Pract.* 192:768–80

Osaki, M. et al. (1997) *Apoptosis* 2:221–226

Parr, A. (1998) *Biochem. Pharmacol.* 56:231–235

Pederson-Lane, J. (1997) *Protein Expression and Purification* 10:256–262

Pegram, M. D. (1998) *J Clin. Oncol.* 16(8):2659–2671
Pegram, M. D. et al. (1997) *Oncogene* 15:537–547
Perry, K. et al. (1990) *Proteins* 8:315–333
Pestalozzi, B. C. (1997) *J Clin. Oncol.* 15:1923–1931
Peters, G. J. et al. (1995) *Eur. J Cancer* 31A:1299–1305
Phelps, M. E. et al. (1980) *J Med. Chem.* 23:1229–1232
Pupa, et al. (1993) *Oncogene* 8(11):2917–23
Rigg, A. et al. (1997) *Mol. Med Today* 3:359–366
Roberts, D. (1966) *Biochem.* 5:3546–3548
Robins, M. J. et al. (1983) *J Org Chem.* 48:1854–1862
Robins, M. J. et al. (1981) *Tetrahedron Lett.* 22:421–424
Robins, M. J. et al. (1982) *Can. J Chem.* 60:554–557
Roninson, I. B. et al. (1984) *Nature* 309:626–28
Rustum, Y. M. (1997) *J Clin Oncol.* 15(1):389–400
Ruth, J. L. et al. (1978) *J Org Chem.* 43:2870–2876
Sambrook, et al., eds. "Molecular Biology: A Laboratory Manual" ($2^{nd}$ ed.) (Cold Spring Harbor Press 1989)
Santi, D. V. (1980) *J Med Chem.* 23:103–111
Sastry et al., (1992) *Mol. Pharmacol* 41:441–445
Sauter, et al. (1993) *Cancer Res.* 53(10 Suppl.):2199–203
Schaechter, M. et al., eds. "Mechanisms of Microbial Disease" ($2^{nd}$ ed.) (Williams and Wilkins 1993)
Schiffer, C. A. et al. (1995) *Biochemistry* 34:16279–16287
Schimke, R. T. et al. (1988) *J Biol. Chem.* 263:5989–5992
Segovia, M. (1994) *Ann. Tropical Med Paras.* 88(2):123–130
Shepard, H. M. et al. (1988) *J Clin. Immunol.* 8:353–395
Simon, S. M. and Schindler, M. (1994) *Proc. Natl. Acad Sci. USA* 91(9):3497–3504
Slamon, D. J. et al. (1987) *Science* 235:177–182
Slamon, D. J. et al. (1989) *Science* 244:707–712
Smith, K. A. et al. (1995) *Philos Tran Royal Soc* 347:49–56
Snydman, D. R. et al. (1996) *Clinical Infectious Diseases* 23(Suppl. 1):554–65
Spector, D. L. et al. (1997) "Cells, A laboratory manual"
Stühlinger, M. et al. (1994) *J Steroid Biochem. Molec. BioL* 49(1):39–42
Sugarman, B. J. et al. (1985) *Science* 230:943–945
Sukumar and Barbacid (1990) *Proc. Natl. Acad Sci. USA* 87(2):718–722
Takeishi, K. et al. (1985) *Nucl. Acid Res.* 13:2035–2043
Takemura, Y. et al. (1997) *Anticancer Drugs* 8(1):3–16
Tannock, I. F. (1996) *J Clin. Oncol.* 14(12):3156–3174
Tolstikov, V. V. et al. (1997) *Nucleosides Nucleotides* 16:215–225
Troutner, D. A. (1987) *Nuc.l Med Bio.l* 14: 171–176
Valette et al. (1996) *J Med Chem* 39:1981
Van Den Berg, C. L. (1994) *Anti-Cancer Drugs* 5:573–578
van de Vijver, et al. (1987) *Mol. Cell. Biol.* 7(5):2019–23
Vlaykova, T. (1997) *Oncology* 54:146–152
Voet, et al. eds. *Biochemistry* 2nd Ed. (John Wiley & Sons, Inc. 1995)
Volm, M. et al. (1996) *Critical Rev. in Oncogenesis* 7:227–244
Volm, M and Mattern, J. (1992) *Anticancer Res.* 12(6B):2293–6
Wahba, A. J. et al. (1961) *J Biol. Chem.* 236(3):C11
Wall, M. E. (1998) *Med Res. Rev.* 18:229–314
Wataya, Y. (1979) *J Med Chem.* 22:339–340
Wettergren, Y. et al. (1994) *Mol. Genet.* 20:267–85
Wilson, J. D., et al. (eds.) "Harrison's Principles of Internal Medicine" ($12^{th}$ ed) (McGraw-Hill, Inc. 1991) 2208, esp. 21–76
Yamachika, T. (1998) *Cancer* 82:70–77
Yeh, K. H. et al. (1998) *Chemotherapy Cancer* 82(9):1626–1631
Yin, Y et al. (1992) *Cell* 70:937–948
Yin, Y. et al. (1994) *Cancer Res.* 54:3686–91

Patent Documents

U.S. Pat. No. 4,247,544, Bergstrom, D. E. et al. "C-5 Substituted Uracil Nucleosides", issued Jan. 27, 1981
U.S. Pat. No. 4,267,171, Bergstrom, D. E. et al. "C-5 Substituted Cytosine Nucleosides" issued May 12, 1981
U.S. Pat. No. 4,948,882, Ruth, J. L. "Single-Stranded Labelled Oligonucleotides, Reactive Monomers and Methods of Synthesis" issued Aug. 14, 1990
U.S. Pat. No. 4,975,278, Senter, P. D. et al. "Anti-body-Enzyme Conjugates in Combination with Prodrugs for the Delivery of Cytotoxic Agents to Tumor Cells" issued Dec. 4, 1990
U.S. Pat. No. 5,085,983, Scanlon, K. J. "Detection of human tumor progression and drug resistance" issued Feb. 4, 1992
U.S. Pat. No. 5,233,031, Borch, R. F. et al. "Phosphoramidate Analogs of 2'-Deoxyuridine" issued Aug. 3, 1993
U.S. Pat. No. 5,264,618, Felgner, P. L. et al. "Cationic Lipids for Intracellular Delivery of Biologically Active Molecules" issued Nov. 23, 1993
U.S. Pat. No. 5,459,127, Felgner, P. L. et al. "Cationic Lipids for Intracellular Delivery of Biologically Active Molecules" issued Oct. 17, 1995
U.S. Pat. No. 5,627,165, Glazier, A. "Phosphorous Prodrugs and Therapeutic Delivery Systems Using Same" issued May 6, 1997
PCT Application WO 91/17474, published Nov. 4, 1991
Hostetler et al., Patent Application No. WO 96/140088 (1996)

What is claimed is:

1. A compound of the formula:

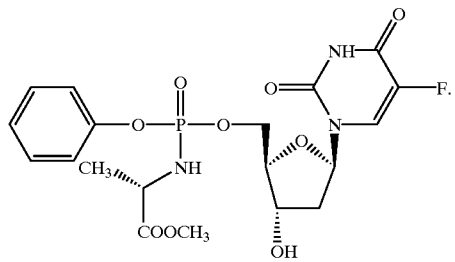

and its pharmaceutically acceptable salts.

2. A compound of the formula:

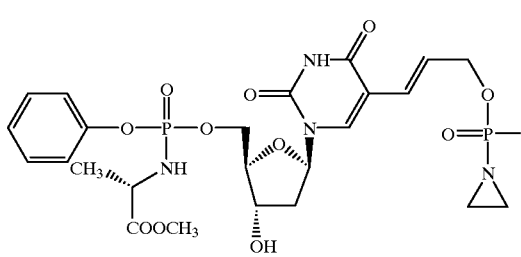

and its pharmaceutically acceptable salts.

3. A compound of the formula:

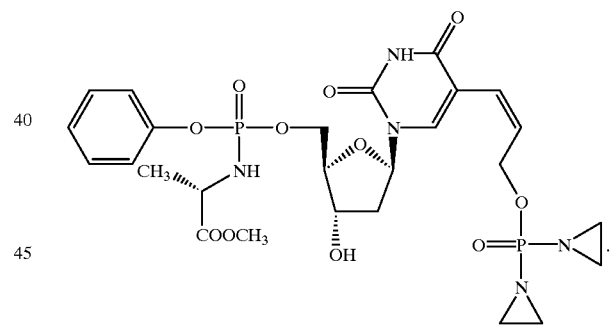

and its pharmaceutically acceptable salts.

4. A compound of the formula:

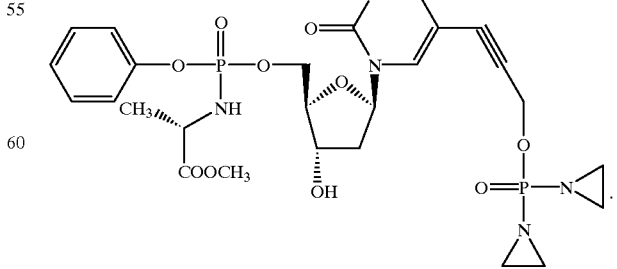

and its pharmaceutically acceptable salts.

5. A method of forming a compound of the formula:

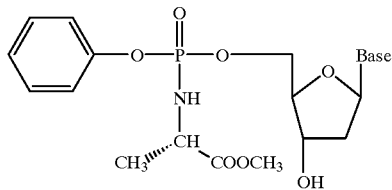

wherein "Base" denotes a nucleic acid base;

which method comprises the step of reacting a compound of the formula:

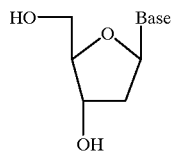

with a compound of the formula:

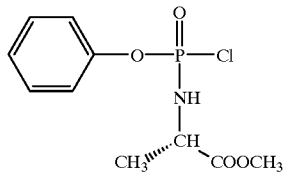

in the presence of an HCl scavenger.

6. A method of forming a compound of the formula:

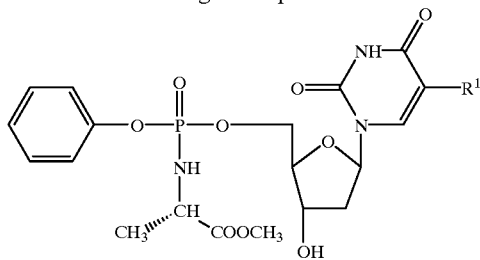

wherein $R^1$ is a substituent;

which method comprises the step of reacting a compound of the formula:

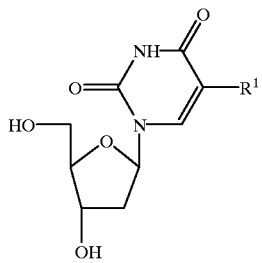

with a compound of the formula:

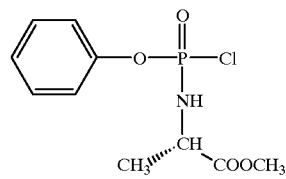

in the presence of an HCl scavenger.

7. The method according to claim 5 or 6, wherein said HCl scavenger is imidazole.

8. The method according to either claim 5 or claim 6, wherein said reaction is performed in a non-aqueous solvent comprising dimethylformamide.

9. The method according to claim 7, wherein said reaction is performed in a non-aqueous solvent comprising dimethylformamide.

* * * * *

SEQUENCE LISTING

<160> NUMBER OF SEQ ID NOS: 4

<210> SEQ ID NO 1
<211> LENGTH: 19
<212> TYPE: DNA

```
<213> ORGANISM: Homo sapiens

<400> SEQUENCE: 1
gggcagatcc aacacatcc                                            19

<210> SEQ ID NO 2
<211> LENGTH: 20
<212> TYPE: DNA
<213> ORGANISM: Homo sapiens

<400> SEQUENCE: 2
ggtcaactcc ctgtcctgaa                                           20

<210> SEQ ID NO 3
<211> LENGTH: 19
<212> TYPE: DNA
<213> ORGANISM: Homo sapiens

<400> SEQUENCE: 3
gccaacacag tgctgtctg                                            19

<210> SEQ ID NO 4
<211> LENGTH: 19
<212> TYPE: DNA
<213> ORGANISM: Homo sapiens

<400> SEQUENCE: 4
ctcctgcttg ctgatccac                                            19
```